United States Patent
Beyer et al.

(10) Patent No.: US 7,824,897 B2
(45) Date of Patent: Nov. 2, 2010

(54) MODIFIED TUMOR NECROSIS FACTOR-ALPHA CONVERTING ENZYME AND METHODS OF USE THEREOF

(75) Inventors: Brian M. Beyer, Lincroft, NJ (US); Richard N. Ingram, Scotch Plains, NJ (US); Peter Orth, New York, NY (US); Corey O. Strickland, Martinsville, NJ (US)

(73) Assignee: Schering Corp., Kenilworth, NJ (US)

( * ) Notice: Subject to any disclaimer, the term of this patent is extended or adjusted under 35 U.S.C. 154(b) by 0 days.

(21) Appl. No.: 12/702,760

(22) Filed: Feb. 9, 2010

(65) Prior Publication Data
US 2010/0184111 A1 Jul. 22, 2010

Related U.S. Application Data

(62) Division of application No. 12/420,323, filed on Apr. 8, 2009, now Pat. No. 7,700,753, which is a division of application No. 11/582,710, filed on Oct. 18, 2006, now Pat. No. 7,529,628, which is a division of application No. 10/444,257, filed on May 21, 2003, now Pat. No. 7,138,264.

(60) Provisional application No. 60/383,391, filed on May 24, 2002.

(51) Int. Cl.
*C12N 9/64* (2006.01)
*C12N 5/10* (2006.01)
*C12Q 1/37* (2006.01)
*G01N 31/00* (2006.01)

(52) U.S. Cl. .................. 435/226; 435/219; 435/23; 435/325; 435/252.3; 436/4

(58) Field of Classification Search ................ None
See application file for complete search history.

(56) References Cited

U.S. PATENT DOCUMENTS

| | | | |
|---|---|---|---|
| 5,594,106 A | 1/1997 | Black et al. | |
| 5,830,742 A | 11/1998 | Black et al. | |
| 5,972,331 A | 10/1999 | Reichert et al. | |
| 5,978,740 A | 11/1999 | Armistead et al. | |
| 6,013,466 A | 1/2000 | Black et al. | |

FOREIGN PATENT DOCUMENTS

WO WO 99/40182 8/1999

OTHER PUBLICATIONS

Brünger, et al. "Slow-cooling protocols for crystallographic refinement by simulated annealing", *Acta Cryst.* A46:585-593 (1990).
Zask, et al. "Inhibition of matrix metalloproteinases: Structure based design", *Current Pharmaceutical Design* 2:624-661 (1996).
Black, et al. "A metalloproteinase disintegrin that releases tumour-necrosis factor-α from cells", *Nature* 385:729-733 (1997).
Moss, et al. "Cloning of a disintegrin metalloproteinase that processes precursor tumour-necrosis factor-α", *Nature* 385:733-736 (1997).
Adams, et al. "Cross-validated maximum likelihood enhances crystallographic simulated annealing refinement", *Proc. Natl. Acad. Soc. USA* 94:5018-5023 (1997).
Brünger, et al. "Crystallography & NMR System: A new software suite for macromolecular structure determination", *Acta Cryst.* D54:905-921 (1998).
Maskos, et al. "Crystal structure of the catalytic domain and human tumor necrosis factor-α-converting enzyme", *Proc. Natl. Acad. Sci. USA* 95:3408-3412 (1998).
Schlöndorff, et al. "Metalloprotease-disintegrins: Modular proteins capable of promoting cell-cell interactions and triggering signals by protein-ectodomain shedding", *Journal of Cell Science* 112:3603-3617 (1999).
Wang, et al., "Two-stage PCR protocol allowing introduction of multiple mutations, deletions and insertions using QuikChange™ site-directed mutagenesis", *BioTechniques* 26:680-682 (1999).
Qi, et al. "Minireview—Tumor necrosis factor-α-induced insulin resistance in adipocytes", *Society for Experimental Biology and Medicine* 223:128-135 (2000).
Black "Molecules in focus—Tumor necrosis factor-α-converting enzyme", *The International Journal of Biochemistry & Cell Biology* 34:1-5 (2002).
Bursi, et al. "A three-dimensional quantitative structure-activity relationship study of heparin-binding epidermal growth factor shedding inhibitors using comparative molecular field analysis", *J. Med. Chem.* 45:781-788 (2002).
Letavic, et al. "Synthesis and biological activity of selective pipecolic acid-based TNF-α Converting Enzyme (TACE) Inhibitors", *Bioorganic & Medicinal Chemistry Letters* 12:1387-1390 (2002).
Althoff et al., "Shedding of interleukin-6 receptor and tumor necrosis factor alpha. Contribution of the stalk sequence to the cleavage pattern of transmembrane proteins.", *Eur. J. Biochem.* 267(9):2624-31 (2000).
Goodsell, et al., "Automated Docking of Flexible Ligands: Applications of AutoDock", Journal of Molecular Recognition, vol. 9, pp. 1-5, (1996).
Bohm, et al., "The computer program LUDI: A new method for the de novo design of enzyme inhibitors", Journal of Computer-Aided Molecular Design, vol. 6, pp. 61-78 (1992).

(Continued)

*Primary Examiner*—Suzanne M Noakes

(57) ABSTRACT

The present invention discloses a modified tumor necrosis factor-alpha converting enzyme (TACE) catalytic domain, that unlike the native TACE catalytic domain, is stable at high protein concentrations. The present invention further discloses methods for generating crystals of the modified TACE protein in protein-ligand complexes with a number of inhibitors. In addition, the present invention discloses methods of using the proteins, crystals and/or three-dimensional structures obtained to identify compounds that can modulate the enzymatic activity of TACE.

6 Claims, 1 Drawing Sheet

OTHER PUBLICATIONS

Appendix A: Alignment of SEQ ID No. 8 and Black et al., Crystallized Protein.

McPherson, A., "Current approaches to macromolecular crystallization", European Journal of Biochemistry, vol. 189, pp. 1-23, (1990).

Kundrot, C.E., "Which strategy for a protein crystallization project?", Cellular Molecular Life Science, vol. 61, pp. 525-536 (2004).

Cudney R., "Protein Crystallization and Dumb Luck", The Rigaku Journal, vol. 16, No. 1, pp. 1-7 (1999).

Ginalski, K., "Comparative modeling for protein structure prediction", vol. 16, pp. 172-177 (2006).

Dean, P., "Recent Advances in Drug Design Methods: Where will They Lead?", BioEssays, vol. 16, No. 9, pp. 683-687 (1994).

MODIFIED TUMOR NECROSIS FACTOR-ALPHA CONVERTING ENZYME AND METHODS OF USE THEREOF

CROSS-REFERENCE TO RELATED APPLICATIONS

This application is a divisional of U.S. application Ser. No. 12/420,323, filed Apr. 8, 2009, now U.S. Pat. No. 7,700,753, which is a divisional of U.S. application Ser. No. 11/582,710, filed Oct. 18, 2006, now U.S. Pat. No. 7,529,628, which is a divisional of U.S. patent application Ser. No. 10/444,257; filed May 21, 2003; now U.S. Pat. No. 7,138,264; which claims the benefit of U.S. provisional patent application No. 60/383,391 filed May 24, 2002, the contents of each of which are hereby incorporated by reference in their entireties.

BACKGROUND OF THE INVENTION

1. Field of Invention

The present invention pertains to a modified tumor necrosis factor-alpha converting enzyme (TACE). The present invention further pertains to generating a crystal of the modified TACE protein in protein-ligand complex with a selected inhibitor for use in structure based rational drug design. In addition, the present invention pertains to methods of using these proteins and crystals to identify compounds that can modulate the enzymatic activity of TACE.

2. Background

Tumor necrosis factor-alpha (TNF-alpha) plays a major role in the immune and inflammatory responses in mammals [Qi and Pekala, *Proc Soc Exp Biol Med.* 223(2):128-135 (2000)]. First isolated from the serum of rabbits that had been treated with endotoxin, TNF-alpha was named for its ability to trigger the hemorrhagic necrosis of specific transplantable tumors [Old, *Science* 230:630-633 (1985)]. Subsequently, TNF-alpha was found to be identical to cachetin, a protein that is intimately involved in cachexia, the wasting disease prevalent in AIDS and cancer [Beutler et al., *J. Exp. Med.,* 161:984-995 (1985)].

TNF-alpha can bind to two distinct cell membrane receptors (TNFR1 and TNFR2) to transduce intercellular signals to a variety of different target cells in a number of different tissues [Qi and Pekala, *Proc Soc Exp Biol Med.* 223(2):128-135 (2000)]. Though a central participant in several key cellular processes, TNF-alpha also functions deleteriously as a mediator of insulin resistance in diabetes mellitus [Hotamisligil and Spiegelman, *Diabetes* 43:1271-1278 (1994)]. In addition, an over-abundance of the active form of TNF-alpha has been linked to adverse symptoms in a number of disease states, including in rheumatoid arthritis, Crohn's disease, sepsis, and cachexia. Since there are presently no effective treatments for these conditions, there remains a need to find new drugs that can be used to modulate the effective physiological concentration of the active form of TNF-alpha.

TNF-alpha is transcribed as a transmembrane protein having a monomeric molecular weight of 26 kilodaltons [Shirai et al., *Nature* 313:803-806 (1985)]. A metalloprotease, tumor necrosis factor-alpha converting enzyme (TACE) cleaves the membrane-associated form of TNF-alpha at a specific site of the protein, converting it to its corresponding soluble form [Black et al., *Nature* 385:729-733 (1997); Moss et al., *Nature* 385:733-736 (1997); U.S. Pat. No. 5,830,742, Issued Nov. 3, 1998; U.S. Pat. No. 6,013,466, Issued Jan. 11, 2000, the contents of which are hereby incorporated by reference in their entireties]. The soluble form of TNF-alpha then associates as a homotrimer of three 17 kilodalton monomers [Kriegler et al., *Cell,* 53:45-53 (1988)]. Although the membrane-associated form of TNF-alpha appears to be active, it is the proteolyzed soluble form that is responsible for the mortality associated with endotoxic shock [Gearing et al., *Nature* 370: 555-558 (1994)]. Thus, reducing the circulating concentration of active TNF-alpha appears to be critical to alleviate the harmful side effects caused by this cytokine. One means for achieving this reduction in concentration of soluble TNF-alpha is to inhibit the TACE protease.

TACE, also referred to as ADAM 17 and CD156q, is a zinc endopeptidase that is a member of the "A Disintegrin And Metalloprotease" (ADAM) family of metalloproteases [Schlondorff and Blobel, *J. Cell Sci.,* 112:3603-3617 (1999); Black, *Intern. J. Biochem. Cell Biol* 34:1-5 (2002); U.S. Pat. No. 5,830,742, Issued Nov. 3, 1998, the contents of all of which are hereby incorporated by reference in their entireties]. A type I transmembrane protein, TACE comprises (i) an extracellular region having an N-terminal signal peptide, (ii) a pro domain, (iii) a zinc-dependent catalytic domain, (iv) a disintegrin domain, (v) an EGF-like domain, (vi) a crambin-like domain, (vii) a transmembrane helix and (viii) an intracellular C-terminal tail [see WO9940182, Published Aug. 12, 1999]. More recently, the EGF-like and the crambin-like domains have been grouped together and re-named as a cysteine-rich domain [Black, *Intern. J. Biochem. Cell Biol* 34:1-5 (2002)].

Since TACE is a protease, the portion of the enzyme that is critical for drug discovery is its catalytic domain. The catalytic domain (TCD) of TACE comprises 263 amino acid residues preceded by a furin cleavage site (residues 211-214). The pro domain comprises a cysteine that interacts with the zinc molecule at the active-site preventing proteolytic action. Therefore, this cysteine must be displaced in order to generate an active protease [Black, *Intern. J. Biochem. Cell Biol* 34:1-5 (2002)].

Zask et al. have prepared a compilation of inhibitors of metalloproteinases [*Curr. Pharm. Des.,* 2:624-661 (1996), the contents of which are hereby incorporated by reference in their entireties], and more recently, Letavic et al. has disclosed several specific inhibitors of TACE [*Biorgan. & Medic. Chem. Lett.* 12:1387-1390 (2002), the contents of which are hereby incorporated by reference in their entireties]. To date, however, none of these has proven to be useful in the treatment of conditions related to an over-abundance of soluble TNF-alpha.

Three-dimensional structures of two different TACE-inhibitor complexes have been obtained via X-ray crystallographic analyses [Letavic et al., *Biorgan. & Medic. Chem. Lett.* 12:1387-1390 (2002); WO9940182, Published Aug. 12, 1999, U.S. application Ser. No. 09/117,476, filed Jan. 27, 1999, the contents of which are all hereby incorporated by reference in their entireties]. Importantly, however, the conditions for preparing the two TACE-inhibitor complexes were significantly different. These results suggest that new crystallization conditions may be required for every different TACE-ligand complex. Determining crystallization conditions, de novo can be extremely time-consuming. Moreover, such a requirement severely hampers progress in identifying new and more potent inhibitors of TACE which are necessary for developing safe and effective drugs to ameliorate the deleterious effects due to an overabundance of the soluble form of TNF-alpha.

Therefore, there is need to provide methods for performing X-ray crystallographic structural determinations on multiple TACE protein-ligand complexes without having to determine crystallization conditions, de novo. In addition, there is a need to obtain X-ray diffractable crystals of the TACE catalytic domain that are stable. Furthermore, there is a need to obtain crystals of the TACE catalytic domain that are amenable to ligand exchange.

The citation of any reference herein should not be construed as an admission that such reference is available as "prior art" to the instant application.

SUMMARY OF THE INVENTION

The present invention discloses that the native TACE protein unexpectedly undergoes autoproteolysis at the high protein concentrations required for X-ray crystallography. The present invention further identifies the peptide bond between amino acid residues Tyr352 and Val353 ($Y_{352}$-$V_{353}$) of SEQ ID NO: 2 as the specific cleavage site.

Therefore, the present invention provides a polypeptide comprising a modified TACE catalytic domain that is significantly less susceptible to autoproteolysis than the native TACE. The modified TACE of the present invention imparts improved stability to the protease under the conditions employed to generate TACE crystals. The present invention also uniquely enables X-ray crystallographic structural determinations to be performed on multiple TACE protein-ligand complexes in rapid succession. This ability to rapidly generate three-dimensional structures of TACE protein-ligand complexes is critical for a successful structure based rational drug design program.

Indeed, the structural information generated using the compositions and methods of the present invention greatly facilitates the identification of new and more potent inhibitors of the TACE protease. Selected inhibitors, in turn, become lead candidates in the development of drugs that will be useful for counteracting the harmful effects due to an overabundance of the soluble form of TNF-alpha, i.e., drugs that can be used in the treatment of rheumatoid arthritis, Crohn's disease, sepsis, and/or cachexia.

One aspect of the present invention provides a polypeptide comprising the amino acid sequence of SEQ ID NO: 8. In one such embodiment, the polypeptide consists essentially of the amino acid sequence of SEQ ID NO: 8. In a particular embodiment, the amino acid residue at position 139 of SEQ ID NO: 8 is serine.[1] In another embodiment of this type, the amino acid residue at position 139 of SEQ ID NO: 8 is alanine. In a preferred embodiment, the amino acid residue at position 139 of SEQ ID NO: 8 is glycine (denoted as "vgTACE" in the Example below, and has the amino acid sequence of SEQ ID NO: 20).

[1] The amino acid sequences of the TACE catalytic domain and the modified TACE catalytic domain are SEQ ID NOs: 6 and 8, respectively. Position 139 of SEQ ID NOs: 6 and 8 is equivalent to position 353 of SEQ ID NO: 2, the amino acid sequence of the TACE polypeptide comprising the Pre, Pro and catalytic domains.

In a related embodiment, the present invention provides a polypeptide comprising a modified TACE catalytic domain comprising at least 95% identity with the amino acid sequence of SEQ ID NO: 8. Preferably, this polypeptide catalyzes the proteolytic cleavage of SEQ ID NO: 17 and/or binds to N-{D,L-2-(hydroxyaminocarbonyl)methyl-4-methylpentanoyl}-L-3-amino-2-dimethylbutanoyl-L-alanine, 2-(amino)ethyl amide and/or binds to N-{3-(hydroxyaminocarbonyl)-1-oxo-(2R)-benzylpropyl}-Ile-Leu-OH. In one such embodiment, the polypeptide consists essentially of a modified TACE catalytic domain having at least 95% identity with the amino acid sequence of SEQ ID NO: 8. In one specific embodiment of this type, the amino acid residue at position 139 of SEQ ID NO: 8 is alanine. In another embodiment, the amino acid residue at position 139 of SEQ ID NO: 8 is glycine. In yet another embodiment, the amino acid residue at position 139 of SEQ ID NO: 8 is serine.

The present invention also provides the full-length TACE polypeptide and fragments thereof that comprise the TACE modified catalytic domain. In one such embodiment the TACE protein comprises (i) the pre domain, (ii) the pro domain, and (iii) the modified catalytic domain. In another embodiment, the fragment of the TACE polypeptide comprises the pro domain, and the modified catalytic domain.

Chimeric proteins comprising the polypeptides of the present invention are also part of the present invention. In a particular embodiment, the chimeric TACE is a fusion protein comprising (i) the pre domain, (ii) the pro domain, (iii) the modified catalytic domain and (iv) a polyhistidine tag. In another embodiment, the chimeric protein comprises the modified catalytic domain and a polyhistidine tag. In a preferred embodiment, the polyhistidine tag further comprises a glycyl-seryl (i.e., Gly-Ser) linker.

The present invention further provides nucleic acids that encode the polypeptides and chimeric proteins of the present invention (see e.g., Table 1 below). In a particular embodiment, the nucleic acid encodes a polypeptide having the amino acid of SEQ ID NO: 8. The present invention further provides expression vectors that comprise the nucleic acids of the present invention and a transcriptional control sequence. Preferably the nucleic acids of the present invention are operatively linked to the transcriptional control sequences in the expression vectors. Host cells comprising the expression vectors are also part of the present invention.

In addition, the present invention provides methods for producing the above-mentioned polypeptides. One such embodiment comprises culturing a host cell of the present invention that produces the polypeptides. Methods for purifying the resulting recombinant polypeptides are also included in the present invention, as are the purified recombinant polypeptides.

Crystals, each comprising one of the protein-ligand complexes of the present invention, are also contemplated. Preferably, such crystals effectively diffract X-rays for the determination of the atomic coordinates of the protein-ligand complex to a resolution of greater than 5.0 Angstroms. More preferably, a crystal of the present invention effectively diffracts X-rays for the determination of the atomic coordinates to a resolution of greater than 3.5 Angstroms. Even more preferably, a crystal of the present invention effectively diffracts X-rays for the determination of the atomic coordinates equal to or greater than 3.0 Angstroms. Still more preferably, a crystal of the present invention effectively diffracts X-rays for the determination of the atomic coordinates equal to or greater than 2.5 Angstroms, and, yet even more preferably, equal to or greater than 2.0 Angstroms. Most preferably, a crystal of the present invention effectively diffracts X-rays for the determination of the atomic coordinates equal to or greater than 1.5-1.7 Angstroms.

In a particular embodiment, the crystal comprises a protein-ligand binding complex in which the polypeptide comprises the amino acid sequence of SEQ ID NO: 8. In another embodiment, the crystal comprises a polypeptide comprising a protein-ligand binding complex in which the polypeptide comprises a modified TACE catalytic domain having at least 95% identity with the amino acid sequence of SEQ ID NO: 8. Preferably this polypeptide catalyzes the proteolytic cleavage of SEQ ID NO: 17, and/or binds to the compound, N-{D,L-2-(hydroxyaminocarbonyl)methyl-4-methylpentanoyl}-L-3-amino-2-dimethylbutanoyl-L-alanine, 2-(amino)ethyl amide and/or binds to N-{3-(hydroxyaminocarbonyl)-1-oxo-(2R)-benzylpropyl}-Ile-Leu-OH. In one particular embodiment of this type, the crystal of the present invention has the space group P2₁2₁2₁, with unit cell dimensions of: a=73, b=75, c=103 Angstroms.

Another aspect of the present invention provides methods for obtaining a crystal comprising a protein-ligand complex between a substitute ligand and a modified TACE catalytic domain. One such method comprises incubating (e.g., soaking) an excess of a substitute ligand with a crystal comprising a modified TACE catalytic domain and an initial ligand in a protein-ligand binding complex. The incubation is performed under the appropriate conditions and for a sufficient time period for the substitute ligand to replace the initial ligand in the protein-ligand complex. A crystal comprising the protein-ligand complex between the substitute ligand and the modified TACE catalytic domain is thus, obtained. The modified TACE catalytic domain can be part of a larger polypeptide (e.g., the full-length TACE or a chimeric protein). In a preferred embodiment, the modified TACE catalytic domain comprises the amino acid sequence of SEQ ID NO: 8. In a one such embodiment, the modified TACE catalytic domain comprises the amino acid sequence of SEQ ID NO: 20. In a preferred embodiment, the initial ligand is N-{D,L-2-(hydroxyaminocarbonyl)methyl-4-methylpentanoyl}-L-3-amino-2-dimethylbutanoyl-L-alanine, 2-(amino)ethyl amide. In a particular embodiment of this type, the substitute ligand is N-{3-(hydroxyaminocarbonyl)-1-oxo-(2R)-benzylpropyl}-Ile-Leu-OH. The present invention further provides the crystals that comprise protein-ligand binding complexes that have had their initial ligand replaced with a substitute ligand.

In an alternative embodiment, the present invention provides a method for identifying an agent for use as an inhibitor of TACE. One such embodiment comprises obtaining a set of atomic coordinates that define the three-dimensional structure of the protein-ligand binding complex from a crystal of the present invention. A potential agent is then selected by performing rational drug design with the atomic coordinates obtained. Preferably, the selection is performed in conjunction with computer modeling. The potential agent is contacted with a proteolytic polypeptide that comprises the catalytic domain of TACE, or alternatively, an active fragment thereof. The catalytic activity of the proteolytic polypeptide is then determined in a TACE activity assay. A potential agent is identified as an agent that inhibits TACE when there is a decrease in the activity of the proteolytic polypeptide in the presence of the agent relative to in its absence.

In a related embodiment, a method of identifying a compound that is predicted to inhibit TACE is provided. One such embodiment comprises using the atomic coordinates in Table 3 to define the structure of the complex between the modified catalytic domain of TACE and N-{3-(hydroxyaminocarbonyl)-1-oxo-(2R)-benzylpropyl}-Ile-Leu-OH and/or to define the structure of a portion of that complex. The portion of the complex defined is required to comprise sufficient structural information to enable the identification of a given compound as a potential inhibitor. A compound then is identified as one predicted to inhibit TACE through the use of the defined structure. A particular embodiment of this type further comprises contacting the compound with a proteolytic polypeptide comprising the catalytic domain of TACE or an active fragment thereof and determining the catalytic activity of the proteolytic polypeptide in a TACE activity assay. A potential agent is identified as an agent that inhibits TACE when there is a decrease in the activity of the proteolytic polypeptide in the presence of the agent relative to in its absence.

The present invention further provides a computer comprising a three-dimensional representation of a protein-ligand complex between a modified TACE catalytic domain and N-{3-(hydroxyaminocarbonyl)-1-oxo-(2R)-benzylpropyl}-Ile-Leu-OH in computer memory. One such embodiment comprises: (i) a machine-readable data storage medium comprising a data storage material encoded with machine-readable data comprising the atomic coordinates of Table 3; (ii) a working memory for storing instructions for processing the machine-readable data; and (iii) a central-processing unit coupled to the working memory and to the machine-readable data storage medium for processing the machine readable data into a three-dimensional representation. Preferably a display is also provided that is coupled to the central-processing unit for visualizing the three-dimensional representation of the protein-ligand complex.

Accordingly, it is a principal object of the present invention to provide an active TACE catalytic domain that can form a stable X-ray diffractable crystal.

It is a further object of the present invention to provide a way for exchanging ligands of a TACE catalytic domain in a crystal.

It is a further object of the present invention to provide multiple crystals of the TACE catalytic domain each comprising a different protein-ligand complex.

It is a further object of the present invention to provide an effective way of performing structure based rational drug design with TACE.

It is a further object of the present invention to provide drugs to treat conditions due to an overabundance of the soluble form of TNF-alpha.

These and other aspects of the present invention will be better appreciated by reference to the following drawing and Detailed Description.

DETAILED DESCRIPTION OF THE INVENTION

Figure 1:
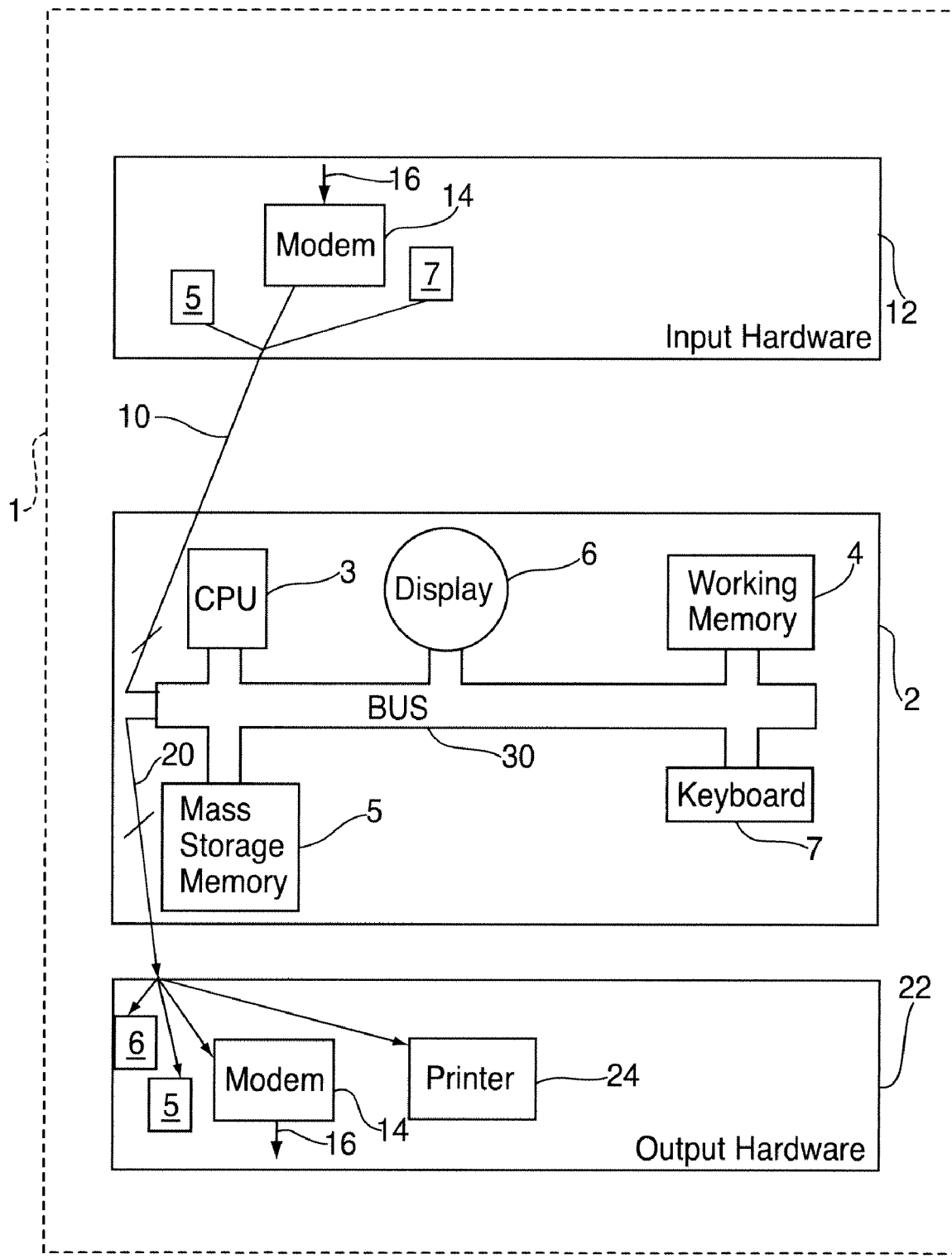
FIG. 1 depicts a schematic of a computer comprising a central processing unit (CPU), a working memory, a mass storage memory, a display terminal, and a keyboard that are interconnected by a conventional bidirectional system bus. The computer can be used to display and manipulate the structural data of the present invention.

Although entirely independent of any particular mechanism, the present invention was conceived following the unexpected discovery by the present inventors that the native TACE protein undergoes autoproteolysis at the high protein concentrations required for X-ray crystallographic analysis. The subsequent identification by the inventors of an autoproteolysis site between $Y_{352}$-$V_{353}$ of SEQ ID NO: 2, raised the possibility that the replacement of either one or both of these amino acid residues might lead to a TACE protein that was resistant to autoproteolysis. Insertion(s) or deletion(s) of amino acid residues adjacent to the $Y_{352}$-$V_{353}$ cleavage site might also lead to a TACE polypeptide that is resistant to autoproteolyisis. However, inserting or deleting amino acid residues adjacent to the $Y_{352}$-$V_{353}$ cleavage site could create conformational changes in the protein that significantly reduce its enzyme activity and/or stability. Similarly, since Tyr352 of SEQ ID NO: 2 is located within a hydrophobic pocket that is close to the active site of the TACE protease, modification of this amino acid residue also might effect the enzymatic activity and/or protein stability. In direct contrast, Val353 of SEQ ID NO: 2 is located on the enzyme surface with its side chain exposed to the solvent, and so modification of the valine side chain might be less traumatic to the enzyme structure. Therefore, modification of Val353 is preferred over either modifying Tyr352, or inserting or deleting amino acid residues adjacent to the $Y_{352}$-$V_{353}$ cleavage site. These latter two alternatives, however, remain part of the present invention.

Indeed, as disclosed herein, substitution of the hydrophobic valine side chain with either serine or glycine significantly reduces autoproteolysis, and dramatically improved the stability of the protein, without significantly altering the proteolytic activity of the TACE enzyme. In a preferred embodiment, the modified TACE catalytic domain contains an amino acid change at amino acid residue 353 of SEQ ID NO: 2. In one such embodiment, Val353 is replaced with a glycyl residue. In another embodiment, Val353 is replaced with a seryl residue. Substitutions of the nonpolar side chain of valine with alternative non-hydrophobic side chains can also prevent auto-proteolysis, and such substitutions are also part of the present invention. In addition, in order to remove N-glycosylation sites it is preferable as exemplified below, that Ser266 be replaced e.g., with an alanyl residue, and Asp452 be replaced e.g., with a glutaminyl residue.

The present invention further provides crystals comprising a protein-ligand complex of a polypeptide that comprises a modified TACE catalytic domain. The three-dimensional structure of a protein-ligand complex comprising a modified TACE catalytic domain bound to N-{3-(hydroxyaminocarbonyl)-1-oxo-(2R)-benzylpropyl}-Ile-Leu-OH is provided in the Example below (see Table 3 which lists the atomic coordinates).

N-{3-(hydroxyaminocarbonyl)-1-oxo-(2R)-benzylpropyl}-Ile-Leu-OH which is commercially available, e.g., from Chem-Impex International, Wood Dale II, (product code 09538), has the following chemical structure:

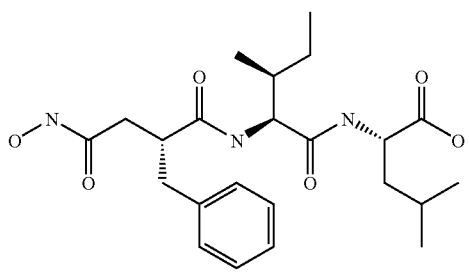

Structure based rational drug design is the most efficient method of drug development. In one common paradigm, a three dimensional structure of a protein-ligand complex is determined, and potential antagonists (e.g., inhibitors) of the protein (e.g., potential drugs) are identified and/or designed with the aid of computer modeling [Bugg et al., *Scientific American*, December: 92-98 (1993); West et al., *TIPS*, 16:67-74 (1995); Dunbrack et al., *Folding & Design*, 2:27-42 (1997)]. The drug candidates are selected and assayed. The most promising drug candidates are identified, and then incubated in excess with crystals of a protein-ligand complex to replace the initial ligand. The three-dimensional structure of the new protein-ligand complex is then determined, and new potential antagonists of the protein are identified and/or designed with the aid of computer modeling. This process can then be continued in successive iterations until a lead drug candidate is identified.

Heretofore, the ability to perform structure based rational drug design with TACE was severely hampered because only two TACE protein-ligands complexes were known to form an X-ray quality crystal, [Maskos et. al., *Proc. Natl. Acad. Sci. USA* 95:3408-3412 (1998); Letavic et al., *Biorgan. & Medic. Chem. Lett.* 12:1387-1390 (2002)], and these crystals were not reported to be capable of ligand exchange. As disclosed herein, the present invention overcomes this problem by providing crystals of the modified TACE catalytic domain that are conducive to ligand exchange.

As used herein the following terms shall have the definitions set out below:

As used herein the term "polypeptide" is used interchangeably with the term "protein" and is further meant to encompass peptides. Therefore, as used herein, a polypeptide is a polymer of two or more amino acids joined together by peptide linkages. Preferably, a polypeptide is a polymer comprising twenty or more amino acid residues joined together by peptide linkages.

As used herein a polypeptide "consisting essentially of" or that "consists essentially of" a specified amino acid sequence is a polypeptide that (i) retains the general characteristics of a polypeptide comprising that amino acid sequence, e.g., the activity of the polypeptide, and (ii) further comprises the identical amino acid sequence, except it consists of plus or minus 10% (or a lower percentage), preferably plus or minus 5% (or a lower percentage), and more preferably plus or minus 2.5% (or a lower percentage) of the amino acid residues.

As used herein a "modified TACE catalytic domain" is a TACE catalytic domain that has been modified to resist and/or prevent autocatalysis. Preferably, at least one of the two critical amino acid residues at the autoproteolytic site of TACE, i.e., Tyr352 and Val353 of SEQ ID NO: 2, has been replaced. More preferably, a modified TACE catalytic domain has the Val353 residue replaced with a non-hydrophobic amino acid residue.

As used herein a "non-hydrophobic amino acid" is an amino acid that is not hydrophobic. The genus of non-hydrophobic amino acids specifically does not include leucine, isoleucine, valine, methionine, tryptophan, and phenylalanine.

As used herein a "polypeptide comprising a modified TACE catalytic domain", can be (i) the full length TACE protein, (ii) a fragment of the TACE protein that includes the modified TACE catalytic domain e.g., the pro and catalytic domain, (iii) the modified TACE catalytic domain alone, or (iv) a chimeric protein which comprises any of the above.

As used herein a "proteolytic polypeptide" of the present invention is a polypeptide that is capable of catalyzing the proteolytic cleavage of a substrate of the native TACE protease. A proteolytic polypeptide of the present invention minimally comprises an active fragment of the TACE catalytic domain that retains proteolytic activity. A proteolytic polypeptide of the present invention can be a chimeric protein.

As used herein an "active fragment" of the catalytic domain of TACE" is a fragment of the catalytic domain of TACE and/or modified TACE catalytic domain that retains at least about 10%, preferably at least about 20%, and more preferably at least about 25% of the proteolytic activity of the full-length TACE protease. Preferably, the active fragment retains at least about 25%, more preferably at least about 50%, and even more preferably at least about 75% of the amino acid residues of the catalytic domain of TACE having the amino acid sequence of SEQ ID NO: 6. More preferably, the amino acid sequence of the active fragment of the TACE catalytic domain has at least about 95% identity to the corresponding amino acid residues of SEQ ID NO: 6.

As used herein the term "chimeric" protein is meant to include "fusion proteins". "Chimeric" proteins of the present invention comprise at least a portion of a non-TACE protein joined via a peptide bond to at least a portion of a TACE polypeptide. Chimeric proteins can have additional structural, regulatory, or catalytic properties. In a particular embodiment the chimeric protein functions as a means of detecting and/or isolating the TACE polypeptide or fragment thereof after the recombinant nucleic acid is expressed. Non-TACE amino acid sequences are preferably either amino- or carboxy-terminal to the TACE sequence.

As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by the TACE polypeptide or the portion of the TACE polypeptide being compared, e.g., the modified catalytic domain (SEQ ID NO: 8). In a preferred embodiment, selected deletions or insertions that could otherwise alter the correspondence between the two amino acid sequences are taken into account.

As used herein, DNA and protein sequence percent identity can be determined using C, MacVector 6.0.1, Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

As used herein a "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. When referring to a nucleic acid that is double stranded both the "sense" strand and the complementary "antisense" strand are intended to be included. Thus a nucleic acid that is hybridizable to SEQ ID NO: 1, for example, can be either hybridizable to the "sense" strand of SEQ ID NO: 1, which is particularly listed in the SEQUENCE LISTING, or to the "antisense" strand which can be readily determined from that SEQUENCE LISTING.

A DNA "coding sequence" is a double-stranded DNA sequence that is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which can then be trans-RNA spliced and translated into the protein encoded by the coding sequence.

A nucleic acid sequence is "operatively linked" to an expression control sequence when the expression control sequence controls or regulates the transcription and translation of that nucleic acid sequence. The term operatively linked includes having an appropriate start signal.

A "heterologous nucleotide sequence" as used herein is a nucleotide sequence that is added to a nucleotide sequence of the present invention by recombinant methods to form a nucleic acid that is not naturally formed in nature. Such nucleic acids can encode chimeric proteins. Alternatively, a heterologous nucleotide sequence can contain a nucleic acid regulatory sequence. Thus a heterologous nucleotide sequence can comprise non-coding sequences including restriction sites, regulatory sites, promoters and the like. In still another embodiment the heterologous nucleotide can function as a means of detecting a nucleotide sequence of the present invention. The present invention provides heterologous nucleotide sequences that when combined with nucleotide sequences encoding the TACE proteins, and fragments thereof, are necessary and sufficient to encode all of the chimeric proteins of the present invention.

As used herein the phrases "structure based rational drug design", "structure based drug design", "structure assisted drug design" and "rational drug design" are used interchangeably. These phrases are meant to convey a particular method of identifying and/or designing a ligand (preferably an inhibitor) for a specific target protein that includes the use of the three-dimensional structure of that protein and/or its corresponding protein-ligand complex.

The phrase "binding to" in regard to a ligand binding to a polypeptide is used herein to include any or all such specific interactions that lead to a protein-ligand binding complex. This can include processes such as covalent, ionic, hydrophobic and hydrogen bonding, but does not include non-specific associations such solvent preferences.

As used herein a "ligand" of a polypeptide is a compound that binds to the polypeptide in a protein-ligand binding complex. In a specific embodiment of the present invention the polypeptide has an enzymatic activity and the ligand inhibits that activity when bound to the polypeptide in a protein-ligand binding complex. Such a ligand is also termed an "inhibitor".

As used herein the term "initial ligand" denotes a ligand in a protein-ligand complex that is, or can be displaced by a "substitute ligand".

As used herein, a "protein-ligand binding complex" is a specific association between a polypeptide and the compound that binds to it. In a preferred embodiment of the present invention, the ligand is an inhibitor of the polypeptide. In a particular embodiment of this type, the binding of the inhibitor to the polypeptide occurs at the active site of the polypeptide.

As used herein "incubating a ligand with a crystal" is used interchangeably with "soaking a crystal with a ligand". Incubating a ligand with a crystal is the contacting of a ligand with a crystal of a polypeptide under the appropriate conditions and for a sufficient time period (e.g., hours to several days) for the ligand to bind to the crystalline polypeptide and form a crystalline protein-ligand complex. Such incubating can further and/or alternatively, include contacting an excess of a substitute ligand with a crystal of a protein-ligand complex under the appropriate conditions and for a sufficient time period (e.g., hours to several days) for the substitute ligand to replace the initial ligand and form the new crystalline protein-ligand complex.

As used herein the terms "displacing", "replacing", and "exchanging" are used interchangeably in regard to the substitution of one ligand in a protein-ligand complex for another.

As used herein an "excess of a substitute ligand" is an amount of that ligand that is sufficient to replace 80% or more, and preferably 90% or more, of the initial ligand in a protein-ligand complex. In a particular embodiment of this type, the concentration of the substitute ligand is about ten-fold higher than the concentration of the protein-ligand complex. In a preferred embodiment, the concentration of the substitute ligand is about one hundred-fold higher than the concentration of the protein-ligand complex.

As used herein the term "X-ray diffractable crystal" is a crystal of a compound that yields a discernable diffraction pattern when subjected to 0.5 to 2.5 Å incident X-ray radiation.

As used herein an "X-ray quality crystal" is an X-ray diffractable crystal that can yield meaningful structural data of its crystalline composition when subjected to X-ray crystallographic analysis.

As used herein, and unless otherwise specified, the terms "agent", "potential drug", "compound", or "test compound" are used interchangeably, and refer to chemicals that have or potentially have a use as an inhibitor of the proteolytic activity of TACE. Preferably such agents include drugs for the treatment or prevention of a disease and/or condition involving the proteolytic action of TACE. Therefore, such agents may be used, as described herein, in drug assays and drug screens and the like.

As used herein a "small organic molecule" is an organic compound [or organic compound complexed with an inorganic compound (e.g., metal)] that has a molecular weight of less than 3 Kd.

As used herein the terms "approximately" and "about" are used to signify that a value is within twenty percent of the indicated value i.e., an amino acid sequence containing "approximately" 260 amino acid residues can contain between 208 and 312 amino acid residues.

Nucleic Acids Encoding TACE

Obtaining and/or constructing a cDNA that encodes a polypeptide comprising a modified TACE facilitates the production of the large quantities of protein required to perform X-ray crystallographic analysis. Since the sequence of the native protein is known [see U.S. Pat. No. 6,013,466, Issued Jan. 11, 2000, the contents of which are hereby incorporated by reference in their entireties], a cDNA encoding the modified protease can be readily obtained.

To express a recombinant protein of the present invention in a host cell, an expression vector can be constructed comprising the corresponding cDNA. The present invention therefore, provides expression vectors containing nucleic acids encoding polypeptides comprising the modified TACE catalytic domains of the present invention. Due to the degeneracy of nucleotide coding sequences, other DNA sequences which encode substantially the same amino acid sequence as a nucleic acid encoding a polypeptide comprising the modified TACE catalytic domain of the present invention may be used in the practice of the present invention. These include, but are not limited to, allelic genes, homologous genes from other species, which are altered by the substitution of different codons that encode the same amino acid residue within the sequence, thus producing a silent change. Host cells comprising the expression vectors of the present invention are also provided.

Cloning of cDNAs and expression of their corresponding recombinant proteins have become a routine laboratory exercise [see Sambrook and Russell, *Molecular Cloning, A laboratory Manual*, 3$^{rd}$ edition, Cold Spring Harbor Laboratory Press, Cold Spring Harbor L.I. (2000), the contents of which are hereby incorporated by reference in their entireties]. The use of a Baculovirus recombination system and Sf9 host cells is exemplified below. Purification of recombinant proteins has also become a routine laboratory exercise. In the present case, the modified TACE protein was cloned and expressed as the pro-protein. The pre and pro domains were cleaved during protein expression and secretion by the cells. The catalytic domain was then purified (see Example below).

The nucleotide sequence for open reading frame of TACE with a GS linker, a polyHis tag (H6), and stop codon is shown below. The nucleic acid sequence encoding: (i) the pre domain is underlined, (ii) the pro domain is under-dashed, (iii) the catalytic domain is unmarked and (iv) the GS linker and the polyHis tag (H6) are double underlined. The stop codon is underlined with a wavy line.

(SEQ ID NO: 9)

ATGAGGCAGTCTCTCCTATTCCTGACCAGCGTGGTTCCTTTCGTGCTGGCGCCGCGACCT

CCGGATGACCCGGGCTTCGGCCCCCACCAGAGGCTCGAGAAGCTTGATTCTTTGCTCTCA

GACTACGATATTCTCTCTTTATCTAATATCCAGCAGCATTCGGTAAGAAAAAGAGATCTA

CAGACTTCAACACATGTAGAAACACTACTAACTTTTTCAGCTTTGAAAAGGCATTTTAAA

TTATACCTGACATCAAGTACTGAACGTTTTTCACAAAATTTCAAGGTCGTGGTGGTGGAT

GGTAAAAACGAAAGCGAGTACACTGTAAAATGGCAGGACTTCTTCACTGGACACGTGGTT

GGTGAGCCTGACTCTAGGGTTCTAGCCCaCATAAGAGATGATGATGTTATAATCAGAATC

-continued

```
AACACAGATGGGGCCGAATATAACATAGAGCCACTTTGGAGATTTGTTAATGATACCAAA

GACAAAAGAATGTTAGTTTATAAATCTGAAGATATCAAGAATGTTTCACGTTTGCAGTCT

CCAAAAGTGTGTGGTTATTTAAAAGTGGATAATGAAGAGTTGCTCCCAAAAGGGTTAGTA

GACAGAGAACCACCTGAAGAGCTTGTTCATCGAGTGAAAAGAAGAGCTGACCCAGATCCC

ATGAAGAACACGTGTAAATTATTGGTGGTAGCAGATCATCGCTTCTACAGATACATGGGC

AGAGGGGAAGAGAGTACAACTACAAATTACTTAATAGAGCTAATTGACAGAGTTGATGAC

ATCTATCGGAACACTGCATGGGATAATGCAGGTTTTAAAGGCTATGGAATACAGATAGAG

CAGATTCGCATTCTCAAGTCTCCACAAGAGGTAAAACCTGGTGAAAAGCACTACAACATG

GCAAAAAGTTACCCAAATGAAGAAAAGGATGCTTGGGATGTGAAGATGTTGCTAGAGCAA

TTTAGCTTTGATATAGCTGAGGAAGCATCTAAAGTTTGCTTGGCACACCTTTTCACATAC

CAAGATTTTGATATGGGAAcTCtTGGATTAGCTTATGTTGGCTCTCCCAGAGCAAACAGC

CATGGAGGTGTTTGTCCAAAGGCTTATTATAGCCCAGTTGGGAAGAAAAATATCTATTTG

AATAGTGGTTTGACGAGCACAAAGAATTATGGTAAAACCATCCTTACAAAGGAAGCTGAC

CTGGTTACAACTCATGAATTGGGACATAATTTTGGAGCAGAACATGATCCGGATGGTCTA

GCAGAATGTGCCCCGAATGAGGACCAGGGAGGGAAATATGTCATGTATCCCATAGCTGTG

AGTGGCGATCACGAGAACAATAAGATGTTTTCACAGTGCAGTAAACAATCAATCTATAAG

ACCATTGAAAGTAAGGCCCAGGAGTGTTTTCAAGAACGCAGCAATAAAGTTGGGAGCCAC

CATCATCACCATCACTAA
```

Any technique for mutagenesis known in the art can be used to convert the native TACE catalytic domain to a modified domain, including but not limited to, in vitro site-directed mutagenesis [Hutchinson et al., *J. Biol. Chem.*, 253:6551 (1978); Zoller and Smith, *DNA*, 3:479-488 (1984); Oliphant et al., *Gene*, 44:177 (1986); Hutchinson et al., *Proc. Natl. Acad. Sci. U.S.A.*, 83:710 (1986)]. The use of TAB@ linkers (Pharmacia), etc. and PCR techniques also can be employed for site directed mutagenesis [see Higuchi, "Using PCR to Engineer DNA", in PCR Technology: Principles and Applications for DNA to Amplification, H. Erlich, ed, Stockton Press, Chapter 6, pp. 61-70 (1989)]. Preferably mutagenesis (i.e., modification) of the TACE catalytic domain is performed in a two step process [Wang, and Malcolm, *BioTechniques* 26:680-682 (1999)]. In the Example below, two extension reactions were performed in separate tubes in the first stage: (i) one containing the forward primer, and (ii) the other containing the reverse primer. After two cycles, the two reactions are mixed and the standard QuickChange mutagenisis procedure is carried out for an additional 18 cycles. Following amplification, the parental strand is digested with 1Unit of Dpn1 for 1 hour and an aliquot is transformed into DH5-alpha cells [GeneWiz, New York, N.Y.]

The TACE Polypeptide

The amino acid sequence for the TACE polypeptide is shown below. (i) The pre domain is underlined, (ii) the pro domain is under-dashed, and (iii) the catalytic domain is unmarked. The GS-linker and polyhistidine tag (H6) are not included. The valine residue that is replaced with a non-hydrophobic amino acid residue in the modified TACE polypeptide is in bold. In addition, serine-266 has been replaced by an alanine, and asparagine-452 has been replaced by a glutamine in order to remove the N-linked glycosylation sites.

(SEQ ID NO: 2)

MRQSLLFLTSVVPFVLAPRPPDDPGFGPHQRLEKLDSLLSDYDILSLSNIQQHSVRKRDL

QTSTHVETLLTFSALKRHFKLYLTSSTERFSQNFKVVVVDGKNESEYTVKWQDFFTGHVV

GEPDSRVLAHIRDDDVIIRINTDGAEYNIEPLWRFVNDTKDKRMLVYKSEDIKNVSRLQS

PKVCGYLKVDNEELLPKGLVDREPPEELVHRVKRRADPDPMKNTCKLLVVADHRFYRYMG

RGEESTTTNYLIELIDRVDDIYRNTAWDNAGFKGYGIQIEQIRILKSPQEVKPGEKHYNM

AKSYPNEEKDAWDVKMLLEQFSFDIAEEASKVCLAHLFTYQDFDMGTLGLAYVGSPRANS

HGGVCPKAYYSPVGKKNIYLNSGLTSTKNYGKTILTKEADLVTTHELGHNFGAEHDPDGL

AECAPNEDQGGKYVMYPIAVSGDHENNKMFSQCSKQSIYKTIESKAQECFQERSNKV

The amino acid sequence for the catalytic domain of the modified TACE polypeptide is shown below. Whereas, the native protein comprises $VAL_{353}$ ($VAL_{139}$ of SEQ ID NO: 6), this amino acid residue is replaced by a non-hydrophobic amino acid residue in a modified TACE catalytic domain. This amino acid position is denoted with an "X" in bold below. Preferably the non-hydrophobic amino acid residue is a glycl, alanyl, or seryl amino acid residue. The GS-linker and Polyhistidine tag (H6) are not included.

RADPDPMKNTCKLLVVADHRFYRYMGRGEESTTTNYLIELIDRVDDIY

RNTAWDNAGFKGYGIQIEQIRILKSPQEVKPGEKHYNMAKSYPNEEKD

AWDVKMLLEQFSFDIAEEASKVCLAHLFTYQDFDMGTLGLAYXGSPRA

NSHGGVCPKAYYSPVGKKNIYLNSGLTSTKNYGKTILTKEADLVTTHE

LGHNFGAEHDPDGLAECAPNEDQGGKYVMYPIAVSGDHENNKMFSQCS

KQSIYKTIESKAQECFQERSNKV (SEQ ID NO: 8), where X is a non-hydrophobic amino acid residue, and preferably either alanine, glycine or serine.

In a particular embodiment of the present invention, a modified TACE polypeptide or fragment thereof (e.g., the catalytic domain) is at least about 75% identical, more preferably at least about 90% identical, and most preferably at least about 95% identical to the TACE polypeptide or fragment thereof. As indicated above, a modified TACE or fragment thereof has a non-hydrophobic amino acid residue in place of the valine at position 353 (as defined in SEQ ID NO: 2).

Polypeptides comprising the modified TACE catalytic domains of the invention include those containing altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs.

For example, the nonpolar amino acids include alanine, leucine, isoleucine, valine, proline, phenylalanine, tryptophan, and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine and lysine. The negatively charged (acidic) amino acids include aspartic acid and glutamic acid.

Particularly preferred conserved amino acid exchanges are:

(a) Lys for Arg or vice versa such that a positive charge may be maintained;

(b) Glu for Asp or vice versa such that a negative charge may be maintained;

(c) Ser for Thr or vice versa such that a free —OH can be maintained;

(d) Gln for Asn or vice versa such that a free $NH_2$ can be maintained; and (e) Ile for Leu or for Val or vice versa as roughly equivalent hydrophobic amino acids.

All of the modified TACE catalytic domains of the present invention also can be part of a chimeric protein. In a specific embodiment, a chimeric TACE protein is expressed in a eukaryotic cell. Such a chimeric protein can be a fusion protein used to isolate a modified TACE of the present invention, through the use of an affinity column that is specific for the protein fused to the TACE protein. In one such embodiment, the chimeric TACE is expressed in a eukaryotic cell. Examples of such fusion proteins include: a glutathione-S-transferase (GST) fusion protein, a maltose-binding (MBP) protein fusion protein, a FLAG-tagged fusion protein, or as specifically exemplified below, a poly-histidine-tagged fusion protein.

Expression of a chimeric TACE protein, or fragment thereof, as a fusion protein can facilitate stable expression, and/or allow for purification based on the properties of the fusion partner. Thus the purification of the recombinant polypeptides of the present invention can be simplified through the use of fusion proteins having affinity tags. For example, GST binds glutathione conjugated to a solid support matrix, MBP binds to a maltose matrix, and poly-histidine chelates to a NI-chelation support matrix, as specifically exemplified below [see Hochuli et al., *Biotechnology* 6:1321-1325 (1998)]. The fusion protein can be eluted from the specific matrix with appropriate buffers, or by treating with a protease that is specific for a cleavage site that has been genetically engineered in between the TACE protein and its fusion partner. Alternatively, a modified TACE catalytic domain can be combined with a marker protein such as green fluorescent protein [Waldo et al., *Nature Biotech.* 17:691-695 (1999); U.S. Pat. No. 5,625,048 filed Apr. 29, 1997 and WO 97/26333, published Jul. 24, 1997, the contents of which are hereby incorporated by reference herein in their entireties].

Alternatively or in addition, other column chromatography steps (e.g., gel filtration, ion exchange, affinity chromatography etc.) can be used to purify the recombinant proteins of the present invention. In many cases, such column chromatography steps employ high performance liquid chromatography or analogous methods in place of the more classical gravity-based procedures.

As exemplified below, a recombinant modified TACE catalytic domain was purified with a NiNTA column following routine centrifugation and diafiltration steps. After the purified protein was collected from the NiNTA column, it was placed on a gel filtration column. The resulting eluate was then concentrated and desalted prior to being combined with an inhibitor to form a protein-ligand complex.

Alternatively, polypeptides comprising the modified TACE catalytic domains of the present invention can be chemically synthesized [see e.g., Synthetic Peptides: *A User's Guide*, W.H. Freeman & Co., New York, N.Y., pp. 382, Grant, ed. (1992)].

Enzyme Assays

The catalytic activity of the TACE protease can be determined in an assay using the synthetic peptide Ac-SPLAQA-VRSSSR-$NH_2$(SEQ ID NO: 17) as the substrate. This amino acid sequence corresponds to the cleavage site of TACE on proTNF-alpha, with the sessile bond being between the alanine and the valine. The activity can be measured by incubating 100 nM TACE with 100 micromolar substrate in 25 mM HEPES pH 7.3, 5 mM $CaCl_2$, for 1 hour at room temperature. Product formation can be quantified at 214 nm by HPLC using a reverse phase column to separate the substrate from the products. The ability of a given compound added to the reaction to act as an inhibitor of TACE can then be determined.

Alternatively, TACE activity can be determined in a fluorescence assay using the synthetic peptide substrate, K(Mca)-SPLAQA-VRSSSRK(Dpn)-NH$_2$ (SEQ ID NO: 18). K(Mca) is a lysyl residue modified by comprising an epsilonN-methoxycoumarin, whereas K(Dpn)-NH$_2$ is a lysyl residue modified to comprise an epsilonN 2,4, dinitrophenyl. 2-100 nanomolar TACE protease (or active fragment thereof) is incubated with 25 micromolar peptide substrate in 25 mM HEPES pH 7.3, 5 mM CaCl$_2$ for 1 hour at room temperature. Product formation is detected by exciting at 340 nm and measuring the fluorescence emission at 380 nm every 30 seconds for about an hour. The initial velocity can be obtained by linear regression. The increase in fluorescence emission can be correlated with the quantity of cleaved product. The ability of a given compound added to the reaction to act as an inhibitor of TACE can then be determined.

Crystallization

Crystals of the protein-ligand complex comprising a modified TACE catalytic domain of the present invention can be grown by a number of techniques including batch crystallization, vapor diffusion (e.g., by sitting drop or hanging drop) and by microdialysis. In the Example below, the modified TACE catalytic domain was complexed with N-{D,L-2-(hydroxyaminocarbonyl)methyl-4-methylpentanoyl}-L-3-amino-2-dimethylbutanoyl-L-alanine, 2-(amino)ethyl amide and crystallized by hanging drop vapor diffusion. Seeding of the crystals in some instances is required to obtain X-ray quality crystals. Standard micro and/or macro seeding of crystals may therefore be used.

As exemplified below, the protein-ligand complex comprising the modified TACE catalytic domain V353G (vgTACE) was crystallized under similar conditions to those previously employed for the non-modified TACE [WO9940182, Published Aug. 12, 1999, U.S. application Ser. No. 09/117,476, filed Jan. 27, 1999, the contents of which are both hereby incorporated by reference in its entireties].

A substitute ligand can replace the co-crystallized initial ligand by soaking a crystal of protein-initial ligand complex with the substitute ligand. Thus, one or more crystals of protein-initial ligand complex can be placed in the reservoir solution containing about a 10-fold or greater excess of substitute ligand. The crystal is kept under the appropriate conditions and for a sufficient time period for the substitute ligand to replace the initial ligand and form the new crystalline protein-substitute ligand complex. In the example below, a crystal was kept in the solution containing the substitute ligand for about 72 hours. After the incubation, the crystal of the protein-substitute ligand complex can be frozen in liquid propane, for example and then used for X-ray diffraction.

Crystals can be characterized using X-rays produced in a conventional source (such as a sealed tube or a rotating anode) or using a synchrotron source. Methods of characterization include, but are not limited to, precision photography, oscillation photography and diffractometer data collection. As exemplified below, the crystals were flash frozen in liquid propane and X-ray diffraction was collected at 100 degrees Kelvin using conventional or synchrotron sources.

In the Example below, the crystal structure of the modified TACE catalytic domain V353G (vgTACE) was solved by molecular replacement and then refined using standard crystallographic programs. The published TACE structure was used as the starting model [PDB code:1BKC; Maskos et. al., *Proc. Natl. Acad. Sci. USA* 95:3408-3412 (1998); WO9940182, Published Aug. 12, 1999, U.S. application Ser. No. 09/117,476, filed Jan. 27, 1999, the contents of which are both hereby incorporated by reference in its entirety]. Replacement of the co-crystallized inhibitor was verified by difference electron density maps. The vgTACE:inhibitor structures were refined using X-PLOR [Brunger et al., *Acta Crystallogr. A* 46:585-593 (1990); Brunger et al., *Acta Crystallogr. D Biol. Crystallogr.*, 54:905-921 (1998)].

Refinement calculations also can be performed using CNS [Adams et al., *Proc. Natl. Acad. Sci. USA*, 94:5018-5023 (1997)]. Map interpretation and model building also can be performed using O [Jones et al., *Acta Cryst, A* 47:110-119 (1991)]. Other computer programs that can be used to solve crystal structures include: QUANTA, CHARMM; INSIGHT; SYBYL; MACROMODE; and ICM.

Generally, structure based rational drug design is performed by analyzing the three-dimensional structures of successive protein-ligand complexes. This iterative process requires X-ray quality crystals of numerous protein-ligand complexes. These crystals can be obtained three ways. First, crystals of each protein-ligand complex can be grown de novo. This is the most time-consuming method, and in many instances requires determining a new set of crystallization conditions. The second method is to incubate (e.g., soak) individual crystals of the uncomplexed protein with each different ligand. This method is much faster than growing new crystals, but still requires a relatively large stock of protein to generate all of the new crystals. The third and most expedient method is to incubate a previously formed protein-ligand crystal with a large excess of a substitute ligand, thereby replacing the initial ligand with the substitute ligand in the protein-ligand complex. Heretofore, it was difficult to prepare alternative protein-ligand complexes of TACE since the two available X-ray quality crystals of TACE comprised the unstable, native TACE. The present invention overcomes this problem by providing a modified TACE catalytic domain that forms X-ray quality crystals that are amenable to ligand exchange.

Structure Based Rational Drug Design

Once three-dimensional structures of crystals comprising modified TACE catalytic domains are determined, a potential inhibitor of TACE can be examined through the use of computer modeling using a docking program such as GRAM, DOCK, or AUTODOCK [Dunbrack et al., *Folding & Design*, 2:27-42 (1997)]. This procedure can include computer fitting of potential inhibitors to the modified TACE catalytic domain to ascertain how well the shape and the chemical structure of the potential modulator will interact with the TACE protein [Bugg et al., *Scientific American*, December:92-98 (1993); West et al., *TIBS*, 16:67-74 (1995)]. Computer programs can also be employed to estimate the attraction, repulsion, and steric hindrance of the modified TACE catalytic domain with an inhibitor.

Generally the tighter the fit, the lower the steric hindrances, and the greater the attractive forces, the more potent the inhibitor, since these properties are consistent with a tighter binding constant. Furthermore, the more specificity in the design of a potential drug the more likely that the drug will not interact as well with other proteins. This will minimize potential side-effects due to unwanted interactions with other proteins.

Initially compounds known to bind TACE, for example N-{D,L-2-(hydroxyaminocarbonyl)methyl-4-methylpentanoyl}-L-3-amino-2-dimethylbutanoyl-L-alanine, 2-(amino)ethyl amide, or a compound that inhibits TACE disclosed by Letavic et al., [*Biorgan. & Medic. Chem. Lett.* 12:1387-1390 (2002) the contents of which are hereby incorporated by reference in their entireties], or alternatively, a compound that binds metalloproteases as disclosed as by Zask et al. [*Curr. Pharm. Des.,* 2:624-661 (1996), the contents of which are hereby incorporated by reference in their entireties], can be systematically modified by computer modeling programs until one or more promising potential analogs are identified. Such analysis has been shown to be effective in the development of HIV protease inhibitors [Lam et al., *Science* 263:380-384 (1994); Wlodawer et al., *Ann. Rev. Biochem.* 62:543-585 (1993); Appelt, *Perspectives in Drug Discovery and Design* 1:23-48 (1993); Erickson, *Perspectives in Drug Discovery and Design* 1:109-128 (1993)]. Alternatively, a potential inhibitor initially can be obtained by screening a random peptide library or a chemical library. In the former case, a random peptide library can be produced by recombinant bacteriophage, for example, [Scott and Smith, *Science,* 249:386-390 (1990); Cwirla et al., *Proc. Natl. Acad. Sci.,* 87:6378-6382 (1990); Devlin et al., *Science,* 249:404-406 (1990)]. A peptide selected in this manner would then be systematically modified by computer modeling programs, as described above.

If a potential inhibitor is a small organic compound, it can be selected from a library of chemicals, including commercially available chemical libraries. Alternatively, the small organic compound may be synthesized de novo. The de novo synthesis of one or even a relatively small group of specific compounds is reasonable in the art of drug design. Once obtained, the potential inhibitor can be further tested in a standard binding and/or catalytic assay with TACE, the TACE catalytic domain, or an active fragment thereof.

For example, a binding assay can be performed following the attachment of the TACE catalytic domain to a solid support. Methods for placing the TACE catalytic domain on the solid support are well known in the art and include such things as linking biotin to the TACE catalytic domain and linking avidin to the solid support. The solid support can be washed to remove unbound protein. A solution of a labeled potential inhibitor can be contacted with the solid support. The solid support is washed again to remove the potential inhibitor not bound to the support. The amount of labeled potential inhibitor remaining with the solid support, and thereby bound to the TACE catalytic domain can be determined. Alternatively, or in addition, the dissociation constant between the labeled potential inhibitor and the TACE catalytic domain, for example, can be determined. Suitable labels for either the TACE catalytic domain or the potential inhibitor include, radioactive labels (e.g., $^{14}C$, $^{1}H$,) and fluorescent labels such as fluorescein isothiocyanate (FITC).

In another embodiment, a Biacore machine can be used to determine the binding constant of the TACE catalytic domain with a potential inhibitor [O'Shannessy et al. *Anal. Biochem.* 212:457-468 (1993); Schuster et al., *Nature* 365:343-347 (1993)]. In another aspect of the present invention a potential inhibitor is tested for its ability to inhibit the proteolytic activity of TACE or an active fragment thereof. An inhibitor is then selected on the basis of its ability to inhibit the catalytic reaction of the TACE protease.

When a promising inhibitor is identified, a crystal comprising a protein-ligand complex of the inhibitor and the modified TACE catalytic domain can be prepared by incubating an excess of the inhibitor (substitute ligand) with a crystal of a modified TACE catalytic domain-ligand complex. The three-dimensional structure of the resulting crystalline protein-substitute ligand complex can then be determined by molecular replacement analysis, for example.

Molecular replacement involves using a known three-dimensional structure as a search model to determine the structure of a closely related molecule or protein-ligand complex in a different crystalline form. The measured X-ray diffraction properties of the new crystal are compared with the search model structure to compute the position and orientation of the protein in the new crystal. Computer programs that can be used include: X-PLOR (see above), CNS, (Crystallography and NMR System, a next level of XPLOR), and AMORE [Navaza, Acta Crystallographics ASO, 157-163 (1994)]. Once the position and orientation are known, an electron density map can be calculated using the search model to provide X-ray phases. Thereafter, the electron density is inspected for structural differences and the search model is modified to conform to the new structure. Using this approach, it is possible to solve the three-dimensional structures of crystals of any protein-ligand complex of the modified TACE catalytic domain.

For all of the drug screening assays described herein, further refinements to the structure of the drug will generally be necessary and can be made by the successive iterations of any and/or all of the steps provided by the particular drug screening assay and/or in combination with other such drug screening assays.

A candidate drug selected by performing structure based rational drug design can then be assayed in situ and/or in vivo. A candidate drug can be identified as a drug, for example, if it ameliorates a symptom caused by an overabundance of the soluble form of TNF-alpha in an animal model. Indeed, methods of testing such potential candidate drugs in animal models are well known in the art. The potential drugs can be administered by a variety of ways including topically, orally, subcutaneously, or intraperitoneally depending on the proposed use. Generally, at least two groups of animals are used in the assay, with at least one group being a control group that is administered the administration vehicle without the potential drug.

Electronic Representation of the Three Dimensional Structure of TACE

The present invention provides the three-dimensional depiction of the TACE catalytic domain in a complex with an inhibitor on an electronic and/or magnetic medium. More specifically, the present invention provides the data comprised in Table 3 on an electronic and/or magnetic medium. In addition, the present invention provides a computer that comprises a representation of the TACE catalytic domain-inhibitor complex in computer memory that can be used to screen for compounds that will inhibit the proteolytic activity of TACE. The computer may comprise portions of, or all of the information contained in Table 3. In a particular embodiment, the computer comprises: (i) a machine-readable data storage material encoded with machine-readable data, (ii) a working memory for storing instructions for processing the machine readable data, (iii) a central processing unit coupled to the working memory and the machine-readable data storage material for processing the machine readable data into a three-dimensional representation, and (iv) a display coupled to the central processing unit for displaying the three-dimensional representation. Thus the machine-readable data storage medium comprises a data storage material encoded with machine readable data which can comprise portions of, or all of the structural information contained in Table 3.

One embodiment for manipulating and displaying the structural data provided by the present invention is schematically depicted in FIG. 1. As depicted the System 1, includes a computer 2 comprising a central processing unit ("CPU")3, a working memory 4 which may be random-access memory or "core" memory, mass storage memory 5 (e.g., one or more disk or CD-ROM drives), a display terminal 6 (e.g., a cathoderay tube), one or more keyboards 7, one or more input lines 10, and one or more output lines 20, all of which are interconnected by a conventional bidirectional system bus 30.

Input hardware 12, coupled to the computer 2 by input lines 10, may be implemented in a variety of ways. Machine-readable data may be inputted via the use of one or more modems 14 connected by a telephone line or dedicated data line 16. Alternatively or additionally, the input hardware may comprise CD-ROM or disk drives 5. In conjunction with the display terminal 6, the keyboard 7 may also be used as an input device. Output hardware 22, coupled to computer 2 by output lines 20, may similarly be implemented by conventional devices. Output hardware 22 may include a display terminal 6 for displaying the three dimensional data. Output hardware might also include a printer 24, so that a hard copy output may be produced, or a disk drive or CDROM 5, to store system output for later use, [see also U.S. Pat. No. 5,978,740, Issued Nov. 2, 1999, the contents of which are hereby incorporated by reference in their entireties].

In operation, the CPU 3 (i) coordinates the use of the various input and output devices 12 and 22; (ii) coordinates data accesses from mass storage 5 and accesses to and from working memory 4; and (iii) determines the sequence of data processing steps. Any of a number of programs may be used to process the machine-readable data of this invention.

TABLE 1

TABLE OF SEQUENCES

| SEQ ID NO: | Type | Description |
|---|---|---|
| 1 | N.A. | Pre, Pro, and Catalytic domain |
| 2 | A.A. | Pre, Pro, and Catalytic domain |
| 3 | N.A. | Pro and Catalytic domain |
| 4 | A.A. | Pro, and Catalytic domain |
| 5 | N.A. | Catalytic domain |
| 6 | A.A. | Catalytic domain |
| 7 | N.A. | Catalytic domain (modified) |
| 8 | A.A. | Catalytic domain (modified) |
| 9 | N.A. | open reading frame |
| 10 | N.A. | BamH1f primer |
| 11 | N.A. | Kpn1r primer |
| 12 | N.A. | V353Gf primer |
| 13 | N.A. | V353Gr primer |
| 14 | N.A. | V353Sf primer |
| 15 | N.A. | V353Sr primer |
| 16 | A.A | internal cleave site |
| 17 | A.A | synthetic TACE substrate |
| 18 | A.A | synthetic TACE substrate |
| 19 | N.A. | vgTACE |
| 20 | A.A | vgTACE |

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

Material and Methods

Cloning of TACE and TACE Mutants:

The TACE protein was cloned and expressed as the pro-protein. The pre and pro domains are cleaved during protein expression and secretion by the cells. Only the catalytic domain was purified.

Two PCR primers were used to amplify the pre-pro-cat domains of TACE having BamH1 and GS-(His)-6-Kpn1 sites at the 5' and 3' ends respectively:

```
                                                  SEQ ID NO: 10
BamH1f:  5' cgcggatccatgaggcagtctctcctattcctg 3'

SEQ ID NO: 11
Kpn1r:   5' ccggcctaccttagtgatggtgatgatggtgggatc 3'
```

The purified PCR fragment was digested with BamH1 and Kpn1 and subcolned into the pFastBac1 vector provided in the Bac-to-Bac Baculovirus expression system (Invitrogen, Carlsbad, Calif.). The TACE mutants (V353G, V353S) were generated using the QUICKCHANGE kit (Stratagene, La Jolla, Calif., USA) using the native TACE pFastBac1 vector as a template and the following complementary mutagenic primers:

```
V353Gf: SEQ ID NO: 12
5' GGA ACT CTT GGA TTA GCT TAT GGA GGC TCT CCC AGA
GCA AAC 3'

V353Gr: SEQ ID NO: 13
5' GTT TGC TCT GGG AGA GCC TCC ATA AGC TAA TCC AAG
AGT TCC 3'

V353Sf: SEQ ID NO: 14
5' GGA ACT CTT GGA TTA GCT TAT AGC GGC TCT CCC AGA
GCA AAC 3'

V353Sr: SEQ ID NO: 15
5' GTT TGC TCT GGG AGA GCC GCT ATA AGC TAA TCC AAG
AGT TCC 3'
```

The mutagenesis was performed in two steps as previously described [Wang, and Malcolm, BioTechniques 26:680-682 (1999) the contents of which are hereby incorporated by reference in their entireties]. In the first stage, two extension reactions were performed in separate tubes; one containing the forward primer and the other containing the reverse primer. After two cycles, the two reactions were mixed and the standard QUICKCHANGE mutagenisis procedure was carried out for an additional 18 cycles. Following amplification, the parental strand was digested with 1 Unit of Dpn1 for 1 hour and an aliquot was transformed into DH5-alpha cells. The sequences of all of the vectors were confirmed. (GeneWiz, New York, N.Y.)

Production of Recombinant Baculovirus: Recombinant baculovirus was produced using the BAC-TO-BAC expression system (Invitrogen, Carlsbad, Calif.) following known protocols for the transposition, isolation and transfection of recombinant bacmid DNA into Sf9 cells for production of viral particles. The virus was amplified to the P2 generation and was titered using the BacPAC Baculovirus Rapid Titer Kit (Clonetech, Palo Alto, Calif.).

Expression and Purification of TACE and TACE mutants: Logarithmically growing *Trichoplusia Ni* cells (High5™ cells, 2×10⁶ cells/ml) were infected with amplified baculovirus at a MOI=1.0 (2.5×10⁸ pfu/ml) and grown at 27 degrees Celsius for 48-60 hours. Secreted TACE was isolated from the cell culture media after clarification by centrifugation. The pooled supernatants were concentrated 10 fold and the buffer exchanged into 25 mM HEPES, 0.15M NaCl, pH 7.5 by diafiltration. To the desalted supernatant, 4-aminophenylmercuric acetate (APMA) was added to 20 µM, lauryl maltoside to 0.05%, and imidazole to 25 mM. The supernatant was then applied to a NiNTA column (Qiagen Hilden, Germany). The NiNTA column was washed with 25 mM imidazole in buffer A (50 mM HEPES, 10% glycerol, 0.3M NaCl, 0.1% m-octyl-Beta-D-glucopyranoside, pH 7.5) until a stable baseline was achieved. The protein was then eluted with 250 mM imidazole in buffer A. The eluted protein was diluted to 0.1 mg/ml and dialyzed overnight against 25 mM Tris pH 7.5, with 20 µM APMA to digest excess pro-domain. The protein was collected and adjusted to 0.15M NaCl, concentrated, and applied to a SUPERDEX-75 gel filtration column (Pharmacia) equilibrated with 25 mM Tris-HCl, 0.2M NaCl pH 7.5 at 4 degrees Celsius. Fractions corresponding to the monomer of TACE were pooled, and stored at 4 degrees Celsius. The pooled TACE enzyme was concentrated to 15 mg/ml, desalted into 25 mM Tris-HCl pH 7.5 using BIO-SPIN 6 columns (Bio-Rad, Hercules, Calif.) and immediately complexed with N-{D,L-2-(hydroxyaminocarbonyl)methyl-4-methylpentanoyl}-L-3-amino-2-dimethylbutanoyl-L-alanine, 2-(amino)ethyl amide at a 1:1.5 molar ratio. Using this protocol, total expression levels of 5-10 mg/L were obtained with a final recovery of 0.5-5 mg/L.

Crystallization: Crystals were obtained by the hanging drop vapor diffusion method [Ducruix and Giege. Crystallization of Nucleic Acids and Proteins. A practical approach. Oxford University Press, (1992)]. A small volume (1 to 15 microliters) containing the N-{D,L-2-(hydroxyaminocarbonyl)methyl-4-methylpentanoyl}-L-3-amino-2-dimethylbutanoyl-L-alanine, 2-(amino)ethyl amide [commercially available from e.g., CALBIOCHEM, San Diego Calif., Catalogue No. 579052, (TAPI-2)] solution was equilibrated with a larger volume (1 ml) of a reservoir solution. The reservoir solution contains the precipitant that facilitates the crystallization.

During equilibration the water content in the hanging drop is reduced and the protein-ligand complex, [i.e., the complex between vgTACE and N-{D,L-2-(hydroxyaminocarbonyl)methyl-4-methylpentanoyl}-L-3-amino-2-dimethylbutanoyl-L-alanine, 2-(amino)ethyl amide] forms crystals. To crystallize the protein-ligand complex, one microliter of the protein-ligand complex solution was mixed with one microliter of the reservoir solution, which contains 15% polyethylenglycol 4000, 10% 2-Propanol, and 100 mM Citrate-Buffer pH 5.6. Crystals were observed after one week.

The crystals obtained were washed with the reservoir solution. In the next step, a single protein-ligand complex crystal was put into the reservoir solution, which contained in addition, a 10 mM TACE inhibitor to replace the co-crystallized N-{D,L-2-(hydroxyaminocarbonyl)methyl-4-methylpentanoyl}-L-3-amino-2-dimethylbutanoyl-L-alanine, 2-(amino)ethyl amide. The crystal is usually kept for 72 hours in the solution containing the inhibitor to allow the ligand replacement. After incubation, the crystal was frozen in liquid propane and used for X-ray diffraction.

Results

Two distinct structures of TACE:inhibitor complexes have been previously disclosed [Maskos et. al., *Proc. Natl. Acad. Sci. USA* 95:3408-3412 (1998); Letavic et al. *Biorgan. & Medic. Chem. Lett.* 12:1387-1390 (2002)]. However, neither crystal appears to be amenable to crystal soaking. As disclosed herein, it has been unexpectedly discovered that the uncomplexed TACE protein (apo-protein) is unstable at the high concentrations required to grow and use crystals for X-ray crystallographic studies. Consistently, the crystal of Maskos et. al. has been found to be resistant to standard inhibitor soaking experiments, severely limiting its value in structure based rational drug design.

Stability of TACE: The stability of TACE was examined under several buffer conditions at pH 7.5. Twenty microliter aliquots of TACE at 15 mg/ml were desalted over P-6 spin columns (BioRAD, Hercules, Calif.) that had been equilibrated in:

(a) 25 mM Tris, 0.15M NaCl;

(b) 25 mM Tris; or (c) 25 mM Tris plus N-{D,L-2-(hydroxyaminocarbonyl) methyl-4-methylpentanoyl}-L-3-amino-2-dimethylbutanoyl-L-alanine, 2-(amino)ethyl amide.

The stability of the TACE protein was evaluated after storage at 4 degrees Celsius for seven days. After incubating the TACE polypeptide under the three conditions listed above, Sodium Dodecyl Sulfate PolyAcrylamide Gel Electrophoresis (SDS-PAGE) was performed. The results show that only a single band having a molecular weight of 30 Kd was observed when either high salt (0.15 sodium chloride) or an inhibitor [N-{D,L-2-(hydroxyaminocarbonyl)methyl-4-methylpentanoyl}-L-3-amino-2-dimethylbutanoyl-L-alanine, 2-(amino)ethyl amide, at a 1:1.5 molar ratio enzyme:inhibitor] was included in the incubation. In direct contrast, two additional fainter bands that ran well ahead of the more significant TACE band were observed in the sample lacking either high salt or the inhibitor. The molecular weights of these two additional fainter bands were 14 Kd and 16 Kd, respectively, which add up to the 30 Kd molecular weight of the TACE polypeptide. N-terminal sequencing of the peptides corresponding to the two additional bands indicated that they were indeed, proteolytic products of the TACE protein. Moreover, the sequencing data indicated the presence of a single cleavage site at 352Y-V353 of SEQ ID NO: 2.

Substrate Specificity of TACE: In an effort to understand the role of the different amino-acid residues of TACE regarding substrate specificity, a substitution study was performed at the P'1 position. The catalytic activity of TACE was determined in an assay using the synthetic peptide Ac-SPLAQA-VRSSSR-NH₂ (SEQ ID NO: 17) as the substrate. The sequence corresponds to the cleavage site of TACE on proTNF-alpha, with the sessile bond being between the alanine and the valine. Activity was measured by incubating 100 nM TACE with 100 micromolar substrate in 25 mM HEPES pH 7.3, 5 mM CaCl₂, for 1 hour at room temperature. Product formation was quantified at 214 nm after HPLC separation using a POROS-R1 reverse phase column. Substitution of the P'1 valine (in bold above) with either alanine, glycine or serine decreased activity of TACE to non-detectable levels. Based on this data it was decided to substitute the P'1 position of the internal cleave site [ . . . LGLAY-VGSPR . . . (SEQ ID NO: 16)] with one of these amino acids e.g., either glycine or serine, in an attempt to eliminate the auto-proteolysis of TACE seen in the absence of NaCl.

Stability of TACE and TACE mutants: To test for stability under different storage conditions, 20 ul of TACE protein, at 15 mg/ml, was desalted over BIO-RAD P-6 columns equilibrated at pH 7.5 in:
(a) 25 mM Tris, 0.15M NaCl;
(b) 25 mM Tris+1 mM N-{D,L-2-(hydroxyaminocarbonyl)methyl-4-methylpentanoyl}-L-3-amino-2-dimethylbutanoyl-L-alanine, 2-(amino)ethyl amide; or
(c) 25 mM Tris.

One microliter aliquots were analyzed by SDS-PAGE after storing them for 3 hours, or 17 days at 4 degrees Celsius. In the absence of salt, the native protein exhibits a pattern consistent with substantial proteolysis occurring after only 3 hours, with the protein being completely proteolyzed after 17 days. In direct contrast, all constructs were stable in either 0.15M NaCl, or 1 mM N-{D,L-2-(hydroxyaminocarbonyl) methyl-4-methylpentanoyl}-L-3-amino-2-dimethylbutanoyl-L-alanine, 2-(amino)ethyl amide. The 2 loop mutants V353G and V353S showed improved stability, with the V353G (vgTACE) mutant being highly resistant to auto-proteolysis, even after 17 days.

Crystallization: The TACE mutant V353G (vgTACE) could be crystallized under similar conditions as the native TACE [WO9940182. Published Aug. 12, 1999, U.S. application Ser. No. 09/117,476, filed Jan. 27, 1999, the contents of which are both hereby incorporated by reference in its entirety]. vgTACE was concentrated to 15 mg/ml in 150 mM NaCl, 25 mM Tris-HCl pH 8. After desalting the vgTACE with Bio-Rad P-6 columns, N-{D,L-2-(hydroxyaminocarbonyl)methyl-4-methylpentanoyl}-L-3-amino-2-dimethylbutanoyl-L-alanine, 2-(amino)ethyl amide was added to a molecular ratio of 1:2 (enzyme:inhibitor). The complex was crystallized using the hanging drop vapor diffusion technique. Equal amounts of vgTACE-inhibitor solution were mixed with the reservoir solution, containing 15% Polyethylenglycol 4000, 10% 2-propanol, 100 mM sodium citrate pH 4.6, and equilibrated at 295 degrees Kelvin. Crystals were observed after 7 days.

Crystallographic analysis: vgTACE crystals were washed using the reservoir solution. Glycerol was then added to the reservoir solution to a final concentration of 15%, and the crystals were flash frozen in liquid propane. X-ray diffraction data were collected at 100 degrees Kelvin, using a rotating anode generator (Rigaku/MSC) or synchrotron sources. Diffraction was observed up to 1.7 Å. The vgTACE crystals belong to space group $P2_1 2_1 2_1$ (a=73, b=75, c=103 Å). There are two molecules located within the asymmetric unit. Soaking with the compounds of Table 2 was performed by incubation of the crystals in the reservoir solution in the presence of up to 70 mM of the respective inhibitor. In the V353G mutant crystals, the co-crystallized inhibitor N-{D,L-2-(hydroxyaminocarbonyl)methyl-4-methylpentanoyl}-L-3-amino-2-dimethylbutanoyl-L-alanine, 2-(amino)ethyl amide could be replaced during soaking.

Model building and refinement: The crystal structure of V353G mutant was solved by molecular replacement and refined using standard crystallographic programs. The published TACE structure was used as the starting model [PDB code:1BKC; Maskos et. al., *Proc. Natl. Acad. Sci. USA* 95:3408-3412 (1998)]. Replacement of the co-crystallized inhibitor was verified by difference electron density maps. The vgTACE:inhibitor structures were refined using X-PLOR(CNS). A list of vgTACE:inhibitor structures that have been solved is shown in Table 2 below.

TABLE 2

RESOLUTION OF TACE-INHIBITOR COMPLEXES

| INHIBITOR | Resolution (Angstroms) |
|---|---|
| (4-biphenylsulfonyl)amino-propionic acid | 1.7 |
| 3,4-dimethyl-2-(N-3'-pyridylmethyl-p-methoxysulfonamido)-benzenehydroxyamic acid | 1.9 |
| alpha(R)-[[[4-2-butynyloxy)phenyl]sulfonyl]amino] benzenepropanoic acid | 1.7 |
| N-hydroxy-alpha(R),3(S)-dimethyl-3-[4-[(2-methyl-4-quinolinyl)methoxy]phenyl]-2-oxo-1-pyrrolidineacetamide | 2.1 |
| N-{3-(hydroxyaminocarbonyl)-1-oxo-(2R)-benzylpropyl}-Ile-Leu-OH | 2.0 |

Table 3 below, comprises the coordinate set from the crystal structure of TACE complexed with N-{3-(hydroxyaminocarbonyl)-1-oxo-(2R)-benzylpropyl}-Ile-Leu-OH. To obtain these coordinates a single co-crystal of TACE in complex with N-{D,L-2-(hydroxyaminocarbonyl)methyl-4-methylpentanoyl}-L-3-amino-2-dimethylbutanoyl-L-alanine, 2-(amino)ethyl amide was soaked in 10% polyethylenglycol 8000, 50 mM sodium citrate, 10 mM [N-{3-(hydroxyaminocarbonyl)-1-oxo-(2R)-benzylpropyl}-Ile-Leu-OH] and 10% dimethylsulphoxide (DMSO) for three days. The crystal was transferred into a solution with additional 10% glycerol and flash-frozen in liquid nitrogen. X-ray diffraction data were collected as described above. These data were processed and the structure was refined as described above.

The TACE monomer includes amino acid residues 6-259 of the catalytic domain (see SEQ ID NO: 20) and is bound to the inhibitor, N-{3-(hydroxyaminocarbonyl)-1-oxo-(2R)-benzylpropyl}-Ile-Leu-OH which has the number 260 in Table 3. The catalytic zinc ion has the number 261. Amino acid residues $Arg_{28}$, $Lys_{72}$, $Glu_{81}$, $Lys_{88}$, $Glu_{93}$, $Glu_{94}$, $Lys_{95}$, and $Arg_{143}$ were modeled as Ala residues since their side chains were disordered. The TACE protein used had the amino acid sequence of SEQ ID NO: 20, i.e., $Gly_{139}$ is the single point mutation site replacing $Val_{139}$ of the TACE wild-type amino acid sequence.

In the data set below, one line contains information per one atom. The seven columns of Table 3 represent respectively:
1) residue number,
2) one-letter amino acid code,
3) atom name,
4) x-coordinate,
5) y-coordinate,
6) z-coordinate, and
7) B-factor.

TABLE 3

COORDINATES for the COMPLEX of vgTACE with N-{3-(Hydroxyaminocarbonyl)-1-Oxo-(2R)-Benzylpropyl}-Ile-Leu-OH

| 6 | PRO | CB | 62.073 | 53.680 | 60.089 | 57.01 |
|---|---|---|---|---|---|---|
| 6 | PRO | CG | 62.468 | 55.126 | 60.364 | 57.06 |
| 6 | PRO | C | 59.660 | 54.054 | 59.521 | 56.73 |
| 6 | PRO | O | 59.094 | 53.151 | 60.132 | 56.72 |
| 6 | PRO | N | 61.472 | 55.081 | 58.226 | 56.90 |
| 6 | PRO | CD | 62.545 | 55.773 | 58.963 | 57.18 |
| 6 | PRO | CA | 61.066 | 53.868 | 58.966 | 56.85 |
| 7 | MET | N | 59.104 | 55.240 | 59.307 | 56.47 |
| 7 | MET | CA | 57.761 | 55.534 | 59.770 | 56.16 |
| 7 | MET | CB | 57.653 | 57.002 | 60.180 | 57.02 |
| 7 | MET | CG | 58.514 | 57.370 | 61.375 | 58.06 |
| 7 | MET | SD | 58.165 | 59.050 | 61.936 | 59.40 |
| 7 | MET | CE | 59.102 | 59.999 | 60.715 | 59.24 |
| 7 | MET | C | 56.780 | 55.226 | 58.644 | 55.35 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| | | | | | | |
|---|---|---|---|---|---|---|
| 7 | MET | O | 55.612 | 54.925 | 58.885 | 55.64 |
| 8 | LYS | N | 57.269 | 55.306 | 57.411 | 54.05 |
| 8 | LYS | CA | 56.458 | 55.020 | 56.236 | 52.67 |
| 8 | LYS | CB | 56.923 | 55.885 | 55.062 | 53.02 |
| 8 | LYS | CG | 56.888 | 57.377 | 55.362 | 53.28 |
| 8 | LYS | CD | 57.228 | 58.210 | 54.135 | 53.51 |
| 8 | LYS | CE | 57.057 | 59.698 | 54.425 | 53.52 |
| 8 | LYS | NZ | 57.362 | 60.531 | 53.233 | 53.75 |
| 8 | LYS | C | 56.625 | 53.534 | 55.909 | 51.45 |
| 8 | LYS | O | 57.436 | 53.153 | 55.066 | 51.21 |
| 9 | ASN | N | 55.843 | 52.701 | 56.585 | 49.93 |
| 9 | ASN | CA | 55.927 | 51.263 | 56.398 | 48.31 |
| 9 | ASN | CB | 56.409 | 50.618 | 57.696 | 48.36 |
| 9 | ASN | CG | 55.496 | 50.928 | 58.878 | 48.21 |
| 9 | ASN | OD1 | 55.835 | 50.643 | 60.029 | 48.47 |
| 9 | ASN | ND2 | 54.333 | 51.504 | 58.599 | 48.06 |
| 9 | ASN | C | 54.610 | 50.632 | 55.987 | 47.19 |
| 9 | ASN | O | 54.456 | 49.415 | 56.074 | 47.11 |
| 10 | THR | N | 53.662 | 51.446 | 55.540 | 45.73 |
| 10 | THR | CA | 52.367 | 50.913 | 55.151 | 44.26 |
| 10 | THR | CB | 51.264 | 51.294 | 56.156 | 44.15 |
| 10 | THR | OG1 | 51.681 | 50.975 | 57.487 | 44.15 |
| 10 | THR | CG2 | 49.992 | 50.519 | 55.834 | 43.84 |
| 10 | THR | C | 51.883 | 51.361 | 53.787 | 43.31 |
| 10 | THR | O | 51.918 | 52.546 | 53.454 | 43.14 |
| 11 | CYS | N | 51.420 | 50.393 | 53.007 | 42.09 |
| 11 | CYS | CA | 50.872 | 50.663 | 51.693 | 41.05 |
| 11 | CYS | C | 49.373 | 50.626 | 51.927 | 40.79 |
| 11 | CYS | O | 48.813 | 49.571 | 52.249 | 40.43 |
| 11 | CYS | CB | 51.310 | 49.574 | 50.705 | 40.41 |
| 11 | CYS | SG | 50.526 | 49.576 | 49.063 | 39.35 |
| 12 | LYS | N | 48.737 | 51.792 | 51.812 | 40.40 |
| 12 | LYS | CA | 47.297 | 51.914 | 52.011 | 40.31 |
| 12 | LYS | CB | 46.926 | 53.386 | 52.236 | 40.50 |
| 12 | LYS | CG | 47.582 | 54.002 | 53.467 | 40.84 |
| 12 | LYS | CD | 47.193 | 53.242 | 54.728 | 41.39 |
| 12 | LYS | CE | 47.795 | 53.864 | 55.982 | 42.05 |
| 12 | LYS | NZ | 47.309 | 55.259 | 56.185 | 42.58 |
| 12 | LYS | C | 46.567 | 51.353 | 50.793 | 40.16 |
| 12 | LYS | O | 46.996 | 51.573 | 49.660 | 39.93 |
| 13 | LEU | N | 45.467 | 50.637 | 51.031 | 39.94 |
| 13 | LEU | CA | 44.698 | 50.015 | 49.954 | 39.87 |
| 13 | LEU | CB | 44.540 | 48.506 | 50.189 | 39.57 |
| 13 | LEU | CG | 45.817 | 47.718 | 50.470 | 39.45 |
| 13 | LEU | CD1 | 45.455 | 46.287 | 50.855 | 39.64 |
| 13 | LEU | CD2 | 46.742 | 47.691 | 49.256 | 39.49 |
| 13 | LEU | C | 43.283 | 50.536 | 49.735 | 40.21 |
| 13 | LEU | O | 42.590 | 50.941 | 50.674 | 40.15 |
| 14 | LEU | N | 42.861 | 50.484 | 48.477 | 40.14 |
| 14 | LEU | CA | 41.506 | 50.825 | 48.098 | 40.45 |
| 14 | LEU | CB | 41.451 | 51.674 | 46.823 | 40.27 |
| 14 | LEU | CG | 40.026 | 51.690 | 46.235 | 40.37 |
| 14 | LEU | CD1 | 39.053 | 52.388 | 47.192 | 40.36 |
| 14 | LEU | CD2 | 39.992 | 52.378 | 44.869 | 40.24 |
| 14 | LEU | C | 40.996 | 49.428 | 47.775 | 40.61 |
| 14 | LEU | O | 41.361 | 48.859 | 46.749 | 40.61 |
| 15 | VAL | N | 40.186 | 48.853 | 48.652 | 40.60 |
| 15 | VAL | CA | 39.679 | 47.518 | 48.387 | 40.72 |
| 15 | VAL | CB | 39.685 | 46.670 | 49.668 | 40.68 |
| 15 | VAL | CG1 | 39.000 | 45.333 | 49.416 | 40.84 |
| 15 | VAL | CG2 | 41.133 | 46.454 | 50.110 | 40.43 |
| 15 | VAL | C | 38.287 | 47.606 | 47.805 | 40.94 |
| 15 | VAL | O | 37.403 | 48.247 | 48.374 | 40.84 |
| 16 | VAL | N | 38.104 | 46.979 | 46.648 | 41.32 |
| 16 | VAL | CA | 36.813 | 47.000 | 45.979 | 41.65 |
| 16 | VAL | CB | 36.908 | 47.619 | 44.556 | 41.38 |
| 16 | VAL | CG1 | 35.520 | 47.653 | 43.911 | 41.06 |
| 16 | VAL | CG2 | 37.502 | 49.030 | 44.633 | 41.07 |
| 16 | VAL | C | 36.218 | 45.610 | 45.844 | 42.07 |
| 16 | VAL | O | 36.890 | 44.663 | 45.430 | 41.85 |
| 17 | ALA | N | 34.948 | 45.509 | 46.217 | 42.61 |
| 17 | ALA | CA | 34.195 | 44.272 | 46.124 | 43.48 |
| 17 | ALA | CB | 33.525 | 43.956 | 47.466 | 43.31 |
| 17 | ALA | C | 33.140 | 44.554 | 45.062 | 44.03 |
| 17 | ALA | O | 32.409 | 45.543 | 45.169 | 44.04 |
| 18 | ASP | N | 33.073 | 43.714 | 44.032 | 44.77 |
| 18 | ASP | CA | 32.089 | 43.916 | 42.973 | 45.53 |
| 18 | ASP | CB | 32.632 | 43.438 | 41.611 | 45.20 |
| 18 | ASP | CG | 32.781 | 41.928 | 41.520 | 45.15 |
| 18 | ASP | OD1 | 32.552 | 41.243 | 42.534 | 45.18 |
| 18 | ASP | OD2 | 33.134 | 41.429 | 40.426 | 44.69 |
| 18 | ASP | C | 30.798 | 43.193 | 43.329 | 46.32 |
| 18 | ASP | O | 30.702 | 42.584 | 44.398 | 46.49 |
| 19 | HIS | N | 29.811 | 43.255 | 42.440 | 47.07 |
| 19 | HIS | CA | 28.519 | 42.626 | 42.699 | 47.79 |
| 19 | HIS | CB | 27.505 | 43.003 | 41.603 | 47.47 |
| 19 | HIS | CG | 27.776 | 42.367 | 40.273 | 47.28 |
| 19 | HIS | CD2 | 27.273 | 41.247 | 39.704 | 47.04 |
| 19 | HIS | ND1 | 28.654 | 42.902 | 39.355 | 47.15 |
| 19 | HIS | CE1 | 28.677 | 42.140 | 38.275 | 47.10 |
| 19 | HIS | NE2 | 27.848 | 41.129 | 38.462 | 47.20 |
| 19 | HIS | C | 28.585 | 41.109 | 42.835 | 48.24 |
| 19 | HIS | O | 27.810 | 40.514 | 43.584 | 48.59 |
| 20 | ARG | N | 29.496 | 40.475 | 42.110 | 48.97 |
| 20 | ARG | CA | 29.628 | 39.028 | 42.194 | 49.60 |
| 20 | ARG | CB | 30.652 | 38.517 | 41.180 | 50.00 |
| 20 | ARG | CG | 30.268 | 38.661 | 39.709 | 50.36 |
| 20 | ARG | CD | 31.196 | 37.786 | 38.863 | 50.71 |
| 20 | ARG | NE | 30.919 | 37.837 | 37.428 | 50.98 |
| 20 | ARG | CZ | 30.938 | 38.950 | 36.705 | 51.03 |
| 20 | ARG | NH1 | 31.217 | 40.112 | 37.282 | 51.22 |
| 20 | ARG | NH2 | 30.693 | 38.900 | 35.404 | 51.10 |
| 20 | ARG | C | 30.064 | 38.606 | 43.601 | 49.92 |
| 20 | ARG | O | 29.445 | 37.743 | 44.221 | 50.02 |
| 21 | PHE | N | 31.135 | 39.223 | 44.093 | 50.14 |
| 21 | PHE | CA | 31.680 | 38.921 | 45.419 | 50.40 |
| 21 | PHE | CB | 32.929 | 39.773 | 45.671 | 49.84 |
| 21 | PHE | CG | 33.724 | 39.353 | 46.875 | 49.29 |
| 21 | PHE | CD1 | 34.687 | 38.353 | 46.773 | 49.02 |
| 21 | PHE | CD2 | 33.512 | 39.955 | 48.113 | 49.00 |
| 21 | PHE | CE1 | 35.427 | 37.961 | 47.885 | 48.83 |
| 21 | PHE | CE2 | 34.247 | 39.567 | 49.227 | 48.85 |
| 21 | PHE | CZ | 35.206 | 38.568 | 49.112 | 48.76 |
| 21 | PHE | C | 30.645 | 39.223 | 46.499 | 50.80 |
| 21 | PHE | O | 30.398 | 38.412 | 47.389 | 50.79 |
| 22 | TYR | N | 30.057 | 40.410 | 46.406 | 51.47 |
| 22 | TYR | CA | 29.044 | 40.882 | 47.344 | 52.08 |
| 22 | TYR | CB | 28.473 | 42.208 | 46.847 | 52.14 |
| 22 | TYR | CG | 27.346 | 42.764 | 47.688 | 52.33 |
| 22 | TYR | CD1 | 27.568 | 43.176 | 49.002 | 52.41 |
| 22 | TYR | CE1 | 26.543 | 43.723 | 49.768 | 52.36 |
| 22 | TYR | CD2 | 26.061 | 42.908 | 47.159 | 52.31 |
| 22 | TYR | CE2 | 25.027 | 43.451 | 47.915 | 52.30 |
| 22 | TYR | CZ | 25.274 | 43.857 | 49.219 | 52.34 |
| 22 | TYR | OH | 24.260 | 44.396 | 49.980 | 52.15 |
| 22 | TYR | C | 27.902 | 39.890 | 47.527 | 52.49 |
| 22 | TYR | O | 27.420 | 39.678 | 48.639 | 52.58 |
| 23 | ARG | N | 27.478 | 39.285 | 46.427 | 52.99 |
| 23 | ARG | CA | 26.377 | 38.337 | 46.439 | 53.57 |
| 23 | ARG | CB | 25.772 | 38.259 | 45.032 | 54.21 |
| 23 | ARG | CG | 24.670 | 37.231 | 44.862 | 55.41 |
| 23 | ARG | CD | 24.194 | 37.165 | 43.414 | 56.15 |
| 23 | ARG | NE | 23.138 | 36.171 | 43.243 | 57.12 |
| 23 | ARG | CZ | 22.521 | 35.920 | 42.092 | 57.61 |
| 23 | ARG | NH1 | 22.853 | 36.592 | 40.993 | 57.83 |
| 23 | ARG | NH2 | 21.575 | 34.990 | 42.037 | 57.92 |
| 23 | ARG | C | 26.757 | 36.936 | 46.915 | 53.55 |
| 23 | ARG | O | 26.147 | 36.400 | 47.841 | 53.56 |
| 24 | TYR | N | 27.771 | 36.352 | 46.288 | 53.52 |
| 24 | TYR | CA | 28.201 | 34.997 | 46.617 | 53.49 |
| 24 | TYR | CB | 28.807 | 34.357 | 45.369 | 54.15 |
| 24 | TYR | CG | 27.825 | 34.268 | 44.218 | 54.87 |
| 24 | TYR | CD1 | 26.763 | 33.362 | 44.252 | 55.28 |
| 24 | TYR | CE1 | 25.845 | 33.285 | 43.202 | 55.60 |
| 24 | TYR | CD2 | 27.945 | 35.100 | 43.103 | 55.19 |
| 24 | TYR | CE2 | 27.031 | 35.032 | 42.046 | 55.54 |
| 24 | TYR | CZ | 25.987 | 34.122 | 42.103 | 55.78 |
| 24 | TYR | OH | 25.096 | 34.033 | 41.060 | 56.16 |
| 24 | TYR | C | 29.156 | 34.836 | 47.799 | 53.15 |
| 24 | TYR | O | 29.227 | 33.763 | 48.393 | 53.19 |
| 25 | MET | N | 29.890 | 35.889 | 48.142 | 52.56 |
| 25 | MET | CA | 30.820 | 35.816 | 49.263 | 51.92 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| 25 | MET | CB | 32.197 | 36.350 | 48.850 | 51.12 |
|---|---|---|---|---|---|---|
| 25 | MET | CG | 32.938 | 35.473 | 47.856 | 50.04 |
| 25 | MET | SD | 33.311 | 33.822 | 48.484 | 48.61 |
| 25 | MET | CE | 34.533 | 34.186 | 49.697 | 49.08 |
| 25 | MET | C | 30.312 | 36.601 | 50.468 | 51.97 |
| 25 | MET | O | 30.580 | 36.244 | 51.610 | 51.92 |
| 26 | GLY | N | 29.583 | 37.677 | 50.206 | 52.06 |
| 26 | GLY | CA | 29.065 | 38.489 | 51.289 | 52.32 |
| 26 | GLY | C | 27.611 | 38.186 | 51.579 | 52.46 |
| 26 | GLY | O | 26.975 | 38.889 | 52.360 | 52.49 |
| 27 | ARG | N | 27.089 | 37.137 | 50.949 | 52.57 |
| 27 | ARG | CA | 25.698 | 36.740 | 51.132 | 52.75 |
| 27 | ARG | CB | 25.506 | 36.116 | 52.520 | 52.63 |
| 27 | ARG | C | 24.799 | 37.964 | 50.957 | 52.81 |
| 27 | ARG | O | 23.786 | 38.121 | 51.642 | 52.84 |
| 28 | GLY | N | 25.192 | 38.831 | 50.028 | 52.75 |
| 28 | GLY | CA | 24.429 | 40.032 | 49.748 | 52.70 |
| 28 | GLY | C | 24.352 | 41.002 | 50.906 | 52.59 |
| 28 | GLY | O | 23.514 | 41.900 | 50.912 | 52.70 |
| 29 | GLU | N | 25.225 | 40.832 | 51.890 | 52.61 |
| 29 | GLU | CA | 25.226 | 41.716 | 53.050 | 52.45 |
| 29 | GLU | CB | 25.178 | 40.900 | 54.340 | 52.72 |
| 29 | GLU | CG | 24.292 | 39.673 | 54.284 | 53.26 |
| 29 | GLU | CD | 24.218 | 38.966 | 55.620 | 53.50 |
| 29 | GLU | OE1 | 23.661 | 39.561 | 56.564 | 53.95 |
| 29 | GLU | OE2 | 24.721 | 37.826 | 55.732 | 53.73 |
| 29 | GLU | C | 26.462 | 42.614 | 53.079 | 52.17 |
| 29 | GLU | O | 27.596 | 42.152 | 52.911 | 52.18 |
| 30 | GLU | N | 26.237 | 43.899 | 53.313 | 51.57 |
| 30 | GLU | CA | 27.325 | 44.854 | 53.365 | 51.00 |
| 30 | GLU | CB | 26.760 | 46.264 | 53.525 | 51.37 |
| 30 | GLU | CG | 27.780 | 47.365 | 53.347 | 51.94 |
| 30 | GLU | CD | 27.166 | 48.747 | 53.451 | 52.20 |
| 30 | GLU | OE1 | 26.101 | 48.968 | 52.840 | 52.34 |
| 30 | GLU | OE2 | 27.751 | 49.614 | 54.134 | 52.46 |
| 30 | GLU | C | 28.278 | 44.539 | 54.516 | 50.33 |
| 30 | GLU | O | 29.495 | 44.505 | 54.338 | 50.25 |
| 31 | SER | N | 27.717 | 44.300 | 55.697 | 49.48 |
| 31 | SER | CA | 28.514 | 44.005 | 56.880 | 48.61 |
| 31 | SER | CB | 27.603 | 43.854 | 58.105 | 48.80 |
| 31 | SER | OG | 26.746 | 42.730 | 57.967 | 49.18 |
| 31 | SER | C | 29.353 | 42.742 | 56.714 | 47.87 |
| 31 | SER | O | 30.516 | 42.710 | 57.105 | 47.78 |
| 32 | THR | N | 28.755 | 41.707 | 56.134 | 46.96 |
| 32 | THR | CA | 29.436 | 40.435 | 55.924 | 46.18 |
| 32 | THR | CB | 28.456 | 39.373 | 55.407 | 46.10 |
| 32 | THR | OG1 | 27.349 | 39.281 | 56.310 | 46.18 |
| 32 | THR | CG2 | 29.132 | 38.006 | 55.321 | 45.75 |
| 32 | THR | C | 30.567 | 40.599 | 54.919 | 45.65 |
| 32 | THR | O | 31.699 | 40.177 | 55.165 | 45.46 |
| 33 | THR | N | 30.254 | 41.222 | 53.788 | 44.84 |
| 33 | THR | CA | 31.248 | 41.451 | 52.752 | 44.08 |
| 33 | THR | CB | 30.637 | 42.243 | 51.569 | 43.91 |
| 33 | THR | OG1 | 29.650 | 41.432 | 50.922 | 43.61 |
| 33 | THR | CG2 | 31.710 | 42.623 | 50.550 | 43.80 |
| 33 | THR | C | 32.436 | 42.211 | 53.333 | 43.65 |
| 33 | THR | O | 33.585 | 41.828 | 53.124 | 43.57 |
| 34 | THR | N | 32.155 | 43.271 | 54.086 | 43.09 |
| 34 | THR | CA | 33.205 | 44.091 | 54.688 | 42.76 |
| 34 | THR | CB | 32.614 | 45.317 | 55.413 | 42.93 |
| 34 | THR | OG1 | 31.956 | 46.158 | 54.462 | 43.33 |
| 34 | THR | CG2 | 33.715 | 46.118 | 56.100 | 43.26 |
| 34 | THR | C | 34.082 | 43.328 | 55.676 | 42.38 |
| 34 | THR | O | 35.314 | 43.433 | 55.631 | 42.11 |
| 35 | ASN | N | 33.449 | 42.566 | 56.564 | 41.68 |
| 35 | ASN | CA | 34.183 | 41.800 | 57.564 | 41.10 |
| 35 | ASN | CB | 33.216 | 41.095 | 58.521 | 41.84 |
| 35 | ASN | CG | 32.534 | 42.065 | 59.473 | 42.72 |
| 35 | ASN | OD1 | 33.191 | 42.905 | 60.091 | 43.34 |
| 35 | ASN | ND2 | 31.212 | 41.952 | 59.600 | 43.12 |
| 35 | ASN | C | 35.126 | 40.778 | 56.940 | 40.39 |
| 35 | ASN | O | 36.269 | 40.633 | 57.380 | 40.26 |
| 36 | TYR | N | 34.647 | 40.075 | 55.920 | 39.29 |
| 36 | TYR | CA | 35.469 | 39.076 | 55.255 | 38.44 |
| 36 | TYR | CB | 34.702 | 38.447 | 54.087 | 38.50 |
| 36 | TYR | CG | 35.481 | 37.381 | 53.337 | 38.59 |
| 36 | TYR | CD1 | 36.460 | 37.729 | 52.406 | 38.87 |
| 36 | TYR | CE1 | 37.201 | 36.751 | 51.737 | 38.98 |
| 36 | TYR | CD2 | 35.258 | 36.028 | 53.578 | 38.76 |
| 36 | TYR | CE2 | 35.990 | 35.042 | 52.915 | 38.96 |
| 36 | TYR | CZ | 36.960 | 35.412 | 51.999 | 39.14 |
| 36 | TYR | OH | 37.695 | 34.448 | 51.351 | 39.43 |
| 36 | TYR | C | 36.755 | 39.728 | 54.753 | 37.64 |
| 36 | TYR | O | 37.852 | 39.220 | 54.987 | 37.54 |
| 37 | LEU | N | 36.614 | 40.871 | 54.089 | 36.62 |
| 37 | LEU | CA | 37.764 | 41.582 | 53.544 | 35.66 |
| 37 | LEU | CB | 37.293 | 42.678 | 52.589 | 35.78 |
| 37 | LEU | CG | 36.523 | 42.090 | 51.409 | 35.99 |
| 37 | LEU | CD1 | 35.933 | 43.204 | 50.540 | 36.23 |
| 37 | LEU | CD2 | 37.423 | 41.175 | 50.572 | 35.84 |
| 37 | LEU | C | 38.692 | 42.170 | 54.592 | 34.90 |
| 37 | LEU | O | 39.908 | 42.183 | 54.409 | 34.78 |
| 38 | ILE | N | 38.125 | 42.677 | 55.681 | 33.72 |
| 38 | ILE | CA | 38.931 | 43.237 | 56.750 | 32.55 |
| 38 | ILE | CB | 38.045 | 43.881 | 57.838 | 32.75 |
| 38 | ILE | CG2 | 38.873 | 44.133 | 59.101 | 32.67 |
| 38 | ILE | CG1 | 37.404 | 45.158 | 57.286 | 32.95 |
| 38 | ILE | CD1 | 36.421 | 45.792 | 58.267 | 33.04 |
| 38 | ILE | C | 39.764 | 42.117 | 57.380 | 32.11 |
| 38 | ILE | O | 40.946 | 42.304 | 57.672 | 31.63 |
| 39 | GLU | N | 39.153 | 40.951 | 57.581 | 31.02 |
| 39 | GLU | CA | 39.888 | 39.842 | 58.173 | 30.48 |
| 39 | GLU | CB | 38.920 | 38.752 | 58.652 | 30.75 |
| 39 | GLU | CG | 38.105 | 39.226 | 59.858 | 30.87 |
| 39 | GLU | CD | 37.639 | 38.098 | 60.759 | 31.45 |
| 39 | GLU | OE1 | 38.342 | 37.065 | 60.853 | 31.14 |
| 39 | GLU | OE2 | 36.576 | 38.263 | 61.402 | 31.89 |
| 39 | GLU | C | 40.957 | 39.272 | 57.236 | 29.76 |
| 39 | GLU | O | 42.059 | 38.961 | 57.681 | 29.28 |
| 40 | LEU | N | 40.636 | 39.160 | 55.948 | 29.41 |
| 40 | LEU | CA | 41.580 | 38.648 | 54.951 | 29.09 |
| 40 | LEU | CB | 40.910 | 38.551 | 53.568 | 28.82 |
| 40 | LEU | CG | 41.832 | 38.033 | 52.437 | 28.74 |
| 40 | LEU | CD1 | 41.002 | 37.394 | 51.318 | 29.05 |
| 40 | LEU | CD2 | 42.690 | 39.160 | 51.834 | 28.74 |
| 40 | LEU | C | 42.793 | 39.581 | 54.869 | 29.05 |
| 40 | LEU | O | 43.928 | 39.124 | 54.915 | 29.32 |
| 41 | ILE | N | 42.559 | 40.886 | 54.760 | 28.87 |
| 41 | ILE | CA | 43.666 | 41.827 | 54.663 | 29.03 |
| 41 | ILE | CB | 43.176 | 43.251 | 54.326 | 29.55 |
| 41 | ILE | CG2 | 44.336 | 44.248 | 54.448 | 29.61 |
| 41 | ILE | CG1 | 42.584 | 43.247 | 52.915 | 29.85 |
| 41 | ILE | CD1 | 43.620 | 42.893 | 51.871 | 30.69 |
| 41 | ILE | C | 44.505 | 41.843 | 55.920 | 28.81 |
| 41 | ILE | O | 45.735 | 41.948 | 55.843 | 28.95 |
| 42 | ASP | N | 43.857 | 41.712 | 57.082 | 28.46 |
| 42 | ASP | CA | 44.602 | 41.692 | 58.334 | 28.44 |
| 42 | ASP | CB | 43.642 | 41.680 | 59.532 | 28.61 |
| 42 | ASP | CG | 44.364 | 41.535 | 60.858 | 28.75 |
| 42 | ASP | OD1 | 45.085 | 42.463 | 61.281 | 29.10 |
| 42 | ASP | OD2 | 44.211 | 40.477 | 61.477 | 29.27 |
| 42 | ASP | C | 45.538 | 40.474 | 58.366 | 28.03 |
| 42 | ASP | O | 46.685 | 40.580 | 58.796 | 27.60 |
| 43 | ARG | N | 45.063 | 39.324 | 57.898 | 28.15 |
| 43 | ARG | CA | 45.906 | 38.120 | 57.885 | 28.17 |
| 43 | ARG | CB | 45.062 | 36.863 | 57.623 | 28.15 |
| 43 | ARG | CG | 44.122 | 36.454 | 58.770 | 27.76 |
| 43 | ARG | CD | 43.472 | 35.089 | 58.475 | 27.71 |
| 43 | ARG | NE | 42.820 | 35.046 | 57.161 | 26.80 |
| 43 | ARG | CZ | 41.529 | 35.271 | 56.937 | 27.38 |
| 43 | ARG | NH1 | 40.709 | 35.562 | 57.944 | 27.15 |
| 43 | ARG | NH2 | 41.048 | 35.194 | 55.696 | 27.00 |
| 43 | ARG | C | 47.046 | 38.202 | 56.857 | 27.98 |
| 43 | ARG | O | 48.161 | 37.749 | 57.125 | 28.36 |
| 44 | VAL | N | 46.785 | 38.774 | 55.690 | 28.21 |
| 44 | VAL | CA | 47.840 | 38.909 | 54.678 | 28.18 |
| 44 | VAL | CB | 47.269 | 39.445 | 53.341 | 28.21 |
| 44 | VAL | CG1 | 48.384 | 39.630 | 52.308 | 27.55 |
| 44 | VAL | CG2 | 46.203 | 38.466 | 52.821 | 27.51 |
| 44 | VAL | C | 48.878 | 39.877 | 55.238 | 28.58 |
| 44 | VAL | O | 50.096 | 39.657 | 55.139 | 28.66 |
| 45 | ASP | N | 48.392 | 40.940 | 55.865 | 28.68 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| | | | | | | |
|---|---|---|---|---|---|---|
| 45 | ASP | CA | 49.279 | 41.922 | 56.450 | 28.96 |
| 45 | ASP | CB | 48.460 | 43.038 | 57.112 | 29.15 |
| 45 | ASP | CG | 49.334 | 44.065 | 57.813 | 29.82 |
| 45 | ASP | OD1 | 50.246 | 44.634 | 57.167 | 29.51 |
| 45 | ASP | OD2 | 49.108 | 44.298 | 59.017 | 29.85 |
| 45 | ASP | C | 50.207 | 41.239 | 57.462 | 29.03 |
| 45 | ASP | O | 51.412 | 41.502 | 57.478 | 28.77 |
| 46 | ASP | N | 49.660 | 40.348 | 58.292 | 29.37 |
| 46 | ASP | CA | 50.483 | 39.637 | 59.281 | 29.71 |
| 46 | ASP | CB | 49.672 | 38.556 | 60.019 | 29.76 |
| 46 | ASP | CG | 48.718 | 39.133 | 61.080 | 30.25 |
| 46 | ASP | OD1 | 48.876 | 40.305 | 61.490 | 29.71 |
| 46 | ASP | OD2 | 47.818 | 38.388 | 61.509 | 29.87 |
| 46 | ASP | C | 51.693 | 38.982 | 58.593 | 29.78 |
| 46 | ASP | O | 52.816 | 39.029 | 59.108 | 29.62 |
| 47 | ILE | N | 51.460 | 38.382 | 57.427 | 30.23 |
| 47 | ILE | CA | 52.538 | 37.735 | 56.679 | 30.67 |
| 47 | ILE | CB | 51.992 | 37.002 | 55.433 | 31.15 |
| 47 | ILE | CG2 | 53.125 | 36.727 | 54.447 | 30.51 |
| 47 | ILE | CG1 | 51.279 | 35.721 | 55.872 | 31.48 |
| 47 | ILE | CD1 | 50.451 | 35.132 | 54.756 | 32.09 |
| 47 | ILE | C | 53.593 | 38.755 | 56.254 | 31.14 |
| 47 | ILE | O | 54.792 | 38.510 | 56.405 | 30.87 |
| 48 | TYR | N | 53.148 | 39.896 | 55.732 | 31.49 |
| 48 | TYR | CA | 54.068 | 40.942 | 55.309 | 32.49 |
| 48 | TYR | CB | 53.319 | 42.061 | 54.583 | 31.94 |
| 48 | TYR | CG | 53.040 | 41.766 | 53.135 | 31.45 |
| 48 | TYR | CD1 | 51.996 | 40.921 | 52.760 | 31.16 |
| 48 | TYR | CE1 | 51.788 | 40.592 | 51.431 | 31.44 |
| 48 | TYR | CD2 | 53.865 | 42.281 | 52.135 | 31.29 |
| 48 | TYR | CE2 | 53.663 | 41.959 | 50.801 | 31.23 |
| 48 | TYR | CZ | 52.629 | 41.113 | 50.452 | 31.44 |
| 48 | TYR | OH | 52.432 | 40.774 | 49.131 | 31.26 |
| 48 | TYR | C | 54.870 | 41.543 | 56.460 | 33.48 |
| 48 | TYR | O | 56.089 | 41.631 | 56.384 | 33.46 |
| 49 | ARG | N | 54.185 | 41.952 | 57.526 | 34.66 |
| 49 | ARG | CA | 54.857 | 42.550 | 58.677 | 36.02 |
| 49 | ARG | CB | 53.841 | 42.907 | 59.764 | 36.26 |
| 49 | ARG | CG | 52.763 | 43.847 | 59.289 | 36.68 |
| 49 | ARG | CD | 53.292 | 45.229 | 58.934 | 37.07 |
| 49 | ARG | NE | 52.209 | 46.034 | 58.368 | 37.56 |
| 49 | ARG | CZ | 52.193 | 47.364 | 58.307 | 37.89 |
| 49 | ARG | NH1 | 53.213 | 48.077 | 58.781 | 37.88 |
| 49 | ARG | NH2 | 51.140 | 47.983 | 57.785 | 37.74 |
| 49 | ARG | C | 55.942 | 41.659 | 59.276 | 36.73 |
| 49 | ARG | O | 57.010 | 42.145 | 59.643 | 36.86 |
| 50 | ASN | N | 55.674 | 40.359 | 59.373 | 37.87 |
| 50 | ASN | CA | 56.648 | 39.425 | 59.938 | 38.88 |
| 50 | ASN | CB | 55.960 | 38.130 | 60.391 | 39.28 |
| 50 | ASN | CG | 55.127 | 38.313 | 61.653 | 40.06 |
| 50 | ASN | OD1 | 55.654 | 38.613 | 62.729 | 40.35 |
| 50 | ASN | ND2 | 53.820 | 38.128 | 61.527 | 40.37 |
| 50 | ASN | C | 57.785 | 39.076 | 58.981 | 39.41 |
| 50 | ASN | O | 58.719 | 38.361 | 59.355 | 39.55 |
| 51 | THR | N | 57.716 | 39.570 | 57.748 | 39.83 |
| 51 | THR | CA | 58.759 | 39.273 | 56.766 | 40.21 |
| 51 | THR | CB | 58.193 | 39.341 | 55.321 | 39.71 |
| 51 | THR | OG1 | 57.247 | 38.284 | 55.130 | 39.05 |
| 51 | THR | CG2 | 59.311 | 39.214 | 54.289 | 39.56 |
| 51 | THR | C | 59.963 | 40.214 | 56.884 | 40.90 |
| 51 | THR | O | 59.811 | 41.435 | 56.898 | 40.72 |
| 52 | ALA | N | 61.160 | 39.637 | 56.989 | 41.77 |
| 52 | ALA | CA | 62.377 | 40.435 | 57.081 | 42.50 |
| 52 | ALA | CB | 63.324 | 39.846 | 58.129 | 42.80 |
| 52 | ALA | C | 63.024 | 40.422 | 55.702 | 43.07 |
| 52 | ALA | O | 63.718 | 39.478 | 55.335 | 43.06 |
| 53 | TRP | N | 62.779 | 41.481 | 54.945 | 43.91 |
| 53 | TRP | CA | 63.289 | 41.612 | 53.589 | 45.05 |
| 53 | TRP | CB | 62.739 | 42.900 | 52.974 | 44.35 |
| 53 | TRP | CG | 61.263 | 43.028 | 53.191 | 44.14 |
| 53 | TRP | CD2 | 60.237 | 42.245 | 52.570 | 43.92 |
| 53 | TRP | CE2 | 59.009 | 42.619 | 53.161 | 43.92 |
| 53 | TRP | CE3 | 60.236 | 41.260 | 51.574 | 43.79 |
| 53 | TRP | CD1 | 60.631 | 43.829 | 54.104 | 43.91 |
| 53 | TRP | NE1 | 59.280 | 43.587 | 54.094 | 43.79 |
| 53 | TRP | CZ2 | 57.790 | 42.039 | 52.790 | 43.71 |
| 53 | TRP | CZ3 | 59.020 | 40.681 | 51.205 | 43.76 |
| 53 | TRP | CH2 | 57.817 | 41.076 | 51.813 | 43.65 |
| 53 | TRP | C | 64.812 | 41.568 | 53.469 | 46.12 |
| 53 | TRP | O | 65.355 | 41.475 | 52.366 | 46.40 |
| 54 | ASP | N | 65.501 | 41.633 | 54.601 | 47.29 |
| 54 | ASP | CA | 66.957 | 41.592 | 54.597 | 48.59 |
| 54 | ASP | CB | 67.516 | 42.909 | 55.136 | 48.87 |
| 54 | ASP | CG | 67.313 | 43.057 | 56.624 | 49.36 |
| 54 | ASP | OD1 | 66.354 | 42.460 | 57.157 | 49.66 |
| 54 | ASP | OD2 | 68.106 | 43.777 | 57.264 | 49.88 |
| 54 | ASP | C | 67.405 | 40.438 | 55.481 | 49.24 |
| 54 | ASP | O | 68.549 | 40.387 | 55.914 | 49.44 |
| 55 | ASN | N | 66.486 | 39.514 | 55.748 | 50.07 |
| 55 | ASN | CA | 66.766 | 38.355 | 56.590 | 50.93 |
| 55 | ASN | CB | 67.749 | 37.415 | 55.888 | 51.38 |
| 55 | ASN | CG | 67.176 | 36.824 | 54.618 | 51.78 |
| 55 | ASN | OD1 | 66.118 | 36.188 | 54.642 | 52.49 |
| 55 | ASN | ND2 | 67.866 | 37.028 | 53.500 | 51.87 |
| 55 | ASN | C | 67.325 | 38.768 | 57.948 | 51.31 |
| 55 | ASN | O | 67.796 | 37.932 | 58.719 | 51.50 |
| 56 | ALA | N | 67.259 | 40.062 | 58.238 | 51.62 |
| 56 | ALA | CA | 67.760 | 40.590 | 59.497 | 51.85 |
| 56 | ALA | CB | 68.875 | 41.606 | 59.230 | 51.88 |
| 56 | ALA | C | 66.641 | 41.237 | 60.306 | 51.99 |
| 56 | ALA | O | 65.756 | 40.550 | 60.827 | 52.12 |
| 57 | GLY | N | 66.683 | 42.562 | 60.407 | 52.02 |
| 57 | GLY | CA | 65.673 | 43.273 | 61.172 | 51.90 |
| 57 | GLY | C | 64.834 | 44.247 | 60.371 | 51.78 |
| 57 | GLY | O | 64.105 | 45.066 | 60.941 | 51.80 |
| 58 | PHE | N | 64.934 | 44.170 | 59.047 | 51.52 |
| 58 | PHE | CA | 64.161 | 45.056 | 58.192 | 51.17 |
| 58 | PHE | CB | 64.863 | 45.257 | 56.850 | 51.44 |
| 58 | PHE | CG | 64.329 | 46.414 | 56.053 | 51.66 |
| 58 | PHE | CD1 | 64.497 | 47.719 | 56.504 | 51.71 |
| 58 | PHE | CD2 | 63.679 | 46.201 | 54.838 | 51.82 |
| 58 | PHE | CE1 | 64.030 | 48.797 | 55.754 | 51.85 |
| 58 | PHE | CE2 | 63.206 | 47.273 | 54.078 | 51.76 |
| 58 | PHE | CZ | 63.383 | 48.573 | 54.536 | 51.92 |
| 58 | PHE | C | 62.791 | 44.427 | 57.978 | 50.89 |
| 58 | PHE | O | 62.525 | 43.813 | 56.945 | 50.82 |
| 59 | LYS | N | 61.933 | 44.565 | 58.981 | 50.35 |
| 59 | LYS | CA | 60.584 | 44.027 | 58.924 | 49.76 |
| 59 | LYS | CB | 60.455 | 42.835 | 59.875 | 50.20 |
| 59 | LYS | CG | 60.515 | 43.213 | 61.340 | 50.70 |
| 59 | LYS | CD | 61.263 | 42.182 | 62.176 | 51.68 |
| 59 | LYS | CE | 60.698 | 40.771 | 62.023 | 52.16 |
| 59 | LYS | NZ | 61.171 | 40.095 | 60.774 | 52.55 |
| 59 | LYS | C | 59.623 | 45.130 | 59.342 | 49.05 |
| 59 | LYS | O | 60.017 | 46.292 | 59.468 | 49.13 |
| 60 | GLY | N | 58.366 | 44.768 | 59.563 | 48.23 |
| 60 | GLY | CA | 57.391 | 45.757 | 59.973 | 47.17 |
| 60 | GLY | C | 56.658 | 46.411 | 58.821 | 46.43 |
| 60 | GLY | O | 55.847 | 47.304 | 59.041 | 46.28 |
| 61 | TYR | N | 56.945 | 45.979 | 57.594 | 45.82 |
| 61 | TYR | CA | 56.274 | 46.529 | 56.421 | 45.19 |
| 61 | TYR | CB | 57.231 | 46.588 | 55.220 | 45.23 |
| 61 | TYR | CG | 58.318 | 47.628 | 55.362 | 45.61 |
| 61 | TYR | CD1 | 59.495 | 47.344 | 56.054 | 45.69 |
| 61 | TYR | CE1 | 60.476 | 48.310 | 56.228 | 46.00 |
| 61 | TYR | CD2 | 58.150 | 48.913 | 54.844 | 45.72 |
| 61 | TYR | CE2 | 59.128 | 49.891 | 55.017 | 46.07 |
| 61 | TYR | CZ | 60.287 | 49.579 | 55.711 | 46.07 |
| 61 | TYR | OH | 61.254 | 50.534 | 55.898 | 46.61 |
| 61 | TYR | C | 55.030 | 45.713 | 56.050 | 44.60 |
| 61 | TYR | O | 55.018 | 44.486 | 56.151 | 44.29 |
| 62 | GLY | N | 53.982 | 46.404 | 55.617 | 44.24 |
| 62 | GLY | CA | 52.764 | 45.710 | 55.245 | 43.54 |
| 62 | GLY | C | 51.743 | 46.578 | 54.547 | 43.26 |
| 62 | GLY | O | 52.071 | 47.584 | 53.916 | 43.26 |
| 63 | ILE | N | 50.486 | 46.178 | 54.674 | 42.96 |
| 63 | ILE | CA | 49.382 | 46.884 | 54.055 | 42.58 |
| 63 | ILE | CB | 48.708 | 45.999 | 52.994 | 42.40 |
| 63 | ILE | CG2 | 49.671 | 45.795 | 51.825 | 42.19 |
| 63 | ILE | CG1 | 48.283 | 44.674 | 53.628 | 42.25 |
| 63 | ILE | CD1 | 47.610 | 43.744 | 52.647 | 42.44 |
| 63 | ILE | C | 48.350 | 47.298 | 55.096 | 42.70 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| | | | | | | |
|---|---|---|---|---|---|---|
| 63 | ILE | O | 48.451 | 46.940 | 56.265 | 42.36 |
| 64 | GLN | N | 47.353 | 48.053 | 54.655 | 42.99 |
| 64 | GLN | CA | 46.312 | 48.535 | 55.549 | 43.58 |
| 64 | GLN | CB | 46.872 | 49.646 | 56.435 | 43.72 |
| 64 | GLN | CG | 46.027 | 49.964 | 57.643 | 44.56 |
| 64 | GLN | CD | 46.544 | 51.166 | 58.404 | 44.90 |
| 64 | GLN | OE1 | 46.220 | 52.311 | 58.076 | 45.06 |
| 64 | GLN | NE2 | 47.369 | 50.915 | 59.417 | 45.02 |
| 64 | GLN | C | 45.185 | 49.080 | 54.692 | 43.80 |
| 64 | GLN | O | 45.424 | 49.864 | 53.774 | 43.54 |
| 65 | ILE | N | 43.960 | 48.654 | 54.973 | 44.15 |
| 65 | ILE | CA | 42.821 | 49.133 | 54.208 | 44.77 |
| 65 | ILE | CB | 41.545 | 48.358 | 54.549 | 44.68 |
| 65 | ILE | CG2 | 40.369 | 48.967 | 53.790 | 44.65 |
| 65 | ILE | CG1 | 41.742 | 46.876 | 54.225 | 44.77 |
| 65 | ILE | CD1 | 40.501 | 46.043 | 54.484 | 44.90 |
| 65 | ILE | C | 42.612 | 50.611 | 54.517 | 45.39 |
| 65 | ILE | O | 42.644 | 51.032 | 55.673 | 45.02 |
| 66 | GLU | N | 42.424 | 51.395 | 53.466 | 46.36 |
| 66 | GLU | CA | 42.217 | 52.825 | 53.603 | 47.29 |
| 66 | GLU | CB | 43.081 | 53.570 | 52.595 | 47.91 |
| 66 | GLU | CG | 42.907 | 55.071 | 52.625 | 48.97 |
| 66 | GLU | CD | 44.110 | 55.764 | 53.218 | 49.62 |
| 66 | GLU | OE1 | 44.403 | 55.552 | 54.422 | 50.07 |
| 66 | GLU | OE2 | 44.774 | 56.516 | 52.469 | 49.95 |
| 66 | GLU | C | 40.757 | 53.128 | 53.336 | 47.78 |
| 66 | GLU | O | 40.147 | 53.964 | 54.001 | 47.77 |
| 67 | GLN | N | 40.211 | 52.445 | 52.342 | 48.29 |
| 67 | GLN | CA | 38.820 | 52.613 | 51.971 | 49.15 |
| 67 | GLN | CB | 38.660 | 53.773 | 50.981 | 49.48 |
| 67 | GLN | CG | 37.210 | 54.029 | 50.600 | 50.14 |
| 67 | GLN | CD | 37.025 | 55.165 | 49.609 | 50.48 |
| 67 | GLN | OE1 | 35.895 | 55.527 | 49.284 | 50.88 |
| 67 | GLN | NE2 | 38.127 | 55.729 | 49.120 | 50.48 |
| 67 | GLN | C | 38.304 | 51.330 | 51.334 | 49.40 |
| 67 | GLN | O | 39.037 | 50.640 | 50.621 | 49.36 |
| 68 | ILE | N | 37.044 | 51.010 | 51.604 | 49.87 |
| 68 | ILE | CA | 36.419 | 49.822 | 51.042 | 50.50 |
| 68 | ILE | CB | 35.922 | 48.853 | 52.135 | 50.51 |
| 68 | ILE | CG2 | 35.176 | 47.695 | 51.472 | 50.47 |
| 68 | ILE | CG1 | 37.096 | 48.365 | 52.984 | 50.62 |
| 68 | ILE | CD1 | 36.657 | 47.442 | 54.122 | 50.63 |
| 68 | ILE | C | 35.222 | 50.236 | 50.203 | 51.11 |
| 68 | ILE | O | 34.411 | 51.054 | 50.625 | 51.20 |
| 69 | ARG | N | 35.115 | 49.672 | 49.010 | 51.81 |
| 69 | ARG | CA | 34.001 | 49.973 | 48.132 | 52.54 |
| 69 | ARG | CB | 34.488 | 50.628 | 46.840 | 53.05 |
| 69 | ARG | CG | 35.030 | 52.025 | 47.035 | 53.82 |
| 69 | ARG | CD | 34.029 | 52.901 | 47.769 | 54.59 |
| 69 | ARG | NE | 34.453 | 54.296 | 47.791 | 55.44 |
| 69 | ARG | CZ | 34.497 | 55.078 | 46.715 | 55.75 |
| 69 | ARG | NH1 | 34.140 | 54.601 | 45.528 | 55.91 |
| 69 | ARG | NH2 | 34.897 | 56.340 | 46.823 | 55.87 |
| 69 | ARG | C | 33.268 | 48.694 | 47.807 | 52.75 |
| 69 | ARG | O | 33.845 | 47.762 | 47.256 | 52.71 |
| 70 | ILE | N | 31.992 | 48.651 | 48.162 | 53.11 |
| 70 | ILE | CA | 31.177 | 47.479 | 47.898 | 53.49 |
| 70 | ILE | CB | 30.459 | 47.005 | 49.183 | 53.40 |
| 70 | ILE | CG2 | 29.657 | 45.738 | 48.885 | 53.34 |
| 70 | ILE | CG1 | 31.484 | 46.782 | 50.296 | 53.46 |
| 70 | ILE | CD1 | 30.841 | 46.428 | 51.613 | 53.40 |
| 70 | ILE | C | 30.138 | 47.815 | 46.839 | 53.85 |
| 70 | ILE | O | 29.202 | 48.566 | 47.099 | 53.84 |
| 71 | LEU | N | 30.317 | 47.271 | 45.639 | 54.37 |
| 71 | LEU | CA | 29.379 | 47.506 | 44.549 | 54.89 |
| 71 | LEU | CB | 30.055 | 47.275 | 43.198 | 54.74 |
| 71 | LEU | CG | 31.388 | 48.015 | 43.074 | 54.71 |
| 71 | LEU | CD1 | 32.007 | 47.768 | 41.699 | 54.69 |
| 71 | LEU | CD2 | 31.210 | 49.515 | 43.310 | 54.57 |
| 71 | LEU | C | 28.229 | 46.526 | 44.719 | 55.34 |
| 71 | LEU | O | 28.326 | 45.368 | 44.307 | 55.27 |
| 72 | LYS | N | 27.144 | 47.002 | 45.324 | 55.90 |
| 72 | LYS | CA | 25.969 | 46.177 | 45.587 | 56.55 |
| 72 | LYS | CB | 24.938 | 46.986 | 46.376 | 56.47 |
| 72 | LYS | C | 25.323 | 45.575 | 44.343 | 56.94 |
| 72 | LYS | O | 24.900 | 44.421 | 44.357 | 56.97 |
| 73 | SER | N | 25.245 | 46.346 | 43.265 | 57.51 |
| 73 | SER | CA | 24.637 | 45.839 | 42.038 | 58.13 |
| 73 | SER | CB | 23.242 | 46.451 | 41.846 | 58.24 |
| 73 | SER | OG | 23.283 | 47.867 | 41.883 | 58.49 |
| 73 | SER | C | 25.497 | 46.099 | 40.805 | 58.43 |
| 73 | SER | O | 26.317 | 47.018 | 40.790 | 58.35 |
| 74 | PRO | N | 25.313 | 45.287 | 39.750 | 58.80 |
| 74 | PRO | CD | 24.286 | 44.237 | 39.626 | 58.89 |
| 74 | PRO | CA | 26.069 | 45.414 | 38.501 | 59.17 |
| 74 | PRO | CB | 25.339 | 44.466 | 37.553 | 59.11 |
| 74 | PRO | CG | 24.798 | 43.424 | 38.464 | 58.95 |
| 74 | PRO | C | 26.069 | 46.838 | 37.976 | 59.58 |
| 74 | PRO | O | 25.188 | 47.630 | 38.310 | 59.54 |
| 75 | GLN | N | 27.067 | 47.157 | 37.159 | 60.04 |
| 75 | GLN | CA | 27.183 | 48.482 | 36.565 | 60.43 |
| 75 | GLN | CB | 28.652 | 48.859 | 36.377 | 60.42 |
| 75 | GLN | CG | 28.870 | 50.163 | 35.619 | 60.40 |
| 75 | GLN | CD | 28.245 | 51.355 | 36.315 | 60.49 |
| 75 | GLN | OE1 | 28.527 | 51.624 | 37.480 | 60.43 |
| 75 | GLN | NE2 | 27.389 | 52.080 | 35.599 | 60.54 |
| 75 | GLN | C | 26.495 | 48.464 | 35.211 | 60.80 |
| 75 | GLN | O | 26.787 | 47.614 | 34.374 | 60.79 |
| 76 | GLU | N | 25.574 | 49.397 | 35.001 | 61.39 |
| 76 | GLU | CA | 24.859 | 49.474 | 33.732 | 61.84 |
| 76 | GLU | CB | 23.699 | 50.466 | 33.841 | 62.11 |
| 76 | GLU | CG | 22.626 | 50.078 | 34.855 | 62.52 |
| 76 | GLU | CD | 21.468 | 51.068 | 34.878 | 62.88 |
| 76 | GLU | OE1 | 20.799 | 51.224 | 33.830 | 63.21 |
| 76 | GLU | OE2 | 21.227 | 51.690 | 35.937 | 62.90 |
| 76 | GLU | C | 25.830 | 49.924 | 32.643 | 62.00 |
| 76 | GLU | O | 26.533 | 50.918 | 32.811 | 62.07 |
| 77 | VAL | N | 25.871 | 49.192 | 31.534 | 62.20 |
| 77 | VAL | CA | 26.770 | 49.531 | 30.435 | 62.49 |
| 77 | VAL | CB | 27.862 | 48.459 | 30.257 | 62.52 |
| 77 | VAL | CG1 | 28.693 | 48.369 | 31.537 | 62.62 |
| 77 | VAL | CG2 | 27.224 | 47.108 | 29.924 | 62.51 |
| 77 | VAL | C | 26.085 | 49.736 | 29.083 | 62.64 |
| 77 | VAL | O | 25.424 | 48.839 | 28.544 | 62.75 |
| 78 | LYS | N | 26.270 | 50.930 | 28.535 | 62.74 |
| 78 | LYS | CA | 25.698 | 51.291 | 27.248 | 62.72 |
| 78 | LYS | CB | 26.135 | 52.715 | 26.895 | 62.87 |
| 78 | LYS | CG | 25.966 | 53.683 | 28.068 | 63.12 |
| 78 | LYS | CD | 26.509 | 55.069 | 27.760 | 63.35 |
| 78 | LYS | CE | 25.682 | 55.757 | 26.695 | 63.52 |
| 78 | LYS | NZ | 26.220 | 57.097 | 26.322 | 63.67 |
| 78 | LYS | C | 26.164 | 50.296 | 26.184 | 62.54 |
| 78 | LYS | O | 27.154 | 49.584 | 26.382 | 62.53 |
| 79 | PRO | N | 25.440 | 50.216 | 25.051 | 62.36 |
| 79 | PRO | CD | 24.173 | 50.912 | 24.749 | 62.31 |
| 79 | PRO | CA | 25.796 | 49.298 | 23.964 | 62.20 |
| 79 | PRO | CB | 24.878 | 49.745 | 22.832 | 62.24 |
| 79 | PRO | CG | 23.626 | 50.111 | 23.578 | 62.28 |
| 79 | PRO | C | 27.273 | 49.375 | 23.580 | 61.91 |
| 79 | PRO | O | 27.788 | 50.452 | 23.270 | 62.02 |
| 80 | GLY | N | 27.947 | 48.228 | 23.605 | 61.55 |
| 80 | GLY | CA | 29.356 | 48.175 | 23.258 | 60.89 |
| 80 | GLY | C | 30.309 | 48.534 | 24.385 | 60.40 |
| 80 | GLY | O | 31.483 | 48.166 | 24.331 | 60.45 |
| 81 | GLU | N | 29.819 | 49.255 | 25.391 | 59.82 |
| 81 | GLU | CA | 30.642 | 49.675 | 26.526 | 59.12 |
| 81 | GLU | CB | 29.969 | 50.851 | 27.250 | 59.16 |
| 81 | GLU | C | 30.926 | 48.540 | 27.518 | 58.67 |
| 81 | GLU | O | 30.174 | 47.562 | 27.603 | 58.69 |
| 82 | LYS | N | 32.021 | 48.683 | 28.262 | 57.81 |
| 82 | LYS | CA | 32.429 | 47.696 | 29.263 | 57.01 |
| 82 | LYS | CB | 33.671 | 46.933 | 28.809 | 57.13 |
| 82 | LYS | CG | 33.473 | 46.000 | 27.637 | 57.26 |
| 82 | LYS | CD | 34.827 | 45.557 | 27.082 | 57.37 |
| 82 | LYS | CE | 35.623 | 46.743 | 26.528 | 57.56 |
| 82 | LYS | NZ | 36.890 | 46.328 | 25.854 | 57.55 |
| 82 | LYS | C | 32.756 | 48.344 | 30.597 | 56.39 |
| 82 | LYS | O | 33.085 | 49.530 | 30.678 | 56.15 |
| 83 | HIS | N | 32.669 | 47.535 | 31.643 | 55.70 |
| 83 | HIS | CA | 32.969 | 47.970 | 32.999 | 55.05 |
| 83 | HIS | CB | 31.767 | 48.705 | 33.606 | 54.78 |
| 83 | HIS | CG | 32.061 | 49.374 | 34.916 | 54.53 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| 83 | HIS | CD2 | 32.328 | 50.664 | 35.218 | 54.59 |
| --- | --- | --- | --- | --- | --- | --- |
| 83 | HIS | ND1 | 32.126 | 48.682 | 36.107 | 54.54 |
| 83 | HIS | CE1 | 32.419 | 49.520 | 37.085 | 54.44 |
| 83 | HIS | NE2 | 32.548 | 50.730 | 36.574 | 54.55 |
| 83 | HIS | C | 33.291 | 46.701 | 33.787 | 54.71 |
| 83 | HIS | O | 32.661 | 45.662 | 33.575 | 54.68 |
| 84 | TYR | N | 34.276 | 46.768 | 34.679 | 54.17 |
| 84 | TYR | CA | 34.645 | 45.587 | 35.455 | 53.76 |
| 84 | TYR | CB | 35.851 | 45.880 | 36.350 | 52.91 |
| 84 | TYR | CG | 35.579 | 46.812 | 37.510 | 52.25 |
| 84 | TYR | CD1 | 35.627 | 48.199 | 37.351 | 51.75 |
| 84 | TYR | CE1 | 35.431 | 49.059 | 38.438 | 51.53 |
| 84 | TYR | CD2 | 35.316 | 46.303 | 38.785 | 51.78 |
| 84 | TYR | CE2 | 35.113 | 47.150 | 39.876 | 51.52 |
| 84 | TYR | CZ | 35.175 | 48.522 | 39.701 | 51.42 |
| 84 | TYR | OH | 35.007 | 49.343 | 40.789 | 50.97 |
| 84 | TYR | C | 33.493 | 45.059 | 36.310 | 53.81 |
| 84 | TYR | O | 33.437 | 43.867 | 36.617 | 53.72 |
| 85 | ASN | N | 32.571 | 45.941 | 36.680 | 54.04 |
| 85 | ASN | CA | 31.437 | 45.550 | 37.511 | 54.28 |
| 85 | ASN | CB | 31.208 | 46.599 | 38.604 | 54.07 |
| 85 | ASN | CG | 30.175 | 46.160 | 39.630 | 53.85 |
| 85 | ASN | OD1 | 30.173 | 45.012 | 40.072 | 53.62 |
| 85 | ASN | ND2 | 29.302 | 47.081 | 40.026 | 53.78 |
| 85 | ASN | C | 30.133 | 45.308 | 36.746 | 54.72 |
| 85 | ASN | O | 29.061 | 45.282 | 37.347 | 54.66 |
| 86 | MET | N | 30.222 | 45.121 | 35.430 | 55.28 |
| 86 | MET | CA | 29.032 | 44.865 | 34.622 | 55.89 |
| 86 | MET | CB | 29.305 | 45.136 | 33.133 | 56.02 |
| 86 | MET | CG | 30.326 | 44.225 | 32.476 | 56.14 |
| 86 | MET | SD | 30.704 | 44.761 | 30.775 | 56.77 |
| 86 | MET | CE | 30.752 | 43.196 | 29.895 | 56.07 |
| 86 | MET | C | 28.568 | 43.425 | 34.813 | 56.27 |
| 86 | MET | O | 29.360 | 42.545 | 35.169 | 56.28 |
| 87 | ALA | N | 27.283 | 43.191 | 34.564 | 56.60 |
| 87 | ALA | CA | 26.688 | 41.871 | 34.735 | 56.88 |
| 87 | ALA | CB | 25.177 | 41.953 | 34.505 | 56.95 |
| 87 | ALA | C | 27.285 | 40.784 | 33.855 | 57.08 |
| 87 | ALA | O | 27.508 | 39.662 | 34.310 | 57.04 |
| 88 | LYS | N | 27.542 | 41.107 | 32.595 | 57.40 |
| 88 | LYS | CA | 28.097 | 40.123 | 31.676 | 57.94 |
| 88 | LYS | CB | 27.616 | 40.413 | 30.251 | 57.93 |
| 88 | LYS | C | 29.621 | 40.089 | 31.715 | 58.25 |
| 88 | LYS | O | 30.272 | 41.107 | 31.956 | 58.25 |
| 89 | SER | N | 30.187 | 38.912 | 31.489 | 58.63 |
| 89 | SER | CA | 31.633 | 38.785 | 31.476 | 59.25 |
| 89 | SER | CB | 32.059 | 37.355 | 31.823 | 59.17 |
| 89 | SER | OG | 31.725 | 36.450 | 30.787 | 59.39 |
| 89 | SER | C | 32.070 | 39.146 | 30.062 | 59.60 |
| 89 | SER | O | 31.258 | 39.140 | 29.136 | 59.66 |
| 90 | TYR | N | 33.344 | 39.475 | 29.900 | 59.97 |
| 90 | TYR | CA | 33.884 | 39.847 | 28.597 | 60.31 |
| 90 | TYR | CB | 34.038 | 41.371 | 28.537 | 60.49 |
| 90 | TYR | CG | 34.554 | 41.917 | 27.225 | 60.75 |
| 90 | TYR | CD1 | 35.901 | 41.812 | 26.881 | 60.73 |
| 90 | TYR | CE1 | 36.377 | 42.321 | 25.672 | 60.86 |
| 90 | TYR | CD2 | 33.691 | 42.545 | 26.326 | 60.76 |
| 90 | TYR | CE2 | 34.156 | 43.056 | 25.117 | 60.81 |
| 90 | TYR | CZ | 35.498 | 42.942 | 24.796 | 60.86 |
| 90 | TYR | OH | 35.957 | 43.457 | 23.604 | 60.88 |
| 90 | TYR | C | 35.238 | 39.163 | 28.438 | 60.43 |
| 90 | TYR | O | 35.975 | 39.017 | 29.411 | 60.46 |
| 91 | PRO | N | 35.597 | 38.746 | 27.209 | 60.56 |
| 91 | PRO | CD | 36.958 | 38.218 | 27.000 | 60.61 |
| 91 | PRO | CA | 34.888 | 38.845 | 25.925 | 60.69 |
| 91 | PRO | CB | 36.017 | 38.719 | 24.915 | 60.67 |
| 91 | PRO | CG | 36.899 | 37.713 | 25.577 | 60.65 |
| 91 | PRO | C | 33.772 | 37.830 | 25.645 | 60.74 |
| 91 | PRO | O | 32.830 | 38.138 | 24.908 | 60.86 |
| 92 | ASN | N | 33.877 | 36.627 | 26.208 | 60.72 |
| 92 | ASN | CA | 32.862 | 35.594 | 25.989 | 60.66 |
| 92 | ASN | CB | 33.482 | 34.202 | 26.115 | 60.91 |
| 92 | ASN | CG | 32.607 | 33.117 | 25.509 | 61.25 |
| 92 | ASN | OD1 | 31.443 | 32.951 | 25.889 | 61.45 |
| 92 | ASN | ND2 | 33.164 | 32.372 | 24.557 | 61.35 |
| 92 | ASN | C | 31.701 | 35.713 | 26.970 | 60.49 |
| 92 | ASN | O | 31.734 | 35.126 | 28.051 | 60.44 |
| 93 | GLU | N | 30.674 | 36.463 | 26.581 | 60.23 |
| 93 | GLU | CA | 29.502 | 36.672 | 27.427 | 59.90 |
| 93 | GLU | CB | 28.433 | 37.469 | 26.667 | 60.10 |
| 93 | GLU | C | 28.911 | 35.362 | 27.919 | 59.61 |
| 93 | GLU | O | 28.273 | 35.322 | 28.974 | 59.58 |
| 94 | GLU | N | 29.140 | 34.289 | 27.166 | 59.18 |
| 94 | GLU | CA | 28.603 | 32.976 | 27.518 | 58.67 |
| 94 | GLU | CB | 28.631 | 32.061 | 26.289 | 58.81 |
| 94 | GLU | C | 29.302 | 32.291 | 28.696 | 58.28 |
| 94 | GLU | O | 28.686 | 31.486 | 29.405 | 58.33 |
| 95 | LYS | N | 30.579 | 32.604 | 28.900 | 57.63 |
| 95 | LYS | CA | 31.352 | 32.013 | 29.986 | 56.88 |
| 95 | LYS | CB | 32.843 | 32.047 | 29.640 | 56.89 |
| 95 | LYS | C | 31.102 | 32.719 | 31.323 | 56.39 |
| 95 | LYS | O | 30.639 | 33.863 | 31.368 | 56.43 |
| 96 | ASP | N | 31.415 | 32.026 | 32.414 | 55.64 |
| 96 | ASP | CA | 31.230 | 32.568 | 33.758 | 54.84 |
| 96 | ASP | CB | 31.501 | 31.479 | 34.805 | 55.19 |
| 96 | ASP | CG | 31.613 | 32.036 | 36.220 | 55.58 |
| 96 | ASP | OD1 | 30.665 | 32.704 | 36.685 | 55.84 |
| 96 | ASP | OD2 | 32.650 | 31.798 | 36.868 | 55.61 |
| 96 | ASP | C | 32.100 | 33.782 | 34.073 | 53.98 |
| 96 | ASP | O | 31.639 | 34.734 | 34.707 | 53.84 |
| 97 | ALA | N | 33.348 | 33.758 | 33.616 | 52.96 |
| 97 | ALA | CA | 34.270 | 34.845 | 33.916 | 51.86 |
| 97 | ALA | CB | 35.353 | 34.325 | 34.866 | 52.03 |
| 97 | ALA | C | 34.934 | 35.558 | 32.742 | 51.02 |
| 97 | ALA | O | 35.056 | 35.020 | 31.638 | 50.90 |
| 98 | TRP | N | 35.373 | 36.784 | 33.014 | 49.95 |
| 98 | TRP | CA | 36.080 | 37.600 | 32.036 | 48.91 |
| 98 | TRP | CB | 36.458 | 38.962 | 32.608 | 48.72 |
| 98 | TRP | CG | 35.441 | 40.023 | 32.645 | 48.66 |
| 98 | TRP | CD2 | 35.581 | 41.334 | 32.094 | 48.56 |
| 98 | TRP | CE2 | 34.458 | 42.081 | 32.503 | 48.57 |
| 98 | TRP | CE3 | 36.556 | 41.953 | 31.296 | 48.57 |
| 98 | TRP | CD1 | 34.264 | 40.019 | 33.335 | 48.50 |
| 98 | TRP | NE1 | 33.671 | 41.253 | 33.260 | 48.39 |
| 98 | TRP | CZ2 | 34.279 | 43.421 | 32.145 | 48.50 |
| 98 | TRP | CZ3 | 36.379 | 43.284 | 30.941 | 48.55 |
| 98 | TRP | CH2 | 35.248 | 44.004 | 31.367 | 48.57 |
| 98 | TRP | C | 37.413 | 36.939 | 31.772 | 48.06 |
| 98 | TRP | O | 37.813 | 36.005 | 32.470 | 47.91 |
| 99 | ASP | N | 38.104 | 37.453 | 30.761 | 47.24 |
| 99 | ASP | CA | 39.457 | 37.013 | 30.468 | 46.10 |
| 99 | ASP | CB | 39.929 | 37.579 | 29.137 | 46.43 |
| 99 | ASP | CG | 41.427 | 37.508 | 28.986 | 46.46 |
| 99 | ASP | OD1 | 41.941 | 36.400 | 28.727 | 47.06 |
| 99 | ASP | OD2 | 42.092 | 38.550 | 29.144 | 46.60 |
| 99 | ASP | C | 40.144 | 37.776 | 31.600 | 45.23 |
| 99 | ASP | O | 40.003 | 39.002 | 31.691 | 44.88 |
| 100 | VAL | N | 40.867 | 37.073 | 32.466 | 44.29 |
| 100 | VAL | CA | 41.502 | 37.725 | 33.605 | 43.47 |
| 100 | VAL | CB | 42.310 | 36.706 | 34.465 | 43.18 |
| 100 | VAL | CG1 | 43.509 | 36.157 | 33.689 | 42.91 |
| 100 | VAL | CG2 | 42.758 | 37.388 | 35.760 | 42.85 |
| 100 | VAL | C | 42.387 | 38.923 | 33.256 | 43.23 |
| 100 | VAL | O | 42.304 | 39.971 | 33.909 | 42.97 |
| 101 | LYS | N | 43.225 | 38.777 | 32.233 | 42.98 |
| 101 | LYS | CA | 44.107 | 39.864 | 31.822 | 43.00 |
| 101 | LYS | CB | 45.033 | 39.393 | 30.690 | 43.37 |
| 101 | LYS | CG | 46.058 | 40.425 | 30.248 | 43.86 |
| 101 | LYS | CD | 46.966 | 39.889 | 29.141 | 44.34 |
| 101 | LYS | CE | 47.942 | 40.968 | 28.673 | 44.98 |
| 101 | LYS | NZ | 49.056 | 40.417 | 27.830 | 44.94 |
| 101 | LYS | C | 43.281 | 41.079 | 31.377 | 42.76 |
| 101 | LYS | O | 43.573 | 42.216 | 31.754 | 42.74 |
| 102 | MET | N | 42.245 | 40.838 | 30.579 | 42.66 |
| 102 | MET | CA | 41.385 | 41.924 | 30.121 | 42.38 |
| 102 | MET | CB | 40.387 | 41.424 | 29.077 | 42.94 |
| 102 | MET | CG | 41.000 | 41.193 | 27.696 | 43.54 |
| 102 | MET | SD | 39.812 | 40.663 | 26.435 | 44.26 |
| 102 | MET | CE | 40.520 | 39.136 | 25.937 | 44.13 |
| 102 | MET | C | 40.632 | 42.531 | 31.296 | 41.87 |
| 102 | MET | O | 40.461 | 43.744 | 31.373 | 42.04 |
| 103 | LEU | N | 40.186 | 41.687 | 32.220 | 41.39 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| | | | | | | |
|---|---|---|---|---|---|---|
| 103 | LEU | CA | 39.457 | 42.177 | 33.376 | 40.80 |
| 103 | LEU | CB | 38.980 | 41.007 | 34.245 | 40.97 |
| 103 | LEU | CG | 38.421 | 41.464 | 35.605 | 41.14 |
| 103 | LEU | CD1 | 37.354 | 42.554 | 35.429 | 41.16 |
| 103 | LEU | CD2 | 37.840 | 40.278 | 36.376 | 40.92 |
| 103 | LEU | C | 40.315 | 43.124 | 34.207 | 40.26 |
| 103 | LEU | O | 39.854 | 44.181 | 34.630 | 39.94 |
| 104 | LEU | N | 41.570 | 42.751 | 34.432 | 39.97 |
| 104 | LEU | CA | 42.457 | 43.586 | 35.234 | 39.64 |
| 104 | LEU | CB | 43.802 | 42.873 | 35.453 | 39.38 |
| 104 | LEU | CG | 44.769 | 43.686 | 36.322 | 39.11 |
| 104 | LEU | CD1 | 44.122 | 44.066 | 37.656 | 38.99 |
| 104 | LEU | CD2 | 46.064 | 42.905 | 36.567 | 39.19 |
| 104 | LEU | C | 42.673 | 44.958 | 34.591 | 39.70 |
| 104 | LEU | O | 42.686 | 45.977 | 35.282 | 39.74 |
| 105 | GLU | N | 42.829 | 44.991 | 33.270 | 39.72 |
| 105 | GLU | CA | 43.038 | 46.262 | 32.590 | 39.81 |
| 105 | GLU | CB | 43.403 | 46.048 | 31.113 | 39.50 |
| 105 | GLU | CG | 44.044 | 47.290 | 30.505 | 39.45 |
| 105 | GLU | CD | 44.533 | 47.106 | 29.080 | 39.30 |
| 105 | GLU | OE1 | 45.020 | 46.004 | 28.735 | 39.29 |
| 105 | GLU | OE2 | 44.446 | 48.082 | 28.308 | 39.37 |
| 105 | GLU | C | 41.783 | 47.130 | 32.701 | 40.04 |
| 105 | GLU | O | 41.875 | 48.339 | 32.914 | 39.95 |
| 106 | GLN | N | 40.611 | 46.510 | 32.565 | 40.23 |
| 106 | GLN | CA | 39.351 | 47.246 | 32.676 | 40.32 |
| 106 | GLN | CB | 38.159 | 46.328 | 32.436 | 40.79 |
| 106 | GLN | CG | 36.847 | 47.083 | 32.344 | 41.31 |
| 106 | GLN | CD | 36.810 | 47.977 | 31.122 | 41.76 |
| 106 | GLN | OE1 | 36.925 | 47.497 | 30.003 | 42.24 |
| 106 | GLN | NE2 | 36.663 | 49.282 | 31.331 | 41.92 |
| 106 | GLN | C | 39.214 | 47.853 | 34.066 | 40.23 |
| 106 | GLN | O | 38.889 | 49.037 | 34.225 | 39.87 |
| 107 | PHE | N | 39.451 | 47.030 | 35.080 | 39.95 |
| 107 | PHE | CA | 39.350 | 47.502 | 36.448 | 39.81 |
| 107 | PHE | CB | 39.753 | 46.396 | 37.425 | 39.46 |
| 107 | PHE | CG | 39.855 | 46.859 | 38.843 | 39.13 |
| 107 | PHE | CD1 | 38.759 | 47.434 | 39.479 | 38.92 |
| 107 | PHE | CD2 | 41.057 | 46.745 | 39.541 | 39.16 |
| 107 | PHE | CE1 | 38.853 | 47.892 | 40.783 | 38.80 |
| 107 | PHE | CE2 | 41.166 | 47.200 | 40.852 | 38.87 |
| 107 | PHE | CZ | 40.062 | 47.777 | 41.475 | 39.11 |
| 107 | PHE | C | 40.249 | 48.714 | 36.635 | 39.97 |
| 107 | PHE | O | 39.852 | 49.705 | 37.249 | 39.64 |
| 108 | SER | N | 41.467 | 48.624 | 36.100 | 40.20 |
| 108 | SER | CA | 42.435 | 49.708 | 36.198 | 40.65 |
| 108 | SER | CB | 43.764 | 49.281 | 35.555 | 40.75 |
| 108 | SER | OG | 44.397 | 48.270 | 36.326 | 40.70 |
| 108 | SER | C | 41.901 | 50.976 | 35.525 | 41.00 |
| 108 | SER | O | 42.091 | 52.085 | 36.023 | 40.78 |
| 109 | PHE | N | 41.232 | 50.796 | 34.392 | 41.58 |
| 109 | PHE | CA | 40.664 | 51.914 | 33.647 | 42.31 |
| 109 | PHE | CB | 40.138 | 51.422 | 32.294 | 42.55 |
| 109 | PHE | CG | 39.381 | 52.468 | 31.512 | 43.19 |
| 109 | PHE | CD1 | 40.058 | 53.840 | 30.840 | 43.31 |
| 109 | PHE | CD2 | 37.986 | 52.444 | 31.466 | 43.13 |
| 109 | PHE | CE1 | 39.358 | 54.472 | 30.134 | 43.43 |
| 109 | PHE | CE2 | 37.277 | 53.421 | 30.766 | 43.47 |
| 109 | PHE | CZ | 37.965 | 54.440 | 30.097 | 43.28 |
| 109 | PHE | C | 39.530 | 52.604 | 34.409 | 42.61 |
| 109 | PHE | O | 39.489 | 53.828 | 34.504 | 42.49 |
| 110 | ASP | N | 38.616 | 51.810 | 34.955 | 43.11 |
| 110 | ASP | CA | 37.468 | 52.356 | 35.672 | 43.65 |
| 110 | ASP | CB | 36.394 | 51.278 | 35.834 | 43.73 |
| 110 | ASP | CG | 35.826 | 50.827 | 34.511 | 43.66 |
| 110 | ASP | OD1 | 35.467 | 51.703 | 33.698 | 44.35 |
| 110 | ASP | OD2 | 35.725 | 49.605 | 34.280 | 43.87 |
| 110 | ASP | C | 37.756 | 52.985 | 37.026 | 44.03 |
| 110 | ASP | O | 37.168 | 54.011 | 37.367 | 44.05 |
| 111 | ILE | N | 38.658 | 52.384 | 37.796 | 44.24 |
| 111 | ILE | CA | 38.982 | 52.903 | 39.118 | 44.73 |
| 111 | ILE | CB | 39.388 | 51.739 | 40.074 | 44.96 |
| 111 | ILE | CG2 | 40.899 | 51.509 | 40.001 | 45.08 |
| 111 | ILE | CG1 | 38.920 | 52.040 | 41.499 | 45.06 |
| 111 | ILE | CD1 | 37.407 | 52.123 | 41.605 | 45.37 |
| 111 | ILE | C | 40.097 | 53.952 | 39.091 | 44.84 |
| 111 | ILE | O | 40.495 | 54.472 | 40.134 | 44.79 |
| 112 | ALA | N | 40.581 | 54.269 | 37.894 | 45.28 |
| 112 | ALA | CA | 41.668 | 55.234 | 37.703 | 45.60 |
| 112 | ALA | CB | 41.664 | 55.721 | 36.251 | 45.60 |
| 112 | ALA | C | 41.703 | 56.437 | 38.656 | 46.11 |
| 112 | ALA | O | 42.695 | 56.654 | 39.359 | 45.85 |
| 113 | GLU | N | 40.633 | 57.230 | 38.672 | 46.58 |
| 113 | GLU | CA | 40.579 | 58.404 | 39.542 | 47.25 |
| 113 | GLU | CB | 39.206 | 59.083 | 39.453 | 48.10 |
| 113 | GLU | CG | 38.831 | 59.503 | 38.044 | 49.39 |
| 113 | GLU | CD | 38.447 | 58.322 | 37.168 | 50.14 |
| 113 | GLU | OE1 | 38.460 | 58.476 | 35.927 | 50.83 |
| 113 | GLU | OE2 | 38.124 | 57.243 | 37.721 | 50.63 |
| 113 | GLU | C | 40.882 | 58.058 | 40.996 | 47.18 |
| 113 | GLU | O | 41.702 | 58.714 | 41.640 | 46.96 |
| 114 | GLU | N | 40.223 | 57.028 | 41.515 | 47.26 |
| 114 | GLU | CA | 40.459 | 56.624 | 42.895 | 47.33 |
| 114 | GLU | CB | 39.387 | 55.624 | 43.339 | 48.04 |
| 114 | GLU | CG | 37.978 | 56.204 | 43.279 | 49.07 |
| 114 | GLU | CD | 36.938 | 55.295 | 43.903 | 49.76 |
| 114 | GLU | OE1 | 37.024 | 55.045 | 45.129 | 50.01 |
| 114 | GLU | OE2 | 36.034 | 54.831 | 43.169 | 50.18 |
| 114 | GLU | C | 41.859 | 56.027 | 43.058 | 46.96 |
| 114 | GLU | O | 42.580 | 56.374 | 43.990 | 46.83 |
| 115 | ALA | N | 42.250 | 55.155 | 42.131 | 46.60 |
| 115 | ALA | CA | 43.560 | 54.518 | 42.188 | 46.18 |
| 115 | ALA | CB | 43.763 | 53.636 | 40.954 | 46.08 |
| 115 | ALA | C | 44.692 | 55.540 | 42.296 | 45.96 |
| 115 | ALA | O | 45.732 | 55.261 | 42.888 | 45.88 |
| 116 | SER | N | 44.479 | 56.726 | 41.734 | 45.83 |
| 116 | SER | CA | 45.491 | 57.781 | 41.752 | 45.45 |
| 116 | SER | CB | 45.051 | 58.941 | 40.857 | 45.79 |
| 116 | SER | OG | 43.950 | 59.637 | 41.431 | 46.56 |
| 116 | SER | C | 45.783 | 58.321 | 43.145 | 45.01 |
| 116 | SER | O | 46.820 | 58.942 | 43.370 | 44.95 |
| 117 | LYS | N | 44.877 | 58.078 | 44.084 | 44.49 |
| 117 | LYS | CA | 45.034 | 58.592 | 45.438 | 43.96 |
| 117 | LYS | CB | 43.699 | 59.167 | 45.916 | 44.62 |
| 117 | LYS | CG | 43.180 | 60.294 | 45.040 | 45.26 |
| 117 | LYS | CD | 41.749 | 60.682 | 45.391 | 45.71 |
| 117 | LYS | CE | 41.290 | 61.840 | 44.512 | 46.27 |
| 117 | LYS | NZ | 39.905 | 62.270 | 44.841 | 46.64 |
| 117 | LYS | C | 45.562 | 57.617 | 46.481 | 43.42 |
| 117 | LYS | O | 45.813 | 58.014 | 47.617 | 43.44 |
| 118 | VAL | N | 45.735 | 56.351 | 46.111 | 42.52 |
| 118 | VAL | CA | 46.239 | 55.359 | 47.062 | 41.47 |
| 118 | VAL | CB | 45.155 | 54.330 | 47.435 | 41.77 |
| 118 | VAL | CG1 | 44.181 | 54.939 | 48.444 | 41.78 |
| 118 | VAL | CG2 | 44.417 | 53.882 | 46.168 | 41.66 |
| 118 | VAL | C | 47.457 | 54.579 | 46.589 | 40.74 |
| 118 | VAL | O | 47.823 | 54.611 | 45.416 | 40.46 |
| 119 | CYS | N | 48.076 | 53.867 | 47.526 | 39.88 |
| 119 | CYS | CA | 49.242 | 53.057 | 47.226 | 38.75 |
| 119 | CYS | C | 48.871 | 51.928 | 46.269 | 38.23 |
| 119 | CYS | O | 49.550 | 51.705 | 45.262 | 37.93 |
| 119 | CYS | CB | 49.828 | 52.489 | 48.516 | 38.99 |
| 119 | CYS | SG | 51.156 | 51.304 | 48.189 | 39.08 |
| 120 | LEU | N | 47.782 | 51.232 | 46.582 | 37.29 |
| 120 | LEU | CA | 47.294 | 50.130 | 45.758 | 36.83 |
| 120 | LEU | CB | 47.825 | 48.787 | 46.268 | 36.78 |
| 120 | LEU | CG | 49.289 | 48.477 | 45.935 | 36.84 |
| 120 | LEU | CD1 | 49.699 | 47.143 | 46.584 | 36.69 |
| 120 | LEU | CD2 | 49.505 | 48.411 | 44.416 | 36.93 |
| 120 | LEU | C | 45.776 | 50.044 | 45.758 | 36.55 |
| 120 | LEU | O | 45.117 | 50.448 | 46.712 | 36.38 |
| 121 | ALA | N | 45.237 | 49.498 | 44.676 | 36.37 |
| 121 | ALA | CA | 43.802 | 49.283 | 44.539 | 36.19 |
| 121 | ALA | CB | 43.233 | 50.126 | 43.398 | 36.11 |
| 121 | ALA | C | 43.670 | 47.790 | 44.225 | 35.94 |
| 121 | ALA | O | 44.370 | 47.278 | 43.354 | 35.76 |
| 122 | HIS | N | 42.789 | 47.092 | 44.937 | 35.85 |
| 122 | HIS | CA | 42.614 | 45.661 | 44.717 | 35.65 |
| 122 | HIS | CB | 43.191 | 44.869 | 45.903 | 35.42 |
| 122 | HIS | CG | 43.523 | 43.447 | 45.575 | 35.09 |
| 122 | HIS | CD2 | 42.833 | 42.302 | 45.778 | 34.99 |
| 122 | HIS | ND1 | 44.674 | 43.086 | 44.906 | 35.06 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| 122 | HIS | CE1 | 44.675 | 41.780 | 44.710 | 34.72 |
|---|---|---|---|---|---|---|
| 122 | HIS | NE2 | 43.571 | 41.280 | 45.227 | 34.70 |
| 122 | HIS | C | 41.147 | 45.298 | 44.532 | 35.95 |
| 122 | HIS | O | 40.281 | 45.718 | 45.306 | 35.96 |
| 123 | LEU | N | 40.882 | 44.503 | 43.503 | 36.17 |
| 123 | LEU | CA | 39.536 | 44.053 | 43.186 | 36.35 |
| 123 | LEU | CB | 39.325 | 44.126 | 41.676 | 36.14 |
| 123 | LEU | CG | 38.054 | 43.424 | 41.186 | 36.51 |
| 123 | LEU | CD1 | 36.797 | 44.062 | 41.781 | 35.94 |
| 123 | LEU | CD2 | 37.995 | 43.461 | 39.652 | 35.81 |
| 123 | LEU | C | 39.250 | 42.627 | 43.669 | 36.77 |
| 123 | LEU | O | 39.970 | 41.685 | 43.334 | 36.61 |
| 124 | PHE | N | 38.204 | 42.482 | 44.480 | 36.97 |
| 124 | PHE | CA | 37.798 | 41.166 | 44.955 | 37.31 |
| 124 | PHE | CB | 37.563 | 41.158 | 46.470 | 36.56 |
| 124 | PHE | CG | 38.827 | 41.275 | 47.275 | 35.87 |
| 124 | PHE | CD1 | 39.350 | 42.520 | 47.601 | 35.46 |
| 124 | PHE | CD2 | 39.510 | 40.130 | 47.683 | 35.68 |
| 124 | PHE | CE1 | 40.536 | 42.630 | 48.327 | 35.35 |
| 124 | PHE | CE2 | 40.701 | 40.225 | 48.411 | 35.04 |
| 124 | PHE | CZ | 41.211 | 41.476 | 48.732 | 35.19 |
| 124 | PHE | C | 36.515 | 40.847 | 44.222 | 37.97 |
| 124 | PHE | O | 35.510 | 41.533 | 44.395 | 37.89 |
| 125 | THR | N | 36.576 | 39.819 | 43.387 | 38.53 |
| 125 | THR | CA | 35.442 | 39.382 | 42.589 | 39.62 |
| 125 | THR | CB | 35.743 | 39.519 | 41.082 | 39.80 |
| 125 | THR | OG1 | 34.580 | 39.180 | 40.313 | 40.27 |
| 125 | THR | CG2 | 36.882 | 38.572 | 40.698 | 40.00 |
| 125 | THR | C | 35.143 | 37.914 | 42.872 | 40.18 |
| 125 | THR | O | 35.818 | 37.267 | 43.673 | 39.87 |
| 126 | TYR | N | 34.129 | 37.392 | 42.197 | 40.95 |
| 126 | TYR | CA | 33.747 | 35.998 | 42.363 | 41.69 |
| 126 | TYR | CB | 32.552 | 35.879 | 43.318 | 41.98 |
| 126 | TYR | CG | 32.259 | 34.454 | 43.736 | 42.49 |
| 126 | TYR | CD1 | 33.053 | 33.808 | 44.685 | 42.57 |
| 126 | TYR | CE1 | 32.818 | 32.482 | 45.039 | 42.99 |
| 126 | TYR | CD2 | 31.218 | 33.735 | 43.151 | 42.74 |
| 126 | TYR | CE2 | 30.973 | 32.403 | 43.495 | 42.81 |
| 126 | TYR | CZ | 31.777 | 31.784 | 44.437 | 42.91 |
| 126 | TYR | OH | 31.566 | 30.465 | 44.755 | 43.11 |
| 126 | TYR | C | 33.394 | 35.384 | 41.008 | 42.12 |
| 126 | TYR | O | 32.224 | 35.230 | 40.670 | 42.34 |
| 127 | GLN | N | 34.415 | 35.065 | 40.219 | 42.76 |
| 127 | GLN | CA | 34.208 | 34.442 | 38.915 | 43.26 |
| 127 | GLN | CB | 34.217 | 35.498 | 37.799 | 43.14 |
| 127 | GLN | CG | 35.246 | 36.612 | 37.946 | 42.91 |
| 127 | GLN | CD | 34.958 | 37.792 | 37.024 | 42.59 |
| 127 | GLN | OE1 | 34.938 | 37.654 | 35.803 | 42.66 |
| 127 | GLN | NE2 | 34.735 | 38.958 | 37.610 | 42.61 |
| 127 | GLN | C | 35.260 | 33.360 | 38.672 | 43.75 |
| 127 | GLN | O | 36.400 | 33.474 | 39.120 | 43.51 |
| 128 | ASP | N | 34.861 | 32.303 | 37.973 | 44.39 |
| 128 | ASP | CA | 35.745 | 31.179 | 37.705 | 45.26 |
| 128 | ASP | CB | 34.920 | 29.893 | 37.597 | 46.00 |
| 128 | ASP | CG | 35.770 | 28.639 | 37.682 | 46.60 |
| 128 | ASP | OD1 | 37.011 | 28.752 | 37.811 | 47.14 |
| 128 | ASP | OD2 | 35.186 | 27.533 | 37.626 | 47.15 |
| 128 | ASP | C | 36.548 | 31.386 | 36.434 | 45.56 |
| 128 | ASP | O | 36.023 | 31.228 | 35.331 | 45.53 |
| 129 | PHE | N | 37.822 | 31.740 | 36.602 | 45.62 |
| 129 | PHE | CA | 38.719 | 31.982 | 35.477 | 45.80 |
| 129 | PHE | CB | 39.944 | 32.797 | 35.916 | 45.38 |
| 129 | PHE | CG | 39.615 | 34.179 | 36.412 | 44.95 |
| 129 | PHE | CD1 | 38.936 | 35.081 | 35.599 | 44.72 |
| 129 | PHE | CD2 | 39.986 | 34.578 | 37.690 | 44.59 |
| 129 | PHE | CE1 | 38.630 | 36.362 | 36.057 | 44.77 |
| 129 | PHE | CE2 | 39.687 | 35.854 | 38.158 | 44.62 |
| 129 | PHE | CZ | 39.006 | 36.750 | 37.342 | 44.61 |
| 129 | PHE | C | 39.193 | 30.673 | 34.875 | 46.19 |
| 129 | PHE | O | 39.149 | 29.622 | 35.521 | 46.15 |
| 130 | ASP | N | 39.651 | 30.755 | 33.630 | 46.61 |
| 130 | ASP | CA | 40.154 | 29.597 | 32.896 | 47.04 |
| 130 | ASP | CB | 40.314 | 29.949 | 31.417 | 47.59 |
| 130 | ASP | CG | 39.089 | 29.600 | 30.604 | 48.18 |
| 130 | ASP | OD1 | 38.725 | 28.403 | 30.574 | 48.64 |
| 130 | ASP | OD2 | 38.490 | 30.514 | 29.994 | 48.61 |
| 130 | ASP | C | 41.479 | 29.056 | 33.412 | 46.87 |
| 130 | ASP | O | 42.295 | 29.792 | 33.967 | 46.99 |
| 131 | MET | N | 41.682 | 27.759 | 33.211 | 46.72 |
| 131 | MET | CA | 42.907 | 27.088 | 33.618 | 46.61 |
| 131 | MET | CB | 44.112 | 27.686 | 32.873 | 47.71 |
| 131 | MET | CG | 43.962 | 27.784 | 31.348 | 49.21 |
| 131 | MET | SD | 45.510 | 28.252 | 30.493 | 50.81 |
| 131 | MET | CE | 45.787 | 29.965 | 31.114 | 50.14 |
| 131 | MET | C | 43.155 | 27.148 | 35.129 | 45.94 |
| 131 | MET | O | 44.265 | 26.870 | 35.582 | 45.93 |
| 132 | GLY | N | 42.132 | 27.517 | 35.899 | 44.94 |
| 132 | GLY | CA | 42.277 | 27.580 | 37.346 | 44.07 |
| 132 | GLY | C | 43.000 | 28.794 | 37.914 | 43.19 |
| 132 | GLY | O | 43.528 | 28.745 | 39.033 | 43.33 |
| 133 | THR | N | 43.023 | 29.882 | 37.150 | 42.18 |
| 133 | THR | CA | 43.666 | 31.121 | 37.578 | 40.98 |
| 133 | THR | CB | 43.808 | 32.099 | 36.383 | 41.19 |
| 133 | THR | OG1 | 44.649 | 31.515 | 35.377 | 41.40 |
| 133 | THR | CG2 | 44.414 | 33.427 | 36.842 | 41.23 |
| 133 | THR | C | 42.809 | 31.771 | 38.674 | 39.94 |
| 133 | THR | O | 41.586 | 31.842 | 38.546 | 39.84 |
| 134 | LEU | N | 43.444 | 32.239 | 39.747 | 38.76 |
| 134 | LEU | CA | 42.711 | 32.869 | 40.845 | 37.81 |
| 134 | LEU | CB | 43.042 | 32.173 | 42.175 | 37.94 |
| 134 | LEU | CG | 42.389 | 30.789 | 42.318 | 37.96 |
| 134 | LEU | CD1 | 42.685 | 30.206 | 43.698 | 37.70 |
| 134 | LEU | CD2 | 40.870 | 30.873 | 42.122 | 37.86 |
| 134 | LEU | C | 42.927 | 34.377 | 41.003 | 37.01 |
| 134 | LEU | O | 42.134 | 35.065 | 41.650 | 36.89 |
| 135 | GLY | N | 43.998 | 34.902 | 40.430 | 36.22 |
| 135 | GLY | CA | 44.235 | 36.328 | 40.559 | 35.22 |
| 135 | GLY | C | 45.271 | 36.830 | 39.581 | 34.68 |
| 135 | GLY | O | 45.902 | 36.035 | 38.886 | 34.19 |
| 136 | LEU | N | 45.449 | 38.146 | 39.530 | 34.01 |
| 136 | LEU | CA | 46.423 | 38.747 | 38.625 | 33.85 |
| 136 | LEU | CB | 45.798 | 38.886 | 37.229 | 33.98 |
| 136 | LEU | CG | 46.809 | 39.145 | 36.108 | 34.21 |
| 136 | LEU | CD1 | 47.681 | 37.906 | 35.869 | 34.29 |
| 136 | LEU | CD2 | 46.072 | 39.523 | 34.814 | 33.73 |
| 136 | LEU | C | 46.806 | 40.120 | 39.182 | 33.49 |
| 136 | LEU | O | 45.999 | 40.766 | 39.852 | 33.44 |
| 137 | ALA | N | 48.032 | 40.563 | 38.912 | 33.26 |
| 137 | ALA | CA | 48.501 | 41.858 | 39.402 | 33.14 |
| 137 | ALA | CB | 48.891 | 41.743 | 40.876 | 32.82 |
| 137 | ALA | C | 49.691 | 42.373 | 38.603 | 33.33 |
| 137 | ALA | O | 50.378 | 41.597 | 37.942 | 32.89 |
| 138 | TYR | N | 49.932 | 43.679 | 38.679 | 33.35 |
| 138 | TYR | CA | 51.051 | 44.300 | 37.967 | 34.13 |
| 138 | TYR | CB | 50.633 | 45.642 | 37.343 | 33.72 |
| 138 | TYR | CG | 49.420 | 45.578 | 36.435 | 34.20 |
| 138 | TYR | CD1 | 49.409 | 44.750 | 35.311 | 34.16 |
| 138 | TYR | CE1 | 48.314 | 44.718 | 34.444 | 34.48 |
| 138 | TYR | CD2 | 48.295 | 46.380 | 36.676 | 34.16 |
| 138 | TYR | CE2 | 47.192 | 46.359 | 35.812 | 34.13 |
| 138 | TYR | CZ | 47.209 | 45.526 | 34.700 | 34.39 |
| 138 | TYR | OH | 46.129 | 45.474 | 33.843 | 34.66 |
| 138 | TYR | C | 52.214 | 44.554 | 38.924 | 34.55 |
| 138 | TYR | O | 52.031 | 44.643 | 40.139 | 34.22 |
| 139 | GLY | N | 53.411 | 44.688 | 38.360 | 35.47 |
| 139 | GLY | CA | 54.582 | 44.949 | 39.173 | 36.62 |
| 139 | GLY | C | 55.701 | 43.955 | 38.966 | 37.31 |
| 139 | GLY | O | 56.866 | 44.278 | 39.201 | 37.52 |
| 140 | GLY | N | 55.364 | 42.753 | 38.509 | 38.05 |
| 140 | GLY | CA | 56.390 | 41.745 | 38.301 | 39.17 |
| 140 | GLY | C | 56.480 | 41.123 | 36.915 | 39.93 |
| 140 | GLY | O | 56.986 | 40.010 | 36.772 | 39.75 |
| 141 | SER | N | 56.005 | 41.830 | 35.892 | 40.71 |
| 141 | SER | CA | 56.047 | 41.310 | 34.521 | 41.34 |
| 141 | SER | CB | 54.726 | 40.612 | 34.171 | 41.61 |
| 141 | SER | OG | 53.644 | 41.531 | 34.107 | 41.68 |
| 141 | SER | C | 56.315 | 42.424 | 33.510 | 41.80 |
| 141 | SER | O | 55.864 | 43.556 | 33.690 | 41.68 |
| 142 | PRO | N | 57.042 | 42.112 | 32.418 | 42.10 |
| 142 | PRO | CD | 57.531 | 43.131 | 31.468 | 42.24 |
| 142 | PRO | CA | 57.606 | 40.797 | 32.089 | 42.58 |
| 142 | PRO | CB | 58.156 | 41.011 | 30.681 | 42.47 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| | | | | | | |
|---|---|---|---|---|---|---|
| 142 | PRO | CG | 58.675 | 42.413 | 30.770 | 42.16 |
| 142 | PRO | C | 58.695 | 40.313 | 33.053 | 42.97 |
| 142 | PRO | O | 59.102 | 39.148 | 33.000 | 43.23 |
| 143 | ARG | N | 59.167 | 41.204 | 33.922 | 43.15 |
| 143 | ARG | CA | 60.210 | 40.849 | 34.876 | 43.34 |
| 143 | ARG | CB | 61.586 | 41.240 | 34.315 | 43.34 |
| 143 | ARG | C | 59.975 | 41.523 | 36.230 | 43.27 |
| 143 | ARG | O | 59.069 | 42.353 | 36.380 | 43.08 |
| 144 | ALA | N | 60.792 | 41.161 | 37.217 | 43.16 |
| 144 | ALA | CA | 60.658 | 41.746 | 38.540 | 43.21 |
| 144 | ALA | CB | 61.685 | 41.136 | 39.500 | 43.24 |
| 144 | ALA | C | 60.846 | 43.258 | 38.457 | 43.31 |
| 144 | ALA | O | 61.550 | 43.759 | 37.578 | 43.14 |
| 145 | ASN | N | 60.197 | 43.968 | 39.377 | 43.45 |
| 145 | ASN | CA | 60.261 | 45.422 | 39.472 | 43.71 |
| 145 | ASN | CB | 61.657 | 45.857 | 39.936 | 43.64 |
| 145 | ASN | CG | 62.076 | 45.183 | 41.237 | 43.64 |
| 145 | ASN | OD1 | 62.790 | 44.185 | 41.227 | 43.65 |
| 145 | ASN | ND2 | 61.616 | 45.720 | 42.359 | 43.62 |
| 145 | ASN | C | 59.892 | 46.151 | 38.183 | 43.96 |
| 145 | ASN | O | 60.412 | 47.228 | 37.904 | 44.11 |
| 146 | SER | N | 58.986 | 45.568 | 37.406 | 44.30 |
| 146 | SER | CA | 58.561 | 46.178 | 36.149 | 44.53 |
| 146 | SER | CB | 58.053 | 45.095 | 35.194 | 44.90 |
| 146 | SER | OG | 57.994 | 45.580 | 33.861 | 45.57 |
| 146 | SER | C | 57.468 | 47.231 | 36.390 | 44.52 |
| 146 | SER | O | 57.213 | 47.616 | 37.536 | 44.02 |
| 147 | HIS | N | 56.838 | 47.693 | 35.306 | 44.59 |
| 147 | HIS | CA | 55.772 | 48.698 | 35.377 | 44.76 |
| 147 | HIS | CB | 55.110 | 48.913 | 34.014 | 45.09 |
| 147 | HIS | CG | 56.026 | 49.448 | 32.966 | 45.61 |
| 147 | HIS | CD2 | 56.441 | 50.712 | 32.701 | 45.76 |
| 147 | HIS | ND1 | 56.620 | 48.642 | 32.022 | 45.97 |
| 147 | HIS | CE1 | 57.360 | 49.383 | 31.216 | 46.05 |
| 147 | HIS | NE2 | 57.266 | 50.642 | 31.607 | 45.97 |
| 147 | HIS | C | 54.667 | 48.317 | 36.349 | 44.59 |
| 147 | HIS | O | 54.346 | 47.137 | 36.509 | 44.78 |
| 148 | GLY | N | 54.072 | 49.323 | 36.978 | 44.20 |
| 148 | GLY | CA | 52.992 | 49.056 | 37.905 | 43.92 |
| 148 | GLY | C | 53.439 | 48.669 | 39.297 | 43.71 |
| 148 | GLY | O | 54.623 | 48.746 | 39.643 | 43.63 |
| 149 | GLY | N | 52.481 | 48.226 | 40.101 | 43.39 |
| 149 | GLY | CA | 52.798 | 47.862 | 41.461 | 43.23 |
| 149 | GLY | C | 52.524 | 49.052 | 42.354 | 43.19 |
| 149 | GLY | O | 51.878 | 50.010 | 41.938 | 42.72 |
| 150 | VAL | N | 53.028 | 48.994 | 43.576 | 43.52 |
| 150 | VAL | CA | 52.813 | 50.047 | 44.557 | 44.13 |
| 150 | VAL | CB | 53.640 | 49.776 | 45.836 | 43.94 |
| 150 | VAL | CG1 | 53.225 | 48.426 | 46.429 | 43.80 |
| 150 | VAL | CG2 | 55.142 | 49.794 | 45.512 | 43.74 |
| 150 | VAL | C | 53.109 | 51.464 | 44.072 | 44.80 |
| 150 | VAL | O | 53.981 | 51.685 | 43.233 | 44.70 |
| 151 | CYS | N | 52.360 | 52.416 | 44.621 | 45.70 |
| 151 | CYS | CA | 52.490 | 53.833 | 44.301 | 46.52 |
| 151 | CYS | C | 51.926 | 54.161 | 42.928 | 46.62 |
| 151 | CYS | O | 52.421 | 53.688 | 41.910 | 46.64 |
| 151 | CYS | CB | 53.952 | 54.272 | 44.383 | 47.29 |
| 151 | CYS | SG | 54.701 | 54.094 | 46.035 | 48.62 |
| 152 | PRO | N | 50.881 | 54.996 | 42.885 | 46.88 |
| 152 | PRO | CD | 50.302 | 55.789 | 43.988 | 46.91 |
| 152 | PRO | CA | 50.275 | 55.360 | 41.608 | 47.02 |
| 152 | PRO | CB | 49.057 | 56.178 | 42.030 | 47.05 |
| 152 | PRO | CG | 49.553 | 56.888 | 43.248 | 46.98 |
| 152 | PRO | C | 51.227 | 56.152 | 40.715 | 47.22 |
| 152 | PRO | O | 51.923 | 57.058 | 41.170 | 47.34 |
| 153 | LYS | N | 51.271 | 55.768 | 39.449 | 47.40 |
| 153 | LYS | CA | 52.083 | 56.441 | 38.445 | 47.63 |
| 153 | LYS | CB | 53.417 | 55.730 | 38.211 | 48.04 |
| 153 | LYS | CG | 54.161 | 56.286 | 36.997 | 48.80 |
| 153 | LYS | CD | 55.514 | 55.622 | 36.766 | 49.22 |
| 153 | LYS | CE | 56.049 | 55.963 | 35.379 | 49.72 |
| 153 | LYS | NZ | 56.112 | 57.435 | 35.118 | 49.77 |
| 153 | LYS | C | 51.225 | 56.360 | 37.199 | 47.58 |
| 153 | LYS | O | 50.798 | 55.275 | 36.804 | 47.34 |
| 154 | ALA | N | 50.955 | 57.506 | 36.588 | 47.43 |
| 154 | ALA | CA | 50.107 | 57.533 | 35.411 | 47.58 |
| 154 | ALA | CB | 49.631 | 58.970 | 35.148 | 47.52 |
| 154 | ALA | C | 50.751 | 56.959 | 34.156 | 47.66 |
| 154 | ALA | O | 51.945 | 57.135 | 33.912 | 47.36 |
| 155 | TYR | N | 49.935 | 56.245 | 33.385 | 47.93 |
| 155 | TYR | CA | 50.332 | 55.663 | 32.108 | 48.40 |
| 155 | TYR | CB | 50.496 | 54.145 | 32.178 | 48.59 |
| 155 | TYR | CG | 51.659 | 53.666 | 33.007 | 48.89 |
| 155 | TYR | CD1 | 51.577 | 53.627 | 34.396 | 49.04 |
| 155 | TYR | CE1 | 52.648 | 53.180 | 35.172 | 49.22 |
| 155 | TYR | CD2 | 52.846 | 53.246 | 32.400 | 49.00 |
| 155 | TYR | CE2 | 53.923 | 52.797 | 33.166 | 49.11 |
| 155 | TYR | CZ | 53.815 | 52.765 | 34.553 | 49.11 |
| 155 | TYR | OH | 54.867 | 52.313 | 35.317 | 48.98 |
| 155 | TYR | C | 49.156 | 55.981 | 31.201 | 48.65 |
| 155 | TYR | O | 48.020 | 55.591 | 31.489 | 48.52 |
| 156 | TYR | N | 49.422 | 56.695 | 30.115 | 48.94 |
| 156 | TYR | CA | 48.362 | 57.068 | 29.196 | 49.32 |
| 156 | TYR | CB | 48.830 | 58.192 | 28.261 | 49.84 |
| 156 | TYR | CG | 47.712 | 58.733 | 27.392 | 50.40 |
| 156 | TYR | CD1 | 46.759 | 59.608 | 27.915 | 50.55 |
| 156 | TYR | CE1 | 45.697 | 60.059 | 27.141 | 50.83 |
| 156 | TYR | CD2 | 47.573 | 58.322 | 26.064 | 50.63 |
| 156 | TYR | CE2 | 46.511 | 58.763 | 25.283 | 50.88 |
| 156 | TYR | CZ | 45.579 | 59.629 | 25.827 | 50.96 |
| 156 | TYR | OH | 44.519 | 60.052 | 25.059 | 51.42 |
| 156 | TYR | C | 47.886 | 55.884 | 28.368 | 49.30 |
| 156 | TYR | O | 48.671 | 55.239 | 27.673 | 49.46 |
| 157 | SER | N | 46.595 | 55.595 | 28.453 | 49.12 |
| 157 | SER | CA | 46.010 | 54.509 | 27.688 | 49.10 |
| 157 | SER | CB | 44.894 | 53.839 | 28.489 | 48.89 |
| 157 | SER | OG | 44.305 | 52.779 | 27.759 | 48.59 |
| 157 | SER | C | 45.448 | 55.103 | 26.395 | 49.27 |
| 157 | SER | O | 44.431 | 55.794 | 26.412 | 49.40 |
| 158 | PRO | N | 46.126 | 54.865 | 25.259 | 49.31 |
| 158 | PRO | CD | 47.451 | 54.230 | 25.138 | 49.24 |
| 158 | PRO | CA | 45.680 | 55.382 | 23.959 | 49.35 |
| 158 | PRO | CB | 46.646 | 54.721 | 22.986 | 49.33 |
| 158 | PRO | CG | 47.923 | 54.721 | 23.781 | 49.38 |
| 158 | PRO | C | 44.225 | 55.043 | 23.668 | 49.29 |
| 158 | PRO | O | 43.462 | 55.901 | 23.228 | 49.38 |
| 159 | VAL | N | 43.841 | 53.796 | 23.918 | 49.12 |
| 159 | VAL | CA | 42.464 | 53.380 | 23.693 | 49.15 |
| 159 | VAL | CB | 42.311 | 51.848 | 23.780 | 49.15 |
| 159 | VAL | CG1 | 40.836 | 51.468 | 23.636 | 49.23 |
| 159 | VAL | CG2 | 43.119 | 51.183 | 22.673 | 49.17 |
| 159 | VAL | C | 41.543 | 54.018 | 24.736 | 49.15 |
| 159 | VAL | O | 40.398 | 54.357 | 24.445 | 49.18 |
| 160 | GLY | N | 42.049 | 54.178 | 25.953 | 49.05 |
| 160 | GLY | CA | 41.242 | 54.771 | 27.005 | 48.98 |
| 160 | GLY | C | 41.118 | 56.279 | 26.901 | 48.70 |
| 160 | GLY | O | 40.251 | 56.880 | 27.537 | 48.86 |
| 161 | LYS | N | 41.979 | 56.887 | 26.094 | 48.39 |
| 161 | LYS | CA | 41.984 | 58.331 | 25.914 | 48.06 |
| 161 | LYS | CB | 40.707 | 58.782 | 25.197 | 48.57 |
| 161 | LYS | CG | 40.574 | 58.210 | 23.792 | 49.22 |
| 161 | LYS | CD | 39.228 | 58.548 | 23.165 | 49.84 |
| 161 | LYS | CE | 39.116 | 57.933 | 21.776 | 50.37 |
| 161 | LYS | NZ | 37.765 | 58.122 | 21.153 | 50.81 |
| 161 | LYS | C | 42.113 | 59.041 | 27.252 | 47.59 |
| 161 | LYS | O | 41.632 | 60.163 | 27.417 | 47.67 |
| 162 | LYS | N | 42.763 | 58.384 | 28.210 | 46.75 |
| 162 | LYS | CA | 42.962 | 58.973 | 29.531 | 46.11 |
| 162 | LYS | CB | 41.665 | 58.937 | 30.349 | 46.11 |
| 162 | LYS | CG | 41.400 | 57.609 | 31.058 | 46.38 |
| 162 | LYS | CD | 40.277 | 57.753 | 32.073 | 46.41 |
| 162 | LYS | CE | 40.057 | 56.480 | 32.873 | 46.71 |
| 162 | LYS | NZ | 38.867 | 56.602 | 33.778 | 46.17 |
| 162 | LYS | C | 44.042 | 58.230 | 30.300 | 45.48 |
| 162 | LYS | O | 44.426 | 57.128 | 29.929 | 45.34 |
| 163 | ASN | N | 44.533 | 58.839 | 31.371 | 44.81 |
| 163 | ASN | CA | 45.544 | 58.185 | 32.184 | 44.41 |
| 163 | ASN | CB | 46.232 | 59.171 | 33.120 | 44.52 |
| 163 | ASN | CG | 47.001 | 60.220 | 32.380 | 44.76 |
| 163 | ASN | OD1 | 47.576 | 59.951 | 31.328 | 45.24 |
| 163 | ASN | ND2 | 47.032 | 61.425 | 32.926 | 44.78 |
| 163 | ASN | C | 44.912 | 57.090 | 33.022 | 43.96 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| | | | | | | |
|---|---|---|---|---|---|---|
| 163 | ASN | O | 43.740 | 57.160 | 33.399 | 43.97 |
| 164 | ILE | N | 45.702 | 56.066 | 33.299 | 43.24 |
| 164 | ILE | CA | 45.249 | 54.961 | 34.114 | 42.52 |
| 164 | ILE | CB | 44.841 | 53.761 | 33.239 | 42.41 |
| 164 | ILE | CG2 | 43.707 | 54.206 | 32.318 | 42.46 |
| 164 | ILE | CG1 | 46.040 | 53.223 | 32.447 | 42.23 |
| 164 | ILE | CD1 | 46.908 | 52.260 | 33.246 | 41.87 |
| 164 | ILE | C | 46.433 | 54.627 | 34.999 | 42.09 |
| 164 | ILE | O | 47.530 | 55.157 | 34.794 | 41.98 |
| 165 | TYR | N | 46.216 | 53.777 | 35.993 | 41.37 |
| 165 | TYR | CA | 47.300 | 53.410 | 36.881 | 40.63 |
| 165 | TYR | CB | 47.073 | 54.025 | 38.268 | 41.16 |
| 165 | TYR | CG | 46.943 | 55.538 | 38.225 | 41.76 |
| 165 | TYR | CD1 | 45.740 | 56.145 | 37.852 | 42.03 |
| 165 | TYR | CE1 | 45.632 | 57.531 | 37.738 | 42.27 |
| 165 | TYR | CD2 | 48.040 | 56.361 | 38.488 | 41.97 |
| 165 | TYR | CE2 | 47.946 | 57.754 | 38.373 | 42.23 |
| 165 | TYR | CZ | 46.735 | 58.328 | 37.995 | 42.58 |
| 165 | TYR | OH | 46.628 | 59.693 | 37.847 | 42.79 |
| 165 | TYR | C | 47.439 | 51.896 | 36.943 | 39.77 |
| 165 | TYR | O | 46.458 | 51.157 | 36.790 | 39.50 |
| 166 | LEU | N | 48.671 | 51.442 | 37.143 | 38.73 |
| 166 | LEU | CA | 48.959 | 50.015 | 37.202 | 37.71 |
| 166 | LEU | CB | 50.128 | 49.689 | 36.266 | 37.45 |
| 166 | LEU | CG | 49.830 | 50.047 | 34.805 | 37.43 |
| 166 | LEU | CD1 | 51.057 | 49.796 | 33.921 | 37.38 |
| 166 | LEU | CD2 | 48.640 | 49.243 | 34.283 | 37.14 |
| 166 | LEU | C | 49.286 | 49.560 | 38.621 | 37.06 |
| 166 | LEU | O | 49.983 | 48.566 | 38.819 | 36.54 |
| 167 | ASN | N | 48.799 | 50.312 | 39.604 | 36.57 |
| 167 | ASN | CA | 49.013 | 49.979 | 41.005 | 36.02 |
| 167 | ASN | CB | 49.129 | 51.264 | 41.835 | 35.90 |
| 167 | ASN | CG | 47.866 | 52.122 | 41.782 | 35.90 |
| 167 | ASN | OD1 | 47.078 | 52.047 | 40.835 | 35.38 |
| 167 | ASN | ND2 | 47.682 | 52.952 | 42.800 | 35.49 |
| 167 | ASN | C | 47.783 | 49.171 | 41.411 | 35.89 |
| 167 | ASN | O | 47.042 | 49.547 | 42.314 | 35.95 |
| 168 | SER | N | 47.582 | 48.042 | 40.742 | 35.61 |
| 168 | SER | CA | 46.409 | 47.231 | 41.009 | 35.49 |
| 168 | SER | CB | 45.273 | 47.715 | 40.124 | 35.83 |
| 168 | SER | OG | 45.729 | 47.807 | 38.786 | 36.17 |
| 168 | SER | C | 46.563 | 45.736 | 40.813 | 35.19 |
| 168 | SER | O | 47.544 | 45.248 | 40.247 | 34.75 |
| 169 | GLY | N | 45.548 | 45.023 | 41.285 | 34.71 |
| 169 | GLY | CA | 45.515 | 43.584 | 41.179 | 34.72 |
| 169 | GLY | C | 44.141 | 43.073 | 41.582 | 34.64 |
| 169 | GLY | O | 43.335 | 43.816 | 42.145 | 34.48 |
| 170 | LEU | N | 43.855 | 41.814 | 41.281 | 34.68 |
| 170 | LEU | CA | 42.561 | 41.251 | 41.645 | 34.73 |
| 170 | LEU | CB | 41.607 | 41.284 | 40.439 | 34.66 |
| 170 | LEU | CG | 42.086 | 40.441 | 39.249 | 34.68 |
| 170 | LEU | CD1 | 41.551 | 39.014 | 39.336 | 34.63 |
| 170 | LEU | CD2 | 41.609 | 41.063 | 37.932 | 35.09 |
| 170 | LEU | C | 42.673 | 39.833 | 42.189 | 34.65 |
| 170 | LEU | O | 43.635 | 39.103 | 41.916 | 34.21 |
| 171 | THR | N | 41.668 | 39.460 | 42.969 | 34.78 |
| 171 | THR | CA | 41.590 | 38.147 | 43.579 | 35.11 |
| 171 | THR | CB | 41.803 | 38.211 | 45.115 | 34.88 |
| 171 | THR | OG1 | 43.161 | 38.556 | 45.414 | 34.61 |
| 171 | THR | CG2 | 41.444 | 36.868 | 45.755 | 34.57 |
| 171 | THR | C | 40.192 | 37.606 | 43.344 | 35.57 |
| 171 | THR | O | 39.211 | 38.342 | 43.444 | 35.84 |
| 172 | SER | N | 40.101 | 36.323 | 43.023 | 36.15 |
| 172 | SER | CA | 38.806 | 35.684 | 42.821 | 36.77 |
| 172 | SER | CB | 38.679 | 35.115 | 41.405 | 36.76 |
| 172 | SER | OG | 37.490 | 34.342 | 41.298 | 36.64 |
| 172 | SER | C | 38.729 | 34.548 | 43.827 | 37.20 |
| 172 | SER | O | 39.711 | 33.830 | 44.031 | 37.07 |
| 173 | THR | N | 37.578 | 34.390 | 44.471 | 37.77 |
| 173 | THR | CA | 37.430 | 33.325 | 45.448 | 38.35 |
| 173 | THR | CB | 36.824 | 33.867 | 46.756 | 38.23 |
| 173 | THR | OG1 | 35.577 | 34.511 | 46.480 | 37.93 |
| 173 | THR | CG2 | 37.787 | 34.877 | 47.396 | 37.78 |
| 173 | THR | C | 36.581 | 32.165 | 44.915 | 39.17 |
| 173 | THR | O | 36.047 | 31.363 | 45.689 | 38.97 |
| 174 | LYS | N | 36.463 | 32.082 | 43.590 | 39.81 |
| 174 | LYS | CA | 35.717 | 31.006 | 42.948 | 40.76 |
| 174 | LYS | CB | 34.533 | 31.558 | 42.149 | 40.83 |
| 174 | LYS | CG | 33.657 | 30.477 | 41.497 | 41.18 |
| 174 | LYS | CD | 32.508 | 31.079 | 40.709 | 41.38 |
| 174 | LYS | CE | 31.724 | 30.009 | 39.943 | 41.88 |
| 174 | LYS | NZ | 30.543 | 30.600 | 39.218 | 42.08 |
| 174 | LYS | C | 36.664 | 30.275 | 42.006 | 41.39 |
| 174 | LYS | O | 37.503 | 30.896 | 41.359 | 41.31 |
| 175 | ASN | N | 36.530 | 28.957 | 41.932 | 42.11 |
| 175 | ASN | CA | 37.382 | 28.158 | 41.059 | 42.96 |
| 175 | ASN | CB | 38.770 | 27.983 | 41.691 | 42.77 |
| 175 | ASN | CG | 39.808 | 27.479 | 40.698 | 42.84 |
| 175 | ASN | OD1 | 39.721 | 27.752 | 39.501 | 42.69 |
| 175 | ASN | ND2 | 40.808 | 26.759 | 41.198 | 42.67 |
| 175 | ASN | C | 36.711 | 26.807 | 40.848 | 43.46 |
| 175 | ASN | O | 36.223 | 26.195 | 41.801 | 43.65 |
| 176 | TYR | N | 36.685 | 26.353 | 39.595 | 44.06 |
| 176 | TYR | CA | 36.055 | 25.083 | 39.245 | 44.41 |
| 176 | TYR | CB | 36.945 | 23.909 | 39.676 | 45.08 |
| 176 | TYR | CG | 38.335 | 23.920 | 39.054 | 45.89 |
| 176 | TYR | CD1 | 38.525 | 23.666 | 37.688 | 46.26 |
| 176 | TYR | CE1 | 39.810 | 23.693 | 37.120 | 46.51 |
| 176 | TYR | CD2 | 39.459 | 24.199 | 39.830 | 46.18 |
| 176 | TYR | CE2 | 40.736 | 24.229 | 39.270 | 46.46 |
| 176 | TYR | CZ | 40.903 | 23.978 | 37.923 | 46.52 |
| 176 | TYR | OH | 42.169 | 24.035 | 37.392 | 47.33 |
| 176 | TYR | C | 34.678 | 25.000 | 39.914 | 44.40 |
| 176 | TYR | O | 34.361 | 24.045 | 40.626 | 44.47 |
| 177 | GLY | N | 33.884 | 26.045 | 39.704 | 44.31 |
| 177 | GLY | CA | 32.536 | 26.102 | 40.244 | 43.91 |
| 177 | GLY | C | 32.340 | 26.213 | 41.750 | 43.76 |
| 177 | GLY | O | 31.208 | 26.389 | 42.206 | 43.81 |
| 178 | LYS | N | 33.415 | 26.122 | 42.526 | 43.32 |
| 178 | LYS | CA | 33.296 | 26.194 | 43.987 | 42.94 |
| 178 | LYS | CB | 33.913 | 24.934 | 44.617 | 43.40 |
| 178 | LYS | CG | 33.138 | 23.658 | 44.317 | 44.05 |
| 178 | LYS | CD | 33.875 | 22.393 | 44.750 | 44.34 |
| 178 | LYS | CE | 33.049 | 21.157 | 44.389 | 44.84 |
| 178 | LYS | NZ | 33.794 | 19.866 | 44.501 | 45.03 |
| 178 | LYS | C | 33.940 | 27.427 | 44.614 | 42.19 |
| 178 | LYS | O | 34.745 | 28.114 | 43.985 | 42.28 |
| 179 | THR | N | 33.548 | 27.719 | 45.850 | 41.39 |
| 179 | THR | CA | 34.142 | 28.824 | 46.584 | 40.46 |
| 179 | THR | CB | 33.265 | 29.251 | 47.765 | 40.32 |
| 179 | THR | OG1 | 32.033 | 29.780 | 47.269 | 40.47 |
| 179 | THR | CG2 | 33.972 | 30.317 | 48.605 | 40.08 |
| 179 | THR | C | 35.431 | 28.203 | 47.113 | 39.85 |
| 179 | THR | O | 35.396 | 27.107 | 47.666 | 39.95 |
| 180 | ILE | N | 36.563 | 28.877 | 46.929 | 38.94 |
| 180 | ILE | CA | 37.839 | 28.327 | 47.385 | 38.10 |
| 180 | ILE | CB | 39.037 | 29.046 | 46.706 | 37.98 |
| 180 | ILE | CG2 | 38.852 | 28.980 | 45.187 | 37.87 |
| 180 | ILE | CG1 | 39.152 | 30.489 | 47.215 | 37.90 |
| 180 | ILE | CD1 | 40.253 | 31.299 | 46.509 | 37.67 |
| 180 | ILE | C | 37.952 | 28.479 | 48.893 | 37.44 |
| 180 | ILE | O | 37.200 | 29.230 | 49.495 | 37.34 |
| 181 | LEU | N | 38.889 | 27.763 | 49.496 | 36.91 |
| 181 | LEU | CA | 39.090 | 27.836 | 50.940 | 36.32 |
| 181 | LEU | CB | 40.127 | 26.792 | 51.373 | 36.29 |
| 181 | LEU | CG | 39.647 | 25.347 | 51.160 | 36.15 |
| 181 | LEU | CD1 | 40.729 | 24.351 | 51.572 | 36.24 |
| 181 | LEU | CD2 | 38.370 | 25.075 | 51.970 | 36.93 |
| 181 | LEU | C | 39.559 | 29.236 | 51.333 | 35.93 |
| 181 | LEU | O | 40.141 | 29.951 | 50.519 | 35.92 |
| 182 | THR | N | 39.287 | 29.636 | 52.572 | 35.30 |
| 182 | THR | CA | 39.719 | 30.939 | 53.054 | 34.71 |
| 182 | THR | CB | 39.209 | 31.195 | 54.488 | 35.13 |
| 182 | THR | OG1 | 37.778 | 31.307 | 54.471 | 35.39 |
| 182 | THR | CG2 | 39.823 | 32.483 | 55.047 | 35.65 |
| 182 | THR | C | 41.255 | 30.998 | 53.045 | 34.02 |
| 182 | THR | O | 41.846 | 32.004 | 52.650 | 33.73 |
| 183 | LYS | N | 41.899 | 29.917 | 53.472 | 33.23 |
| 183 | LYS | CA | 43.353 | 29.876 | 53.497 | 32.54 |
| 183 | LYS | CB | 43.843 | 28.583 | 54.154 | 32.61 |
| 183 | LYS | CG | 43.545 | 27.315 | 53.371 | 32.68 |
| 183 | LYS | CD | 44.198 | 26.114 | 54.023 | 32.79 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| 183 | LYS | CE  | 44.147 | 24.900 | 53.111 | 33.20 |
| --- | --- | --- | ------ | ------ | ------ | ----- |
| 183 | LYS | NZ  | 44.906 | 23.737 | 53.680 | 33.32 |
| 183 | LYS | C   | 43.948 | 30.004 | 52.089 | 32.34 |
| 183 | LYS | O   | 45.078 | 30.476 | 51.936 | 31.99 |
| 184 | GLU | N   | 43.198 | 29.574 | 51.071 | 31.88 |
| 184 | GLU | CA  | 43.667 | 29.676 | 49.682 | 31.79 |
| 184 | GLU | CB  | 42.859 | 28.751 | 48.753 | 32.16 |
| 184 | GLU | CG  | 42.872 | 27.283 | 49.166 | 32.95 |
| 184 | GLU | CD  | 41.977 | 26.407 | 48.287 | 33.41 |
| 184 | GLU | OE1 | 40.936 | 26.893 | 47.825 | 33.91 |
| 184 | GLU | OE2 | 42.315 | 25.233 | 48.072 | 34.31 |
| 184 | GLU | C   | 43.503 | 31.126 | 49.239 | 31.34 |
| 184 | GLU | O   | 44.401 | 31.701 | 48.610 | 31.32 |
| 185 | ALA | N   | 42.368 | 31.723 | 49.596 | 30.75 |
| 185 | ALA | CA  | 42.088 | 33.121 | 49.249 | 30.21 |
| 185 | ALA | CB  | 40.708 | 33.523 | 49.772 | 30.06 |
| 185 | ALA | C   | 43.172 | 34.045 | 49.830 | 29.95 |
| 185 | ALA | O   | 43.603 | 34.997 | 49.183 | 29.57 |
| 186 | ASP | N   | 43.598 | 33.769 | 51.062 | 29.71 |
| 186 | ASP | CA  | 44.654 | 34.553 | 51.695 | 29.29 |
| 186 | ASP | CB  | 44.970 | 34.007 | 53.092 | 29.21 |
| 186 | ASP | CG  | 43.869 | 34.291 | 54.106 | 29.44 |
| 186 | ASP | OD1 | 42.860 | 34.927 | 53.751 | 28.72 |
| 186 | ASP | OD2 | 44.029 | 33.870 | 55.268 | 29.64 |
| 186 | ASP | C   | 45.927 | 34.477 | 50.856 | 29.17 |
| 186 | ASP | O   | 46.666 | 35.455 | 50.721 | 28.88 |
| 187 | LEU | N   | 46.192 | 33.295 | 50.316 | 29.08 |
| 187 | LEU | CA  | 47.386 | 33.079 | 49.511 | 29.71 |
| 187 | LEU | CB  | 47.648 | 31.564 | 49.358 | 30.11 |
| 187 | LEU | CG  | 47.946 | 30.921 | 50.728 | 31.10 |
| 187 | LEU | CD1 | 48.287 | 29.441 | 50.587 | 31.30 |
| 187 | LEU | CD2 | 49.106 | 31.640 | 51.419 | 31.18 |
| 187 | LEU | C   | 47.315 | 33.783 | 48.150 | 29.27 |
| 187 | LEU | O   | 48.301 | 34.350 | 47.700 | 29.26 |
| 188 | VAL | N   | 46.151 | 33.768 | 47.512 | 29.33 |
| 188 | VAL | CA  | 45.991 | 34.438 | 46.226 | 28.96 |
| 188 | VAL | CB  | 44.530 | 34.290 | 45.694 | 29.41 |
| 188 | VAL | CG1 | 44.379 | 35.028 | 44.356 | 29.10 |
| 188 | VAL | CG2 | 44.186 | 32.805 | 45.503 | 29.21 |
| 188 | VAL | C   | 46.321 | 35.929 | 46.410 | 28.70 |
| 188 | VAL | O   | 47.158 | 36.507 | 45.697 | 28.11 |
| 189 | THR | N   | 45.691 | 36.537 | 47.404 | 27.95 |
| 189 | THR | CA  | 45.910 | 37.949 | 47.670 | 27.87 |
| 189 | THR | CB  | 44.899 | 38.444 | 48.725 | 28.07 |
| 189 | THR | OG1 | 43.580 | 38.244 | 48.213 | 27.14 |
| 189 | THR | CG2 | 45.083 | 39.940 | 48.999 | 27.79 |
| 189 | THR | C   | 47.349 | 38.302 | 48.086 | 27.47 |
| 189 | THR | O   | 47.881 | 39.326 | 47.650 | 27.36 |
| 190 | THR | N   | 47.971 | 37.473 | 48.920 | 27.06 |
| 190 | THR | CA  | 49.349 | 37.721 | 49.356 | 26.95 |
| 190 | THR | CB  | 49.855 | 36.607 | 50.310 | 26.97 |
| 190 | THR | OG1 | 49.024 | 36.535 | 51.472 | 26.25 |
| 190 | THR | CG2 | 51.306 | 36.879 | 50.734 | 26.12 |
| 190 | THR | C   | 50.251 | 37.709 | 48.114 | 27.31 |
| 190 | THR | O   | 51.143 | 38.541 | 47.962 | 27.08 |
| 191 | HIS | N   | 49.988 | 36.747 | 47.234 | 27.47 |
| 191 | HIS | CA  | 50.740 | 36.558 | 45.991 | 27.77 |
| 191 | HIS | CB  | 50.303 | 35.248 | 45.326 | 27.41 |
| 191 | HIS | CG  | 50.934 | 34.995 | 43.990 | 27.50 |
| 191 | HIS | CD2 | 50.646 | 35.485 | 42.755 | 27.59 |
| 191 | HIS | ND1 | 51.950 | 34.083 | 43.810 | 27.34 |
| 191 | HIS | CE1 | 52.259 | 34.013 | 42.525 | 27.71 |
| 191 | HIS | NE2 | 51.479 | 34.853 | 41.856 | 27.92 |
| 191 | HIS | C   | 50.559 | 37.717 | 45.002 | 27.83 |
| 191 | HIS | O   | 51.530 | 38.199 | 44.423 | 28.20 |
| 192 | GLU | N   | 49.322 | 38.147 | 44.790 | 27.77 |
| 192 | GLU | CA  | 49.086 | 39.251 | 43.876 | 27.96 |
| 192 | GLU | CB  | 47.588 | 39.432 | 43.627 | 28.01 |
| 192 | GLU | CG  | 46.898 | 38.207 | 43.019 | 28.59 |
| 192 | GLU | CD  | 47.664 | 37.557 | 41.865 | 29.60 |
| 192 | GLU | OE1 | 48.456 | 38.259 | 41.177 | 29.97 |
| 192 | GLU | OE2 | 47.452 | 36.337 | 41.634 | 29.61 |
| 192 | GLU | C   | 49.723 | 40.529 | 44.439 | 27.98 |
| 192 | GLU | O   | 50.335 | 41.307 | 43.687 | 27.71 |
| 193 | LEU | N   | 49.594 | 40.742 | 45.751 | 27.68 |
| 193 | LEU | CA  | 50.207 | 41.908 | 46.376 | 27.69 |
| 193 | LEU | CB  | 49.813 | 42.035 | 47.854 | 27.93 |
| 193 | LEU | CG  | 48.343 | 42.445 | 48.037 | 28.23 |
| 193 | LEU | CD1 | 47.999 | 42.597 | 49.525 | 28.74 |
| 193 | LEU | CD2 | 48.052 | 43.752 | 47.305 | 28.07 |
| 193 | LEU | C   | 51.721 | 41.788 | 46.261 | 27.81 |
| 193 | LEU | O   | 52.419 | 42.799 | 46.182 | 27.59 |
| 194 | GLY | N   | 52.214 | 40.548 | 46.261 | 27.45 |
| 194 | GLY | CA  | 53.640 | 40.309 | 46.127 | 27.67 |
| 194 | GLY | C   | 54.145 | 40.860 | 44.805 | 27.89 |
| 194 | GLY | O   | 55.214 | 41.484 | 44.758 | 27.74 |
| 195 | HIS | N   | 53.387 | 40.618 | 43.730 | 28.34 |
| 195 | HIS | CA  | 53.728 | 41.138 | 42.409 | 28.91 |
| 195 | HIS | CB  | 52.722 | 40.684 | 41.344 | 28.90 |
| 195 | HIS | CG  | 52.885 | 39.265 | 40.904 | 29.19 |
| 195 | HIS | CD2 | 51.972 | 38.284 | 40.707 | 29.13 |
| 195 | HIS | ND1 | 54.107 | 38.728 | 40.555 | 29.27 |
| 195 | HIS | CE1 | 53.940 | 37.475 | 40.167 | 29.41 |
| 195 | HIS | NE2 | 52.653 | 37.181 | 40.252 | 29.67 |
| 195 | HIS | C   | 53.686 | 42.669 | 42.479 | 29.47 |
| 195 | HIS | O   | 54.517 | 43.357 | 41.876 | 29.42 |
| 196 | ASN | N   | 52.702 | 43.197 | 43.201 | 29.77 |
| 196 | ASN | CA  | 52.554 | 44.642 | 43.350 | 30.47 |
| 196 | ASN | CB  | 51.306 | 44.963 | 44.180 | 30.42 |
| 196 | ASN | CG  | 50.025 | 44.913 | 43.364 | 30.22 |
| 196 | ASN | OD1 | 48.930 | 44.822 | 43.919 | 30.73 |
| 196 | ASN | ND2 | 50.154 | 44.984 | 42.047 | 30.10 |
| 196 | ASN | C   | 53.784 | 45.215 | 44.033 | 30.97 |
| 196 | ASN | O   | 54.210 | 46.326 | 43.726 | 31.07 |
| 197 | PHE | N   | 54.332 | 44.460 | 44.983 | 31.16 |
| 197 | PHE | CA  | 55.527 | 44.893 | 45.683 | 32.11 |
| 197 | PHE | CB  | 55.654 | 44.211 | 47.056 | 32.06 |
| 197 | PHE | CG  | 54.897 | 44.909 | 48.160 | 32.49 |
| 197 | PHE | CD1 | 53.505 | 44.971 | 48.142 | 32.55 |
| 197 | PHE | CD2 | 55.575 | 45.481 | 49.233 | 32.76 |
| 197 | PHE | CE1 | 52.797 | 45.586 | 49.173 | 32.63 |
| 197 | PHE | CE2 | 54.876 | 46.102 | 50.275 | 32.94 |
| 197 | PHE | CZ  | 53.479 | 46.154 | 50.243 | 32.84 |
| 197 | PHE | C   | 56.770 | 44.604 | 44.839 | 32.36 |
| 197 | PHE | O   | 57.880 | 44.755 | 45.317 | 32.90 |
| 198 | GLY | N   | 56.566 | 44.169 | 43.597 | 32.88 |
| 198 | GLY | CA  | 57.672 | 43.913 | 42.683 | 33.15 |
| 198 | GLY | C   | 58.218 | 42.507 | 42.461 | 33.54 |
| 198 | GLY | O   | 59.084 | 42.313 | 41.595 | 33.69 |
| 199 | ALA | N   | 57.752 | 41.522 | 43.219 | 33.46 |
| 199 | ALA | CA  | 58.275 | 40.172 | 43.038 | 33.97 |
| 199 | ALA | CB  | 57.988 | 39.314 | 44.278 | 33.62 |
| 199 | ALA | C   | 57.723 | 39.486 | 41.802 | 34.11 |
| 199 | ALA | O   | 56.575 | 39.721 | 41.399 | 33.95 |
| 200 | GLU | N   | 58.567 | 38.668 | 41.173 | 34.47 |
| 200 | GLU | CA  | 58.142 | 37.884 | 40.021 | 34.84 |
| 200 | GLU | CB  | 59.177 | 37.931 | 38.876 | 36.00 |
| 200 | GLU | CG  | 60.553 | 37.335 | 39.156 | 37.49 |
| 200 | GLU | CD  | 61.565 | 37.624 | 38.028 | 38.44 |
| 200 | GLU | OE1 | 61.245 | 37.381 | 36.848 | 38.87 |
| 200 | GLU | OE2 | 62.680 | 38.093 | 38.330 | 39.55 |
| 200 | GLU | C   | 58.024 | 36.483 | 40.626 | 34.62 |
| 200 | GLU | O   | 58.230 | 36.312 | 41.827 | 33.71 |
| 201 | HIS | N   | 57.687 | 35.489 | 39.819 | 34.34 |
| 201 | HIS | CA  | 57.537 | 34.142 | 40.346 | 34.53 |
| 201 | HIS | CB  | 56.856 | 33.266 | 39.299 | 33.54 |
| 201 | HIS | CG  | 55.433 | 33.644 | 39.047 | 32.67 |
| 201 | HIS | CD2 | 54.541 | 34.303 | 39.824 | 32.28 |
| 201 | HIS | ND1 | 54.770 | 33.331 | 37.881 | 32.61 |
| 201 | HIS | CE1 | 53.530 | 33.783 | 37.946 | 32.40 |
| 201 | HIS | NE2 | 53.366 | 34.377 | 39.116 | 32.32 |
| 201 | HIS | C   | 58.842 | 33.498 | 40.796 | 35.26 |
| 201 | HIS | O   | 59.933 | 33.867 | 40.341 | 35.22 |
| 202 | ASP | N   | 58.727 | 32.559 | 41.728 | 36.11 |
| 202 | ASP | CA  | 59.894 | 31.828 | 42.187 | 36.98 |
| 202 | ASP | CB  | 59.589 | 31.079 | 43.488 | 36.36 |
| 202 | ASP | CG  | 59.438 | 32.010 | 44.670 | 35.88 |
| 202 | ASP | OD1 | 60.198 | 32.988 | 44.737 | 35.54 |
| 202 | ASP | OD2 | 58.575 | 31.767 | 45.534 | 35.71 |
| 202 | ASP | C   | 60.210 | 30.824 | 41.076 | 38.08 |
| 202 | ASP | O   | 59.331 | 30.459 | 40.305 | 37.52 |
| 203 | PRO | N   | 61.473 | 30.392 | 40.966 | 39.66 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| | | | | | | |
|---|---|---|---|---|---|---|
| 203 | PRO | CD | 62.651 | 30.883 | 41.699 | 40.16 |
| 203 | PRO | CA | 61.864 | 29.418 | 39.934 | 40.91 |
| 203 | PRO | CB | 63.353 | 29.233 | 40.180 | 40.99 |
| 203 | PRO | CG | 63.773 | 30.564 | 40.727 | 40.90 |
| 203 | PRO | C | 61.101 | 28.123 | 40.180 | 42.10 |
| 203 | PRO | O | 60.710 | 27.840 | 41.313 | 42.51 |
| 204 | ASP | N | 60.873 | 27.334 | 39.141 | 43.15 |
| 204 | ASP | CA | 60.152 | 26.079 | 39.338 | 44.22 |
| 204 | ASP | CB | 59.428 | 25.647 | 38.064 | 44.53 |
| 204 | ASP | CG | 60.385 | 25.360 | 36.925 | 44.89 |
| 204 | ASP | OD1 | 61.006 | 26.325 | 36.426 | 45.32 |
| 204 | ASP | OD2 | 60.525 | 24.179 | 36.531 | 45.28 |
| 204 | ASP | C | 61.085 | 24.958 | 39.768 | 44.93 |
| 204 | ASP | O | 62.308 | 25.133 | 39.868 | 44.76 |
| 205 | GLY | N | 60.486 | 23.798 | 40.024 | 45.69 |
| 205 | GLY | CA | 61.263 | 22.645 | 40.432 | 46.42 |
| 205 | GLY | C | 61.906 | 22.881 | 41.783 | 46.99 |
| 205 | GLY | O | 61.328 | 23.565 | 42.633 | 47.23 |
| 206 | LEU | N | 63.097 | 22.313 | 41.980 | 47.22 |
| 206 | LEU | CA | 63.837 | 22.458 | 43.235 | 47.38 |
| 206 | LEU | CB | 64.500 | 21.129 | 43.653 | 47.47 |
| 206 | LEU | CG | 64.965 | 21.114 | 45.126 | 47.66 |
| 206 | LEU | CD1 | 63.767 | 21.238 | 46.078 | 47.96 |
| 206 | LEU | CD2 | 65.719 | 19.822 | 45.451 | 47.67 |
| 206 | LEU | C | 64.914 | 23.540 | 43.111 | 47.44 |
| 206 | LEU | O | 65.730 | 23.555 | 42.179 | 47.57 |
| 207 | ALA | N | 64.909 | 24.449 | 44.070 | 47.44 |
| 207 | ALA | CA | 65.863 | 25.536 | 44.081 | 47.34 |
| 207 | ALA | CB | 65.447 | 26.596 | 43.058 | 47.44 |
| 207 | ALA | C | 65.849 | 26.111 | 45.484 | 47.34 |
| 207 | ALA | O | 65.042 | 25.715 | 46.322 | 47.46 |
| 208 | GLU | N | 66.755 | 27.037 | 45.749 | 47.42 |
| 208 | GLU | CA | 66.827 | 27.672 | 47.056 | 47.30 |
| 208 | GLU | CB | 68.024 | 28.621 | 47.062 | 48.01 |
| 208 | GLU | CG | 68.202 | 29.500 | 48.286 | 49.08 |
| 208 | GLU | CD | 69.296 | 30.532 | 48.053 | 49.75 |
| 208 | GLU | OE1 | 69.087 | 31.437 | 47.209 | 50.27 |
| 208 | GLU | OE2 | 70.370 | 30.430 | 48.693 | 50.06 |
| 208 | GLU | C | 65.518 | 28.437 | 47.308 | 46.98 |
| 208 | GLU | O | 65.086 | 28.599 | 48.448 | 46.85 |
| 209 | CYS | N | 64.886 | 28.885 | 46.225 | 46.21 |
| 209 | CYS | CA | 63.641 | 29.642 | 46.305 | 45.87 |
| 209 | CYS | C | 62.385 | 28.832 | 46.015 | 46.10 |
| 209 | CYS | O | 61.297 | 29.393 | 45.886 | 45.97 |
| 209 | CYS | CB | 63.704 | 30.828 | 45.344 | 44.89 |
| 209 | CYS | SG | 64.959 | 32.048 | 45.809 | 43.60 |
| 210 | ALA | N | 62.540 | 27.517 | 45.908 | 46.44 |
| 210 | ALA | CA | 61.421 | 26.623 | 45.644 | 47.08 |
| 210 | ALA | CB | 61.212 | 26.467 | 44.142 | 47.11 |
| 210 | ALA | C | 61.720 | 25.269 | 46.277 | 47.86 |
| 210 | ALA | O | 61.906 | 24.274 | 45.581 | 47.67 |
| 211 | PRO | N | 61.766 | 25.219 | 47.620 | 48.58 |
| 211 | PRO | CD | 61.587 | 26.356 | 48.540 | 48.62 |
| 211 | PRO | CA | 62.048 | 23.988 | 48.366 | 49.20 |
| 211 | PRO | CB | 61.955 | 24.439 | 49.823 | 49.08 |
| 211 | PRO | CG | 62.341 | 25.897 | 49.760 | 48.69 |
| 211 | PRO | C | 61.083 | 22.849 | 48.054 | 50.05 |
| 211 | PRO | O | 60.004 | 23.048 | 47.496 | 49.93 |
| 212 | ASN | N | 61.503 | 21.642 | 48.407 | 51.18 |
| 212 | ASN | CA | 60.706 | 20.439 | 48.206 | 52.30 |
| 212 | ASN | CB | 61.640 | 19.224 | 48.139 | 52.92 |
| 212 | ASN | CG | 62.555 | 19.117 | 49.364 | 53.44 |
| 212 | ASN | OD1 | 62.104 | 18.809 | 50.471 | 54.23 |
| 212 | ASN | ND2 | 63.844 | 19.382 | 49.169 | 53.84 |
| 212 | ASN | C | 59.773 | 20.312 | 49.416 | 52.71 |
| 212 | ASN | O | 59.964 | 20.993 | 50.424 | 52.73 |
| 213 | GLU | N | 58.783 | 19.432 | 49.328 | 53.24 |
| 213 | GLU | CA | 57.855 | 19.238 | 50.442 | 53.82 |
| 213 | GLU | CB | 56.958 | 18.033 | 50.171 | 54.25 |
| 213 | GLU | CG | 55.856 | 18.290 | 49.155 | 54.86 |
| 213 | GLU | CD | 54.935 | 17.087 | 48.983 | 55.49 |
| 213 | GLU | OE1 | 55.417 | 16.037 | 48.489 | 55.75 |
| 213 | GLU | OE2 | 53.735 | 17.182 | 49.344 | 55.69 |
| 213 | GLU | C | 58.534 | 19.065 | 51.813 | 53.91 |
| 213 | GLU | O | 58.130 | 19.704 | 52.798 | 54.01 |
| 214 | ASP | N | 59.551 | 18.202 | 51.889 | 53.72 |
| 214 | ASP | CA | 60.255 | 17.960 | 53.159 | 53.41 |
| 214 | ASP | CB | 61.297 | 16.847 | 53.000 | 54.15 |
| 214 | ASP | CG | 62.163 | 16.644 | 54.235 | 54.73 |
| 214 | ASP | OD1 | 61.678 | 16.044 | 55.225 | 55.16 |
| 214 | ASP | OD2 | 63.341 | 17.071 | 54.202 | 55.21 |
| 214 | ASP | C | 60.936 | 19.189 | 53.736 | 52.79 |
| 214 | ASP | O | 61.118 | 19.282 | 54.953 | 52.99 |
| 215 | GLN | N | 61.335 | 20.122 | 52.880 | 51.88 |
| 215 | GLN | CA | 61.974 | 21.331 | 53.383 | 50.96 |
| 215 | GLN | CB | 62.968 | 21.910 | 52.366 | 51.60 |
| 215 | GLN | CG | 63.931 | 22.928 | 52.975 | 52.22 |
| 215 | GLN | CD | 65.005 | 22.267 | 53.828 | 52.81 |
| 215 | GLN | OE1 | 64.703 | 21.457 | 54.714 | 53.24 |
| 215 | GLN | NE2 | 66.268 | 22.605 | 53.563 | 52.88 |
| 215 | GLN | C | 60.888 | 22.363 | 53.685 | 49.85 |
| 215 | GLN | O | 61.183 | 23.472 | 54.140 | 49.74 |
| 216 | GLY | N | 59.635 | 21.989 | 53.414 | 48.46 |
| 216 | GLY | CA | 58.515 | 22.880 | 53.679 | 46.62 |
| 216 | GLY | C | 57.625 | 23.281 | 52.506 | 45.32 |
| 216 | GLY | O | 56.666 | 24.037 | 52.692 | 44.87 |
| 217 | GLY | N | 57.928 | 22.793 | 51.303 | 43.79 |
| 217 | GLY | CA | 57.107 | 23.139 | 50.151 | 42.16 |
| 217 | GLY | C | 57.490 | 24.463 | 49.506 | 40.85 |
| 217 | GLY | O | 58.503 | 25.064 | 49.856 | 40.57 |
| 218 | LYS | N | 56.675 | 24.928 | 48.566 | 39.66 |
| 218 | LYS | CA | 56.962 | 26.180 | 47.869 | 38.74 |
| 218 | LYS | CB | 56.289 | 26.165 | 46.488 | 38.96 |
| 218 | LYS | CG | 56.559 | 24.907 | 45.658 | 39.24 |
| 218 | LYS | CD | 58.053 | 24.587 | 45.548 | 39.71 |
| 218 | LYS | CE | 58.283 | 23.288 | 44.756 | 39.75 |
| 218 | LYS | NZ | 59.659 | 22.715 | 44.945 | 40.80 |
| 218 | LYS | C | 56.540 | 27.456 | 48.627 | 37.69 |
| 218 | LYS | O | 55.681 | 27.412 | 49.504 | 37.33 |
| 219 | TYR | N | 57.171 | 28.579 | 48.280 | 36.44 |
| 219 | TYR | CA | 56.861 | 29.880 | 48.871 | 35.08 |
| 219 | TYR | CB | 58.081 | 30.790 | 48.826 | 35.14 |
| 219 | TYR | CG | 59.141 | 30.373 | 49.811 | 35.36 |
| 219 | TYR | CD1 | 58.947 | 30.542 | 51.184 | 35.32 |
| 219 | TYR | CE1 | 59.897 | 30.095 | 52.111 | 35.38 |
| 219 | TYR | CD2 | 60.314 | 29.749 | 49.380 | 35.55 |
| 219 | TYR | CE2 | 61.269 | 29.299 | 50.294 | 35.73 |
| 219 | TYR | CZ | 61.055 | 29.475 | 51.655 | 35.85 |
| 219 | TYR | OH | 62.012 | 29.037 | 52.552 | 35.93 |
| 219 | TYR | C | 55.687 | 30.502 | 48.117 | 34.52 |
| 219 | TYR | O | 55.322 | 30.036 | 47.035 | 33.65 |
| 220 | VAL | N | 55.103 | 31.552 | 48.689 | 33.96 |
| 220 | VAL | CA | 53.916 | 32.183 | 48.114 | 33.59 |
| 220 | VAL | CB | 53.419 | 33.356 | 49.003 | 33.34 |
| 220 | VAL | CG1 | 54.312 | 34.585 | 48.815 | 32.91 |
| 220 | VAL | CG2 | 51.963 | 33.673 | 48.659 | 32.96 |
| 220 | VAL | C | 53.999 | 32.657 | 46.665 | 33.69 |
| 220 | VAL | O | 52.982 | 32.665 | 45.961 | 33.62 |
| 221 | MET | N | 55.189 | 33.045 | 46.211 | 33.66 |
| 221 | MET | CA | 55.338 | 33.499 | 44.827 | 34.39 |
| 221 | MET | CB | 56.464 | 34.536 | 44.698 | 33.60 |
| 221 | MET | CG | 56.167 | 35.877 | 45.391 | 33.08 |
| 221 | MET | SD | 54.466 | 36.501 | 45.157 | 32.05 |
| 221 | MET | CE | 54.422 | 36.801 | 43.385 | 32.38 |
| 221 | MET | C | 55.548 | 32.371 | 43.811 | 35.23 |
| 221 | MET | O | 55.907 | 32.626 | 42.659 | 35.28 |
| 222 | TYR | N | 55.345 | 31.126 | 44.232 | 35.97 |
| 222 | TYR | CA | 55.463 | 30.014 | 43.298 | 36.93 |
| 222 | TYR | CB | 55.432 | 28.673 | 44.027 | 37.59 |
| 222 | TYR | CG | 55.974 | 27.540 | 43.187 | 38.08 |
| 222 | TYR | CD1 | 57.327 | 27.478 | 42.866 | 38.44 |
| 222 | TYR | CE1 | 57.832 | 26.463 | 42.052 | 38.71 |
| 222 | TYR | CD2 | 55.129 | 26.554 | 42.678 | 38.39 |
| 222 | TYR | CE2 | 55.621 | 25.533 | 41.868 | 38.73 |
| 222 | TYR | CZ | 56.976 | 25.498 | 41.559 | 39.11 |
| 222 | TYR | OH | 57.471 | 24.499 | 40.746 | 40.00 |
| 222 | TYR | C | 54.219 | 30.169 | 42.414 | 37.37 |
| 222 | TYR | O | 53.140 | 30.513 | 42.902 | 37.08 |
| 223 | PRO | N | 54.354 | 29.920 | 41.103 | 38.04 |
| 223 | PRO | CD | 55.614 | 29.584 | 40.418 | 38.08 |
| 223 | PRO | CA | 53.256 | 30.042 | 40.135 | 38.39 |
| 223 | PRO | CB | 53.979 | 29.955 | 38.796 | 38.48 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| | | | | | | |
|---|---|---|---|---|---|---|
| 223 | PRO | CG | 55.112 | 29.055 | 39.095 | 38.40 |
| 223 | PRO | C | 52.079 | 29.077 | 40.200 | 38.94 |
| 223 | PRO | O | 50.947 | 29.448 | 39.890 | 38.98 |
| 224 | ILE | N | 52.323 | 27.847 | 40.618 | 39.26 |
| 224 | ILE | CA | 51.244 | 26.886 | 40.628 | 40.09 |
| 224 | ILE | CB | 51.400 | 25.917 | 39.451 | 40.48 |
| 224 | ILE | CG2 | 50.837 | 26.567 | 38.185 | 40.60 |
| 224 | ILE | CG1 | 52.880 | 25.526 | 39.317 | 40.80 |
| 224 | ILE | CD1 | 53.147 | 24.535 | 38.211 | 41.41 |
| 224 | ILE | C | 51.056 | 26.058 | 41.873 | 40.24 |
| 224 | ILE | O | 51.989 | 25.821 | 42.638 | 40.30 |
| 225 | ALA | N | 49.816 | 25.614 | 42.034 | 40.58 |
| 225 | ALA | CA | 49.380 | 24.764 | 43.127 | 40.97 |
| 225 | ALA | CB | 49.722 | 23.308 | 42.795 | 41.20 |
| 225 | ALA | C | 49.825 | 25.070 | 44.556 | 41.21 |
| 225 | ALA | O | 49.990 | 24.139 | 45.343 | 41.39 |
| 226 | VAL | N | 50.037 | 26.330 | 44.920 | 41.25 |
| 226 | VAL | CA | 50.394 | 26.568 | 46.314 | 41.45 |
| 226 | VAL | CB | 51.272 | 27.840 | 46.493 | 41.51 |
| 226 | VAL | CG1 | 51.068 | 28.797 | 45.334 | 41.64 |
| 226 | VAL | CG2 | 50.969 | 28.515 | 47.827 | 41.44 |
| 226 | VAL | C | 49.057 | 26.630 | 47.072 | 41.43 |
| 226 | VAL | O | 48.406 | 27.669 | 47.171 | 41.19 |
| 227 | SER | N | 48.652 | 25.460 | 47.564 | 41.45 |
| 227 | SER | CA | 47.397 | 25.236 | 48.289 | 41.89 |
| 227 | SER | CB | 47.132 | 23.736 | 48.353 | 41.88 |
| 227 | SER | OG | 48.230 | 23.085 | 48.982 | 41.75 |
| 227 | SER | C | 47.298 | 25.775 | 49.708 | 41.96 |
| 227 | SER | O | 46.190 | 25.967 | 50.228 | 42.00 |
| 228 | GLY | N | 48.447 | 25.990 | 50.337 | 41.99 |
| 228 | GLY | CA | 48.466 | 26.463 | 51.709 | 42.37 |
| 228 | GLY | C | 48.642 | 25.275 | 52.635 | 42.72 |
| 228 | GLY | O | 48.721 | 25.426 | 53.853 | 42.58 |
| 229 | ASP | N | 48.710 | 24.087 | 52.037 | 43.09 |
| 229 | ASP | CA | 48.874 | 22.835 | 52.772 | 43.59 |
| 229 | ASP | CB | 48.539 | 21.636 | 51.884 | 44.44 |
| 229 | ASP | CG | 47.071 | 21.558 | 51.518 | 45.07 |
| 229 | ASP | OD1 | 46.698 | 20.559 | 50.856 | 46.12 |
| 229 | ASP | OD2 | 46.294 | 22.472 | 51.863 | 45.27 |
| 229 | ASP | C | 50.287 | 22.645 | 53.291 | 43.55 |
| 229 | ASP | O | 50.550 | 21.722 | 54.060 | 43.45 |
| 230 | HIS | N | 51.197 | 23.512 | 52.865 | 43.38 |
| 230 | HIS | CA | 52.586 | 23.411 | 53.287 | 43.24 |
| 230 | HIS | CB | 53.455 | 23.095 | 52.076 | 43.74 |
| 230 | HIS | CG | 53.018 | 21.863 | 51.355 | 44.30 |
| 230 | HIS | CD2 | 52.116 | 21.690 | 50.357 | 44.53 |
| 230 | HIS | ND1 | 53.423 | 20.601 | 51.728 | 44.35 |
| 230 | HIS | CE1 | 52.787 | 19.703 | 50.997 | 44.69 |
| 230 | HIS | NE2 | 51.988 | 20.339 | 50.158 | 44.94 |
| 230 | HIS | C | 53.064 | 24.673 | 53.975 | 42.89 |
| 230 | HIS | O | 52.631 | 25.780 | 53.637 | 42.41 |
| 231 | GLU | N | 53.963 | 24.484 | 54.939 | 42.49 |
| 231 | GLU | CA | 54.511 | 25.574 | 55.735 | 42.28 |
| 231 | GLU | CB | 55.656 | 25.064 | 56.625 | 43.29 |
| 231 | GLU | CG | 56.270 | 26.150 | 57.523 | 44.54 |
| 231 | GLU | CD | 57.300 | 25.603 | 58.521 | 45.36 |
| 231 | GLU | OE1 | 57.909 | 26.418 | 59.265 | 45.54 |
| 231 | GLU | OE2 | 57.492 | 24.365 | 58.558 | 45.66 |
| 231 | GLU | C | 55.001 | 26.786 | 54.957 | 41.71 |
| 231 | GLU | O | 54.627 | 27.915 | 55.277 | 41.40 |
| 232 | ASN | N | 55.833 | 26.563 | 53.941 | 40.80 |
| 232 | ASN | CA | 56.381 | 27.684 | 53.184 | 40.30 |
| 232 | ASN | CB | 57.548 | 27.228 | 52.289 | 40.22 |
| 232 | ASN | CG | 58.721 | 26.673 | 53.086 | 40.58 |
| 232 | ASN | OD1 | 59.053 | 27.175 | 54.157 | 40.38 |
| 232 | ASN | ND2 | 59.364 | 25.642 | 52.550 | 40.48 |
| 232 | ASN | C | 55.359 | 28.434 | 52.336 | 39.58 |
| 232 | ASN | O | 55.616 | 29.562 | 51.928 | 39.26 |
| 233 | ASN | N | 54.215 | 27.815 | 52.073 | 39.33 |
| 233 | ASN | CA | 53.182 | 28.447 | 51.252 | 39.40 |
| 233 | ASN | CB | 51.904 | 27.605 | 51.239 | 39.00 |
| 233 | ASN | CG | 52.081 | 26.256 | 50.543 | 38.74 |
| 233 | ASN | OD1 | 51.163 | 25.441 | 50.523 | 38.17 |
| 233 | ASN | ND2 | 53.259 | 26.021 | 49.973 | 38.66 |
| 233 | ASN | C | 52.832 | 29.863 | 51.702 | 39.53 |
| 233 | ASN | O | 52.547 | 30.719 | 50.871 | 39.63 |
| 234 | LYS | N | 52.867 | 30.101 | 53.012 | 39.81 |
| 234 | LYS | CA | 52.532 | 31.403 | 53.594 | 40.33 |
| 234 | LYS | CB | 51.901 | 31.226 | 54.978 | 40.90 |
| 234 | LYS | CG | 50.714 | 30.297 | 55.069 | 41.90 |
| 234 | LYS | CD | 50.448 | 30.006 | 56.544 | 42.73 |
| 234 | LYS | CE | 49.282 | 29.054 | 56.742 | 43.39 |
| 234 | LYS | NZ | 49.502 | 27.769 | 56.016 | 44.13 |
| 234 | LYS | C | 53.708 | 32.361 | 53.772 | 40.21 |
| 234 | LYS | O | 53.569 | 33.363 | 54.484 | 40.40 |
| 235 | MET | N | 54.860 | 32.066 | 53.173 | 39.47 |
| 235 | MET | CA | 56.014 | 32.946 | 53.333 | 39.09 |
| 235 | MET | CB | 57.052 | 32.289 | 54.244 | 40.17 |
| 235 | MET | CG | 56.465 | 31.689 | 55.512 | 41.84 |
| 235 | MET | SD | 57.740 | 30.990 | 56.579 | 44.64 |
| 235 | MET | CE | 58.083 | 29.387 | 55.761 | 43.33 |
| 235 | MET | C | 56.674 | 33.312 | 52.013 | 38.33 |
| 235 | MET | O | 56.446 | 32.657 | 50.988 | 37.96 |
| 236 | PHE | N | 57.490 | 34.360 | 52.046 | 37.26 |
| 236 | PHE | CA | 58.204 | 34.808 | 50.859 | 37.15 |
| 236 | PHE | CB | 58.372 | 36.326 | 50.881 | 36.44 |
| 236 | PHE | CG | 57.125 | 37.077 | 50.504 | 35.82 |
| 236 | PHE | CD1 | 56.721 | 37.153 | 49.172 | 35.71 |
| 236 | PHE | CD2 | 56.344 | 37.686 | 51.477 | 35.44 |
| 236 | PHE | CE1 | 55.554 | 37.832 | 48.816 | 35.24 |
| 236 | PHE | CE2 | 55.174 | 38.367 | 51.132 | 35.20 |
| 236 | PHE | CZ | 54.777 | 38.439 | 49.800 | 35.07 |
| 236 | PHE | C | 59.577 | 34.146 | 50.763 | 37.28 |
| 236 | PHE | O | 60.243 | 33.922 | 51.770 | 36.90 |
| 237 | SER | N | 59.987 | 33.823 | 49.541 | 37.66 |
| 237 | SER | CA | 61.284 | 33.205 | 49.312 | 38.05 |
| 237 | SER | CB | 61.321 | 32.542 | 47.935 | 38.00 |
| 237 | SER | OG | 61.120 | 33.505 | 46.917 | 37.41 |
| 237 | SER | C | 62.342 | 34.293 | 49.357 | 38.70 |
| 237 | SER | O | 62.024 | 35.486 | 49.375 | 38.35 |
| 238 | GLN | N | 63.601 | 33.869 | 49.379 | 39.50 |
| 238 | GLN | CA | 64.726 | 34.790 | 49.380 | 40.45 |
| 238 | GLN | CB | 66.048 | 34.010 | 49.458 | 41.34 |
| 238 | GLN | CG | 66.243 | 33.277 | 50.783 | 42.67 |
| 238 | GLN | CD | 66.412 | 34.242 | 51.951 | 43.54 |
| 238 | GLN | OE1 | 66.160 | 33.891 | 53.111 | 44.24 |
| 238 | GLN | NE2 | 66.849 | 35.468 | 51.649 | 43.86 |
| 238 | GLN | C | 64.671 | 35.590 | 48.085 | 40.43 |
| 238 | GLN | O | 65.017 | 36.769 | 48.059 | 40.66 |
| 239 | CYS | N | 64.225 | 34.939 | 47.013 | 40.63 |
| 239 | CYS | CA | 64.120 | 35.586 | 45.703 | 40.74 |
| 239 | CYS | C | 63.102 | 36.727 | 45.725 | 40.41 |
| 239 | CYS | O | 63.356 | 37.808 | 45.184 | 40.04 |
| 239 | CYS | CB | 63.739 | 34.559 | 44.628 | 41.45 |
| 239 | CYS | SG | 65.042 | 33.335 | 44.236 | 42.69 |
| 240 | SER | N | 61.954 | 36.479 | 46.349 | 40.19 |
| 240 | SER | CA | 60.910 | 37.493 | 46.462 | 40.29 |
| 240 | SER | CB | 59.643 | 36.882 | 47.071 | 40.08 |
| 240 | SER | OG | 59.074 | 35.910 | 46.215 | 39.76 |
| 240 | SER | C | 61.383 | 38.659 | 47.335 | 40.40 |
| 240 | SER | O | 61.078 | 39.823 | 47.053 | 40.33 |
| 241 | LYS | N | 62.127 | 38.339 | 48.391 | 40.50 |
| 241 | LYS | CA | 62.637 | 39.354 | 49.308 | 41.10 |
| 241 | LYS | CB | 63.365 | 38.698 | 50.481 | 40.76 |
| 241 | LYS | CG | 62.460 | 38.012 | 51.491 | 40.60 |
| 241 | LYS | CD | 63.282 | 37.429 | 52.628 | 40.39 |
| 241 | LYS | CE | 62.395 | 36.840 | 53.707 | 40.49 |
| 241 | LYS | NZ | 63.204 | 36.274 | 54.818 | 40.45 |
| 241 | LYS | C | 63.586 | 40.329 | 48.620 | 41.77 |
| 241 | LYS | O | 63.494 | 41.544 | 48.810 | 41.57 |
| 242 | GLN | N | 64.505 | 39.788 | 47.826 | 42.60 |
| 242 | GLN | CA | 65.470 | 40.613 | 47.113 | 43.55 |
| 242 | GLN | CB | 66.398 | 39.712 | 46.281 | 44.45 |
| 242 | GLN | CG | 67.611 | 40.417 | 45.716 | 45.86 |
| 242 | GLN | CD | 68.577 | 39.463 | 45.038 | 46.74 |
| 242 | GLN | OE1 | 68.199 | 38.719 | 44.133 | 47.71 |
| 242 | GLN | NE2 | 69.834 | 39.486 | 45.467 | 47.24 |
| 242 | GLN | C | 64.731 | 41.607 | 46.209 | 43.65 |
| 242 | GLN | O | 65.047 | 42.797 | 46.170 | 43.59 |
| 243 | SER | N | 63.734 | 41.113 | 45.485 | 43.77 |
| 243 | SER | CA | 62.961 | 41.959 | 44.588 | 43.87 |
| 243 | SER | CB | 62.028 | 41.092 | 43.740 | 43.76 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| | | | | | | |
|---|---|---|---|---|---|---|
| 243 | SER | OG | 62.771 | 40.173 | 42.961 | 43.31 |
| 243 | SER | C | 62.145 | 43.006 | 45.337 | 44.23 |
| 243 | SER | O | 62.098 | 44.171 | 44.940 | 44.17 |
| 244 | ILE | N | 61.510 | 42.588 | 46.427 | 44.68 |
| 244 | ILE | CA | 60.669 | 43.480 | 47.218 | 45.21 |
| 244 | ILE | CB | 59.730 | 42.656 | 48.137 | 44.81 |
| 244 | ILE | CG2 | 59.051 | 43.562 | 49.171 | 44.62 |
| 244 | ILE | CG1 | 58.717 | 41.909 | 47.258 | 44.59 |
| 244 | ILE | CD1 | 57.892 | 40.891 | 48.014 | 44.05 |
| 244 | ILE | C | 61.467 | 44.499 | 48.025 | 46.05 |
| 244 | ILE | O | 61.017 | 45.627 | 48.224 | 45.65 |
| 245 | TYR | N | 62.651 | 44.102 | 48.481 | 47.25 |
| 245 | TYR | CA | 63.511 | 45.006 | 49.233 | 48.50 |
| 245 | TYR | CB | 64.825 | 44.320 | 49.611 | 49.13 |
| 245 | TYR | CG | 65.755 | 45.191 | 50.434 | 49.90 |
| 245 | TYR | CD1 | 65.463 | 45.497 | 51.766 | 50.03 |
| 245 | TYR | CE1 | 66.312 | 46.302 | 52.526 | 50.40 |
| 245 | TYR | CD2 | 66.922 | 45.715 | 49.878 | 50.27 |
| 245 | TYR | CE2 | 67.781 | 46.527 | 50.630 | 50.62 |
| 245 | TYR | CZ | 67.471 | 46.815 | 51.952 | 50.61 |
| 245 | TYR | OH | 68.321 | 47.612 | 52.693 | 50.69 |
| 245 | TYR | C | 63.799 | 46.187 | 48.315 | 49.10 |
| 245 | TYR | O | 63.675 | 47.341 | 48.716 | 49.04 |
| 246 | LYS | N | 64.174 | 45.887 | 47.074 | 49.81 |
| 246 | LYS | CA | 64.452 | 46.927 | 46.090 | 50.75 |
| 246 | LYS | CB | 64.673 | 46.323 | 44.695 | 51.00 |
| 246 | LYS | CG | 65.982 | 45.571 | 44.502 | 51.59 |
| 246 | LYS | CD | 66.129 | 45.125 | 43.052 | 51.90 |
| 246 | LYS | CE | 67.416 | 44.357 | 42.830 | 52.28 |
| 246 | LYS | NZ | 67.560 | 43.948 | 41.403 | 52.33 |
| 246 | LYS | C | 63.273 | 47.890 | 46.023 | 51.14 |
| 246 | LYS | O | 63.440 | 49.103 | 46.118 | 51.15 |
| 247 | THR | N | 62.078 | 47.336 | 45.855 | 51.80 |
| 247 | THR | CA | 60.866 | 48.139 | 45.773 | 52.40 |
| 247 | THR | CB | 59.614 | 47.248 | 45.651 | 52.30 |
| 247 | THR | OG1 | 59.664 | 46.514 | 44.420 | 52.09 |
| 247 | THR | CG2 | 58.346 | 48.107 | 45.684 | 52.13 |
| 247 | THR | C | 60.702 | 49.033 | 46.998 | 53.14 |
| 247 | THR | O | 60.542 | 50.246 | 46.877 | 53.08 |
| 248 | ILE | N | 60.750 | 48.428 | 48.176 | 53.94 |
| 248 | ILE | CA | 60.583 | 49.178 | 49.408 | 54.96 |
| 248 | ILE | CB | 60.655 | 48.240 | 50.637 | 54.88 |
| 248 | ILE | CG2 | 60.528 | 49.057 | 51.925 | 54.90 |
| 248 | ILE | CG1 | 59.562 | 47.177 | 50.526 | 54.89 |
| 248 | ILE | CD1 | 59.554 | 46.217 | 51.686 | 54.95 |
| 248 | ILE | C | 61.593 | 50.314 | 49.570 | 55.69 |
| 248 | ILE | O | 61.207 | 51.454 | 49.833 | 55.77 |
| 249 | GLU | N | 62.877 | 50.027 | 49.393 | 56.54 |
| 249 | GLU | CA | 63.878 | 51.071 | 49.578 | 57.48 |
| 249 | GLU | CB | 65.289 | 50.469 | 49.652 | 58.05 |
| 249 | GLU | CG | 65.828 | 49.905 | 48.351 | 59.02 |
| 249 | GLU | CD | 67.257 | 49.398 | 48.493 | 59.54 |
| 249 | GLU | OE1 | 68.160 | 50.222 | 48.760 | 59.84 |
| 249 | GLU | OE2 | 67.476 | 48.175 | 48.345 | 60.02 |
| 249 | GLU | C | 63.843 | 52.193 | 48.543 | 57.80 |
| 249 | GLU | O | 64.546 | 53.192 | 48.693 | 57.86 |
| 250 | SER | N | 63.025 | 52.055 | 47.505 | 58.16 |
| 250 | SER | CA | 62.953 | 53.105 | 46.494 | 58.45 |
| 250 | SER | CB | 63.514 | 52.598 | 45.165 | 58.61 |
| 250 | SER | OG | 62.729 | 51.541 | 44.647 | 58.94 |
| 250 | SER | C | 61.554 | 53.672 | 46.269 | 58.59 |
| 250 | SER | O | 61.387 | 54.623 | 45.506 | 58.57 |
| 251 | LYS | N | 60.554 | 53.098 | 46.935 | 58.76 |
| 251 | LYS | CA | 59.172 | 53.554 | 46.781 | 58.85 |
| 251 | LYS | CB | 58.351 | 52.516 | 46.017 | 58.99 |
| 251 | LYS | CG | 58.596 | 52.438 | 44.520 | 59.31 |
| 251 | LYS | CD | 57.673 | 51.377 | 43.940 | 59.49 |
| 251 | LYS | CE | 57.609 | 51.388 | 42.423 | 59.66 |
| 251 | LYS | NZ | 56.579 | 50.404 | 41.938 | 59.42 |
| 251 | LYS | C | 58.474 | 53.839 | 48.106 | 58.77 |
| 251 | LYS | O | 57.508 | 54.597 | 48.152 | 58.81 |
| 252 | ALA | N | 58.945 | 53.217 | 49.179 | 58.69 |
| 252 | ALA | CA | 58.339 | 53.429 | 50.489 | 58.69 |
| 252 | ALA | CB | 59.160 | 52.721 | 51.573 | 58.66 |
| 252 | ALA | C | 58.273 | 54.926 | 50.772 | 58.54 |
| 252 | ALA | O | 57.297 | 55.431 | 51.331 | 58.67 |
| 253 | GLN | N | 59.320 | 55.635 | 50.364 | 58.33 |
| 253 | GLN | CA | 59.396 | 57.071 | 50.575 | 57.97 |
| 253 | GLN | CB | 60.815 | 57.559 | 50.278 | 58.55 |
| 253 | GLN | CG | 61.072 | 59.009 | 50.627 | 59.13 |
| 253 | GLN | CD | 60.856 | 59.299 | 52.101 | 59.51 |
| 253 | GLN | OE1 | 59.718 | 59.354 | 52.577 | 59.79 |
| 253 | GLN | NE2 | 61.952 | 59.480 | 52.835 | 59.76 |
| 253 | GLN | C | 58.399 | 57.788 | 49.676 | 57.38 |
| 253 | GLN | O | 57.889 | 58.856 | 50.024 | 57.51 |
| 254 | GLU | N | 58.114 | 57.180 | 48.528 | 56.50 |
| 254 | GLU | CA | 57.193 | 57.747 | 47.551 | 55.63 |
| 254 | GLU | CB | 57.363 | 57.039 | 46.204 | 56.07 |
| 254 | GLU | CG | 56.591 | 57.692 | 45.060 | 56.47 |
| 254 | GLU | CD | 56.739 | 56.943 | 43.746 | 56.78 |
| 254 | GLU | OE1 | 57.891 | 56.701 | 43.318 | 57.11 |
| 254 | GLU | OE2 | 55.702 | 56.602 | 43.139 | 56.77 |
| 254 | GLU | C | 55.709 | 57.735 | 47.941 | 54.80 |
| 254 | GLU | O | 55.030 | 58.753 | 47.801 | 54.58 |
| 255 | CYS | N | 55.195 | 56.602 | 48.422 | 53.66 |
| 255 | CYS | CA | 53.778 | 56.547 | 48.783 | 52.59 |
| 255 | CYS | C | 53.410 | 55.742 | 50.023 | 52.52 |
| 255 | CYS | O | 52.231 | 55.633 | 50.345 | 52.30 |
| 255 | CYS | CB | 52.954 | 56.028 | 47.603 | 51.44 |
| 255 | CYS | SG | 53.117 | 54.239 | 47.304 | 49.73 |
| 256 | PHE | N | 54.393 | 55.171 | 50.712 | 52.58 |
| 256 | PHE | CA | 54.095 | 54.408 | 51.922 | 52.90 |
| 256 | PHE | CB | 55.255 | 53.479 | 52.288 | 52.57 |
| 256 | PHE | CG | 55.233 | 52.163 | 51.570 | 52.17 |
| 256 | PHE | CD1 | 54.791 | 52.079 | 50.252 | 52.00 |
| 256 | PHE | CD2 | 55.701 | 51.013 | 52.194 | 51.99 |
| 256 | PHE | CE1 | 54.819 | 50.872 | 49.566 | 51.86 |
| 256 | PHE | CE2 | 55.733 | 49.797 | 51.512 | 51.86 |
| 256 | PHE | CZ | 55.291 | 49.728 | 50.196 | 51.82 |
| 256 | PHE | C | 53.832 | 55.376 | 53.066 | 53.32 |
| 256 | PHE | O | 54.473 | 56.421 | 53.164 | 53.19 |
| 257 | GLN | N | 52.888 | 55.022 | 53.930 | 53.81 |
| 257 | GLN | CA | 52.529 | 55.874 | 55.057 | 54.49 |
| 257 | GLN | CB | 51.075 | 56.327 | 54.924 | 54.41 |
| 257 | GLN | CG | 50.729 | 56.968 | 53.593 | 54.72 |
| 257 | GLN | CD | 49.269 | 57.361 | 53.509 | 54.80 |
| 257 | GLN | OE1 | 48.826 | 57.946 | 52.521 | 55.05 |
| 257 | GLN | NE2 | 48.510 | 57.038 | 54.549 | 54.80 |
| 257 | GLN | C | 52.683 | 55.125 | 56.369 | 54.95 |
| 257 | GLN | O | 53.133 | 53.981 | 56.396 | 55.09 |
| 258 | GLU | N | 52.309 | 55.788 | 57.458 | 55.42 |
| 258 | GLU | CA | 52.353 | 55.184 | 58.781 | 55.77 |
| 258 | GLU | CB | 52.566 | 56.261 | 59.851 | 56.14 |
| 258 | GLU | CG | 53.849 | 57.070 | 59.678 | 56.74 |
| 258 | GLU | CD | 54.055 | 58.095 | 60.779 | 57.19 |
| 258 | GLU | OE1 | 55.140 | 58.729 | 60.819 | 57.35 |
| 258 | GLU | OE2 | 53.129 | 58.270 | 61.606 | 57.42 |
| 258 | GLU | C | 50.973 | 54.554 | 58.949 | 55.81 |
| 258 | GLU | O | 50.057 | 54.864 | 58.185 | 55.77 |
| 259 | ARG | N | 50.814 | 53.664 | 59.921 | 55.84 |
| 259 | ARG | CA | 49.506 | 53.058 | 60.133 | 55.95 |
| 259 | ARG | CB | 49.577 | 51.980 | 61.212 | 55.87 |
| 259 | ARG | CG | 50.094 | 50.635 | 60.726 | 55.84 |
| 259 | ARG | CD | 50.023 | 49.614 | 61.849 | 55.69 |
| 259 | ARG | NE | 50.405 | 48.261 | 61.442 | 55.63 |
| 259 | ARG | CZ | 49.673 | 47.461 | 60.670 | 55.58 |
| 259 | ARG | NH1 | 48.498 | 47.860 | 60.196 | 55.45 |
| 259 | ARG | NH2 | 50.113 | 46.245 | 60.387 | 55.58 |
| 259 | ARG | C | 48.504 | 54.143 | 60.542 | 56.13 |
| 259 | ARG | O | 47.427 | 54.231 | 59.911 | 56.19 |
| 259 | ARG | OXT | 48.802 | 54.904 | 61.491 | 56.12 |
| 260 | 007 | N3 | 47.727 | 29.829 | 39.980 | 39.58 |
| 260 | 007 | O6 | 47.576 | 27.266 | 41.351 | 41.05 |
| 260 | 007 | O1 | 44.788 | 23.897 | 40.843 | 43.59 |
| 260 | 007 | C5 | 47.174 | 31.040 | 40.173 | 38.64 |
| 260 | 007 | O2 | 49.740 | 36.283 | 39.759 | 35.36 |
| 260 | 007 | C1 | 46.829 | 28.736 | 39.597 | 40.68 |
| 260 | 007 | C2 | 47.378 | 28.034 | 38.342 | 40.79 |
| 260 | 007 | C3 | 47.601 | 29.053 | 37.224 | 40.76 |
| 260 | 007 | C4 | 48.428 | 28.495 | 36.081 | 40.93 |
| 260 | 007 | C6 | 46.620 | 27.701 | 40.709 | 41.02 |
| 260 | 007 | C7 | 45.036 | 26.131 | 41.645 | 42.36 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| 260 | 007 | C8  | 44.100 | 26.443 | 42.823 | 42.38 |
| 260 | 007 | C13 | 44.799 | 27.056 | 44.045 | 42.39 |
| 260 | 007 | C20 | 46.068 | 26.282 | 44.406 | 42.54 |
| 260 | 007 | C21 | 43.850 | 27.067 | 45.249 | 42.60 |
| 260 | 007 | N1  | 48.734 | 35.382 | 39.482 | 36.20 |
| 260 | 007 | C9  | 49.235 | 34.151 | 39.306 | 36.48 |
| 260 | 007 | O3  | 50.444 | 33.937 | 39.245 | 35.65 |
| 260 | 007 | C10 | 48.255 | 33.016 | 39.175 | 37.20 |
| 260 | 007 | C22 | 48.177 | 32.158 | 40.439 | 38.16 |
| 260 | 007 | C23 | 47.749 | 32.989 | 41.665 | 37.95 |
| 260 | 007 | O4  | 45.975 | 31.286 | 40.126 | 38.63 |
| 260 | 007 | N2  | 45.330 | 27.355 | 40.904 | 41.60 |
| 260 | 007 | C11 | 44.380 | 25.075 | 40.766 | 42.75 |
| 260 | 007 | O5  | 43.453 | 25.430 | 40.003 | 43.03 |
| 260 | 007 | C14 | 47.884 | 32.183 | 42.942 | 38.16 |
| 260 | 007 | C15 | 49.090 | 32.237 | 43.694 | 38.38 |
| 260 | 007 | C16 | 49.209 | 31.514 | 44.917 | 38.20 |
| 260 | 007 | C17 | 48.120 | 30.724 | 45.385 | 38.22 |
| 260 | 007 | C18 | 46.921 | 30.645 | 44.623 | 38.22 |

TABLE 3-continued

COORDINATES for the COMPLEX of vgTACE with
N-{3-(Hydroxyaminocarbonyl)-1-Oxo-(2R)-Benzylpropyl}-Ile-Leu-OH

| 260 | 007 | C19    | 46.801 | 31.375 | 43.401 | 38.18 |
| 260 | 007 | C12    | 46.392 | 26.942 | 37.907 | 41.12 |
| 261 | ZN2 | ZN + 2 | 51.599 | 35.407 | 39.845 | 36.08 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are hereby incorporated by reference in their entireties.

What is claimed is:

1. A method for obtaining a crystal comprising a tumor necrosis factor-alpha (TACE): ligand complex between a substitute ligand and a modified TACE catalytic domain comprising:
   incubating an excess of a substitute ligand with a crystal comprising a modified TACE catalytic domain complexed to an initial ligand, wherein said modified TACE catalytic domain comprises SEQ ID NO: 8 and said crystal forms in space group $P2_12_12_1$ with unit cell dimensions of a=73, b=75 and c=103 Angstroms; and wherein said modified TACE catalytic domain
   catalyzes the proteolytic cleavage of SEQ ID NO: 17; and
   wherein said incubating is performed under appropriate conditions and for a sufficient time period for the substitute ligand to replace the initial ligand in the protein-ligand complex; and wherein a crystal comprising the protein-ligand complex between the substitute ligand and the modified TACE catalytic domain is obtained.

2. The method of claim 1 wherein the initial ligand is N-{D,L-2-(hydroxyaminocarbonyl)methyl-4-methylpentanoyl}-L-3-amino-2-dimethylbutanoyl-L-alanine, 2-(amino)ethyl amide.

3. The method of claim 1, wherein said modified TACE comprises the amino acid sequence of SEQ ID NO: 20.

4. The method of claim 1, wherein said modified TACE comprises the amino acid sequence of SEQ ID NO: 20.

5. The method of claim 1, wherein the amino acid residue at position 139 of SEQ ID NO: 8 is selected from the group consisting alanine, glycine and serine.

6. The method of claim 1, wherein the substitute ligand is N-{3-(hydroxyaminocarbonyl)-1-oxo-(2R)-benzylpropyl}-Ile-Leu-OH.

* * * * *

SEQUENCE LISTING

<160> NUMBER OF SEQ ID NOS: 20

<210> SEQ ID NO 1
<211> LENGTH: 1431
<212> TYPE: DNA
<213> ORGANISM: Homo sapiens

<400> SEQUENCE: 1

```
atgaggcagt ctctcctatt cctgaccagc gtggttcctt tcgtgctggc gccgcgacct      60
ccggatgacc cgggcttcgg cccccaccag aggctcgaga agcttgattc tttgctctca     120
gactacgata ttctctcttt atctaatatc cagcagcatt cggtaagaaa aagagatcta     180
cagacttcaa cacatgtaga aacactacta acttttcag ctttgaaaag gcattttaaa      240
ttatacctga catcaagtac tgaacgtttt tcacaaaatt tcaaggtcgt ggtggtggat     300
ggtaaaaacg aaagcgagta cactgtaaaa tggcaggact tcttcactgg acacgtggtt     360
ggtgagcctg actctagggt tctagcccac ataagagatg atgatgttat aatcagaatc     420
aacacagatg gggccgaata taacatagag ccactttgga gatttgttaa tgataccaaa     480
gacaaaagaa tgttagttta taaatctgaa gatatcaaga atgtttcacg tttgcagtct     540
ccaaaagtgt gtggttattt aaaagtggat aatgaagagt tgctcccaaa aggggttagta    600 gacagagaac cacctgaaga gcttgttcat cgagtgaaaa gaagagctga cccagatccc     660
atgaagaaca cgtgtaaatt attggtggta gcagatcatc gcttctacag atacatgggc     720
agaggggaag agagtacaac tacaaattac ttaatagagc taattgacag agttgatgac     780
atctatcgga cactgcatg ggataatgca ggttttaaag gctatggaat acagatagag     840
cagattcgca ttctcaagtc tccacaagag gtaaaacctg gtgaaaagca ctacaacatg     900
gcaaaaagtt acccaaatga agaaaaggat gcttgggatt gaagatgtt gctagagcaa      960 tttagctttg atatagctga ggaagcatct aaagtttgct tggcacacct tttcacatac    1020
caagattttg atatgggaac tcttggatta gcttatgttg gctctcccag agcaaacagc    1080
catggaggtg tttgtccaaa ggcttattat agcccagttg gaagaaaaa tatctatttg     1140 aatagtggtt tgacgagcac aaagaattat ggtaaaacca tccttacaaa ggaagctgac    1200
```

```
ctggttacaa ctcatgaatt gggacataat tttggagcag aacatgatcc ggatggtcta    1260
gcagaatgtg ccccgaatga ggaccaggga gggaaatatg tcatgtatcc catagctgtg    1320
agtggcgatc acgagaacaa taagatgttt tcacagtgca gtaaacaatc aatctataag    1380
accattgaaa gtaaggccca ggagtgtttt caagaacgca gcaataaagt t             1431
```

```
<210> SEQ ID NO 2
<211> LENGTH: 477
<212> TYPE: PRT
<213> ORGANISM: Homo sapiens

<400> SEQUENCE: 2

Met Arg Gln Ser Leu Leu Phe Leu Thr Ser Val Val Pro Phe Val Leu
1               5                   10                  15

Ala Pro Arg Pro Pro Asp Asp Pro Gly Phe Gly Pro His Gln Arg Leu
            20                  25                  30

Glu Lys Leu Asp Ser Leu Leu Ser Asp Tyr Asp Ile Leu Ser Leu Ser
        35                  40                  45

Asn Ile Gln Gln His Ser Val Arg Lys Arg Asp Leu Gln Thr Ser Thr
50                  55                  60

His Val Glu Thr Leu Leu Thr Phe Ser Ala Leu Lys Arg His Phe Lys
65                  70                  75                  80

Leu Tyr Leu Thr Ser Ser Thr Glu Arg Phe Ser Gln Asn Phe Lys Val
                85                  90                  95

Val Val Val Asp Gly Lys Asn Glu Ser Glu Tyr Thr Val Lys Trp Gln
            100                 105                 110

Asp Phe Phe Thr Gly His Val Val Gly Glu Pro Asp Ser Arg Val Leu
        115                 120                 125

Ala His Ile Arg Asp Asp Asp Val Ile Ile Arg Ile Asn Thr Asp Gly
130                 135                 140

Ala Glu Tyr Asn Ile Glu Pro Leu Trp Arg Phe Val Asn Asp Thr Lys
145                 150                 155                 160

Asp Lys Arg Met Leu Val Tyr Lys Ser Glu Asp Ile Lys Asn Val Ser
                165                 170                 175

Arg Leu Gln Ser Pro Lys Val Cys Gly Tyr Leu Lys Val Asp Asn Glu
            180                 185                 190

Glu Leu Leu Pro Lys Gly Leu Val Asp Arg Glu Pro Pro Glu Glu Leu
        195                 200                 205

Val His Arg Val Lys Arg Ala Asp Pro Asp Pro Met Lys Asn Thr
210                 215                 220

Cys Lys Leu Leu Val Val Ala Asp His Arg Phe Tyr Arg Tyr Met Gly
225                 230                 235                 240

Arg Gly Glu Glu Ser Thr Thr Thr Asn Tyr Leu Ile Glu Leu Ile Asp
                245                 250                 255

Arg Val Asp Asp Ile Tyr Arg Asn Thr Ala Trp Asp Asn Ala Gly Phe
            260                 265                 270

Lys Gly Tyr Gly Ile Gln Ile Glu Gln Ile Arg Ile Leu Lys Ser Pro
        275                 280                 285

Gln Glu Val Lys Pro Gly Glu Lys His Tyr Asn Met Ala Lys Ser Tyr
    290                 295                 300

Pro Asn Glu Glu Lys Asp Ala Trp Asp Val Lys Met Leu Leu Glu Gln
305                 310                 315                 320

Phe Ser Phe Asp Ile Ala Glu Glu Ala Ser Lys Val Cys Leu Ala His
                325                 330                 335
```

```
Leu Phe Thr Tyr Gln Asp Phe Asp Met Gly Thr Leu Gly Leu Ala Tyr
            340                 345                 350

Val Gly Ser Pro Arg Ala Asn Ser His Gly Val Cys Pro Lys Ala
            355                 360             365

Tyr Tyr Ser Pro Val Gly Lys Lys Asn Ile Tyr Leu Asn Ser Gly Leu
            370                 375                 380

Thr Ser Thr Lys Asn Tyr Gly Lys Thr Ile Leu Thr Lys Glu Ala Asp
385                 390                 395                 400

Leu Val Thr Thr His Glu Leu Gly His Asn Phe Gly Ala Glu His Asp
                405                 410                 415

Pro Asp Gly Leu Ala Glu Cys Ala Pro Asn Glu Asp Gln Gly Gly Lys
            420                 425                 430

Tyr Val Met Tyr Pro Ile Ala Val Ser Gly Asp His Glu Asn Asn Lys
            435                 440                 445

Met Phe Ser Gln Cys Ser Lys Gln Ser Ile Tyr Lys Thr Ile Glu Ser
            450                 455                 460

Lys Ala Gln Glu Cys Phe Gln Glu Arg Ser Asn Lys Val
465                 470                 475

<210> SEQ ID NO 3
<211> LENGTH: 1380
<212> TYPE: DNA
<213> ORGANISM: Homo sapiens

<400> SEQUENCE: 3
ccgcgacctc cggatgaccc gggcttcggc ccccaccaga ggctcgagaa gcttgattct      60
ttgctctcag actacgatat tctctcttta tctaatatcc agcagcattc ggtaagaaaa     120
agagatctac agacttcaac acatgtagaa acactactaa cttttcagc tttgaaaagg     180 cattttaaat tataccctgac atcaagtact gaacgttttt cacaaaattt caaggtcgtg     240
gtggtggatg gtaaaaacga agcgagtac actgtaaaat ggcaggactt cttcactgga     300
cacgtggttg gtgagcctga ctctagggtt ctagcccaca taagagatga tgatgttata     360
atcagaatca acacagatgg ggccgaatat aacatagagc cactttggag atttgttaat     420
gataccaaag acaaagaat gttagtttat aaatctgaag atatcaagaa tgtttcacgt     480
ttgcagtctc caaaagtgtg tggttattta aaagtggata atgaagagtt gctcccaaaa     540
gggttagtag acagagaacc acctgaagag cttgttcatc gagtgaaaag aagagctgac     600
ccagatccca tgaagaacac gtgtaaatta ttggtggtag cagatcatcg cttctacaga     660
tacatgggca gaggggaaga gagtacaact acaaattact taatagagct aattgacaga     720
gttgatgaca tctatcggaa cactgcatgg gataatgcag ttttaaagg ctatggaata     780 cagatagagc agattcgcat tctcaagtct ccacaagagg taaacctgg tgaaagcac     840 tacaacatga caaaagtta cccaaatgaa gaaaggatg cttgggatgt gaagatgttg     900
ctagagcaat ttagctttga tatagctgag gaagcatcta agttttgctt ggcacacctt     960
ttcacatacc aagattttga tatgggaact cttggattag cttatgttgg ctctcccaga    1020
gcaaacagcc atggaggtgt ttgtccaaag gcttattata gcccagttgg gaagaaaaat    1080
atctatttga atagtggttt gacgagcaca aagaattatg gtaaaaccat ccttacaaag    1140
gaagctgacc tggttacaac tcatgaattg ggacataatt ttggagcaga acatgatccg    1200
gatggtctag cagaatgtgc cccgaatgag gaccagggag ggaaatatgt catgtatccc    1260
atagctgtga gtggcgatca cgagaacaat aagatgtttt cacagtgcag taaacaatca    1320
```
atctataaga ccattgaaag taaggcccag gagtgttttc aagaacgcag caataaagtt    1380

<210> SEQ ID NO 4
<211> LENGTH: 460
<212> TYPE: PRT
<213> ORGANISM: Homo sapiens

<400> SEQUENCE: 4

Pro Arg Pro Pro Asp Asp Pro Gly Phe Gly Pro His Gln Arg Leu Glu
1               5                   10                  15

Lys Leu Asp Ser Leu Leu Ser Asp Tyr Asp Ile Leu Ser Leu Ser Asn
            20                  25                  30

Ile Gln Gln His Ser Val Arg Lys Arg Asp Leu Gln Thr Ser Thr His
        35                  40                  45

Val Glu Thr Leu Leu Thr Phe Ser Ala Leu Lys Arg His Phe Lys Leu
    50                  55                  60

Tyr Leu Thr Ser Ser Thr Glu Arg Phe Ser Gln Asn Phe Lys Val Val
65                  70                  75                  80

Val Val Asp Gly Lys Asn Glu Ser Glu Tyr Thr Val Lys Trp Gln Asp
                85                  90                  95

Phe Phe Thr Gly His Val Val Gly Glu Pro Asp Ser Arg Val Leu Ala
            100                 105                 110

His Ile Arg Asp Asp Val Ile Ile Arg Ile Asn Thr Asp Gly Ala
        115                 120                 125

Glu Tyr Asn Ile Glu Pro Leu Trp Arg Phe Val Asn Asp Thr Lys Asp
    130                 135                 140

Lys Arg Met Leu Val Tyr Lys Ser Glu Asp Ile Lys Asn Val Ser Arg
145                 150                 155                 160

Leu Gln Ser Pro Lys Val Cys Gly Tyr Leu Lys Val Asp Asn Glu Glu
                165                 170                 175

Leu Leu Pro Lys Gly Leu Val Asp Arg Glu Pro Glu Glu Leu Val
            180                 185                 190

His Arg Val Lys Arg Arg Ala Asp Pro Asp Pro Met Lys Asn Thr Cys
        195                 200                 205

Lys Leu Leu Val Val Ala Asp His Arg Phe Tyr Arg Tyr Met Gly Arg
    210                 215                 220

Gly Glu Glu Ser Thr Thr Thr Asn Tyr Leu Ile Glu Leu Ile Asp Arg
225                 230                 235                 240

Val Asp Asp Ile Tyr Arg Asn Thr Ala Trp Asp Asn Ala Gly Phe Lys
                245                 250                 255

Gly Tyr Gly Ile Gln Ile Glu Gln Ile Arg Ile Leu Lys Ser Pro Gln
            260                 265                 270

Glu Val Lys Pro Gly Glu Lys His Tyr Asn Met Ala Lys Ser Tyr Pro
        275                 280                 285

Asn Glu Glu Lys Asp Ala Trp Asp Val Lys Met Leu Leu Glu Gln Phe
    290                 295                 300

Ser Phe Asp Ile Ala Glu Glu Ala Ser Lys Val Cys Leu Ala His Leu
305                 310                 315                 320

Phe Thr Tyr Gln Asp Phe Asp Met Gly Thr Leu Gly Leu Ala Tyr Val
                325                 330                 335

Gly Ser Pro Arg Ala Asn Ser His Gly Gly Val Cys Pro Lys Ala Tyr
            340                 345                 350

Tyr Ser Pro Val Gly Lys Lys Asn Ile Tyr Leu Asn Ser Gly Leu Thr
        355                 360                 365

Ser Thr Lys Asn Tyr Gly Lys Thr Ile Leu Thr Lys Glu Ala Asp Leu
        370                 375                 380

Val Thr Thr His Glu Leu Gly His Asn Phe Gly Ala Glu His Asp Pro
385                 390                 395                 400

Asp Gly Leu Ala Glu Cys Ala Pro Asn Glu Asp Gln Gly Gly Lys Tyr
                405                 410                 415

Val Met Tyr Pro Ile Ala Val Ser Gly Asp His Glu Asn Asn Lys Met
                420                 425                 430

Phe Ser Gln Cys Ser Lys Gln Ser Ile Tyr Lys Thr Ile Glu Ser Lys
            435                 440                 445

Ala Gln Glu Cys Phe Gln Glu Arg Ser Asn Lys Val
        450                 455                 460

<210> SEQ ID NO 5
<211> LENGTH: 789
<212> TYPE: DNA
<213> ORGANISM: Homo sapiens

<400> SEQUENCE: 5
agagctgacc cagatcccat gaagaacacg tgtaaattat tggtggtagc agatcatcgc      60
ttctacagat acatgggcag aggggaagag agtacaacta caaattactt aatagagcta     120
attgacagag ttgatgacat ctatcggaac actgcatggg ataatgcagg ttttaaaggc     180
tatggaatac agatagagca gattcgcatt ctcaagtctc cacaagaggt aaaacctggt     240
gaaaagcact acaacatggc aaaaagttac ccaaatgaag aaaaggatgc ttgggatgtg     300
aagatgttgc tagagcaatt tagctttgat atagctgagg aagcatctaa agtttgcttg     360
gcacaccttt tcacatacca agattttgat atgggaactc ttggattagc ttatgttggc     420
tctcccagag caaacagcca tggaggtgtt tgtccaaagg cttattatag cccagttggg     480
aagaaaaata tctatttgaa tagtggtttg acgagcacaa gaattatgg taaaaccatc     540 cttacaaagg aagctgacct ggttacaact catgaattgg gacataattt tggagcagaa     600
catgatccgg atggtctagc agaatgtgcc ccgaatgagg accagggagg gaaatatgtc     660
atgtatccca tagctgtgag tggcgatcac gagaacaata gatgttttc acagtgcagt     720 aaacaatcaa tctataagac cattgaaagt aaggcccagg agtgttttca gaacgcagc     780 aataaagtt                                                             789

<210> SEQ ID NO 6
<211> LENGTH: 263
<212> TYPE: PRT
<213> ORGANISM: Homo sapiens

<400> SEQUENCE: 6

Arg Ala Asp Pro Asp Pro Met Lys Asn Thr Cys Lys Leu Leu Val Val
1               5                   10                  15

Ala Asp His Arg Phe Tyr Arg Tyr Met Gly Arg Gly Glu Glu Ser Thr
            20                  25                  30

Thr Thr Asn Tyr Leu Ile Glu Leu Ile Asp Arg Val Asp Asp Ile Tyr
        35                  40                  45

Arg Asn Thr Ala Trp Asp Asn Ala Gly Phe Lys Gly Tyr Gly Ile Gln
    50                  55                  60

Ile Glu Gln Ile Arg Ile Leu Lys Ser Pro Gln Glu Val Lys Pro Gly
65                  70                  75                  80

Glu Lys His Tyr Asn Met Ala Lys Ser Tyr Pro Asn Glu Glu Lys Asp

```
                85                  90                  95
Ala Trp Asp Val Lys Met Leu Leu Glu Gln Phe Ser Phe Asp Ile Ala
            100                 105                 110
Glu Glu Ala Ser Lys Val Cys Leu Ala His Leu Phe Thr Tyr Gln Asp
            115                 120                 125
Phe Asp Met Gly Thr Leu Gly Leu Ala Tyr Val Gly Ser Pro Arg Ala
            130                 135                 140
Asn Ser His Gly Gly Val Cys Pro Lys Ala Tyr Tyr Ser Pro Val Gly
145                 150                 155                 160
Lys Lys Asn Ile Tyr Leu Asn Ser Gly Leu Thr Ser Thr Lys Asn Tyr
                165                 170                 175
Gly Lys Thr Ile Leu Thr Lys Glu Ala Asp Leu Val Thr Thr His Glu
            180                 185                 190
Leu Gly His Asn Phe Gly Ala Glu His Asp Pro Asp Gly Leu Ala Glu
            195                 200                 205
Cys Ala Pro Asn Glu Asp Gln Gly Gly Lys Tyr Val Met Tyr Pro Ile
            210                 215                 220
Ala Val Ser Gly Asp His Glu Asn Asn Lys Met Phe Ser Gln Cys Ser
225                 230                 235                 240
Lys Gln Ser Ile Tyr Lys Thr Ile Glu Ser Lys Ala Gln Glu Cys Phe
                245                 250                 255
Gln Glu Arg Ser Asn Lys Val
            260
```

<210> SEQ ID NO 7
<211> LENGTH: 789
<212> TYPE: DNA
<213> ORGANISM: Homo sapiens
<220> FEATURE:
<221> NAME/KEY: misc_feature
<222> LOCATION: (415)..(417)
<223> OTHER INFORMATION: nnn is a codon that encodes an amino acid
      selected from: A, R, N, D, C, E, Q, G, H, K, P, S, T, Y

<400> SEQUENCE: 7

```
agagctgacc cagatcccat gaagaacacg tgtaaattat tggtggtagc agatcatcgc    60
ttctacagat acatgggcag aggggaagag agtacaacta caaattactt aatagagcta   120
attgacagag ttgatgacat ctatcggaac actgcatggg ataatgcagg ttttaaaggc   180
tatggaatac agatagagca gattcgcatt ctcaagtctc cacaagaggt aaaacctggt   240
gaaaagcact acaacatggc aaaaagttac ccaaatgaag aaaaggatgc ttgggatgtg   300
aagatgttgc tagagcaatt tagctttgat atagctgagg aagcatctaa agtttgcttg   360
gcacaccttt tcacatacca agattttgat atgggaactc ttggattagc ttatnnnggc   420
tctcccagag caaacagcca tggaggtgtt tgtccaaagg cttattatag cccagttggg   480
aagaaaaata tctatttgaa tagtggtttg acgagcacaa agaattatgg taaaaccatc   540
cttacaaagg aagctgacct ggttacaact catgaattgg gacataattt tggagcagaa   600
catgatccgg atggtctagc agaatgtgcc ccgaatgagg accagggagg gaaatatgtc   660
atgtatccca tagctgtgag tggcgatcac gagaacaata agatgttttc acagtgcagt   720
aaacaatcaa tctataagac cattgaaagt aaggcccagg agtgttttca agaacgcagc   780
aataaagtt                                                           789
```

<210> SEQ ID NO 8
<211> LENGTH: 263

```
<212> TYPE: PRT
<213> ORGANISM: Homo sapiens
<220> FEATURE:
<221> NAME/KEY: MISC_FEATURE
<222> LOCATION: (139)..(139)
<223> OTHER INFORMATION: Xaa can be A, R, N, D, C, E, Q, G, H, K, P, S
      T, Y

<400> SEQUENCE: 8
```

Arg Ala Asp Pro Asp Pro Met Lys Asn Thr Cys Lys Leu Leu Val Val
1               5                   10                  15

Ala Asp His Arg Phe Tyr Arg Tyr Met Gly Arg Gly Glu Glu Ser Thr
            20                  25                  30

Thr Thr Asn Tyr Leu Ile Glu Leu Ile Asp Arg Val Asp Asp Ile Tyr
        35                  40                  45

Arg Asn Thr Ala Trp Asp Asn Ala Gly Phe Lys Gly Tyr Gly Ile Gln
    50                  55                  60

Ile Glu Gln Ile Arg Ile Leu Lys Ser Pro Gln Glu Val Lys Pro Gly
65                  70                  75                  80

Glu Lys His Tyr Asn Met Ala Lys Ser Tyr Pro Asn Glu Glu Lys Asp
                85                  90                  95

Ala Trp Asp Val Lys Met Leu Leu Glu Gln Phe Ser Phe Asp Ile Ala
            100                 105                 110

Glu Glu Ala Ser Lys Val Cys Leu Ala His Leu Phe Thr Tyr Gln Asp
        115                 120                 125

Phe Asp Met Gly Thr Leu Gly Leu Ala Tyr Xaa Gly Ser Pro Arg Ala
    130                 135                 140

Asn Ser His Gly Gly Val Cys Pro Lys Ala Tyr Tyr Ser Pro Val Gly
145                 150                 155                 160

Lys Lys Asn Ile Tyr Leu Asn Ser Gly Leu Thr Ser Thr Lys Asn Tyr
                165                 170                 175

Gly Lys Thr Ile Leu Thr Lys Glu Ala Asp Leu Val Thr Thr His Glu
            180                 185                 190

Leu Gly His Asn Phe Gly Ala Glu His Asp Pro Asp Gly Leu Ala Glu
        195                 200                 205

Cys Ala Pro Asn Glu Asp Gln Gly Gly Lys Tyr Val Met Tyr Pro Ile
    210                 215                 220

Ala Val Ser Gly Asp His Glu Asn Asn Lys Met Phe Ser Gln Cys Ser
225                 230                 235                 240

Lys Gln Ser Ile Tyr Lys Thr Ile Glu Ser Lys Ala Gln Glu Cys Phe
                245                 250                 255

Gln Glu Arg Ser Asn Lys Val
            260

```
<210> SEQ ID NO 9
<211> LENGTH: 1458
<212> TYPE: DNA
<213> ORGANISM: Homo sapiens

<400> SEQUENCE: 9
```
atgaggcagt ctctcctatt cctgaccagc gtggttcctt tcgtgctggc gccgcgacct       60
ccggatgacc cgggcttcgg cccccaccag aggctcgaga agcttgattc tttgctctca      120
gactacgata ttctctcttt atctaatatc cagcagcatt cggtaagaaa aagagatcta      180
cagacttcaa cacatgtaga aacactacta acttttcag ctttgaaaag gcattttaaa       240
ttatacctga catcaagtac tgaacgtttt tcacaaaatt tcaaggtcgt ggtggtggat      300

-continued

| | |
|---|---|
| ggtaaaaacg aaagcgagta cactgtaaaa tggcaggact tcttcactgg acacgtggtt | 360 |
| ggtgagcctg actctagggt tctagcccac ataagagatg atgatgttat aatcagaatc | 420 |
| aacacagatg gggccgaata taacatagag ccactttgga gatttgttaa tgataccaaa | 480 |
| gacaaaagaa tgttagttta taaatctgaa gatatcaaga atgtttcacg tttgcagtct | 540 |
| ccaaaagtgt gtggttattt aaaagtggat aatgaagagt tgctcccaaa agggttagta | 600 |
| gacagagaac cacctgaaga gcttgttcat cgagtgaaaa gaagagctga cccagatccc | 660 |
| atgaagaaca cgtgtaaatt attggtggta gcagatcatc gcttctacag atacatgggc | 720 |
| agaggggaag agagtacaac tacaaattac ttaatagagc taattgacag agttgatgac | 780 |
| atctatcgga acactgcatg ggataatgca ggttttaaag gctatggaat acagatagag | 840 |
| cagattcgca ttctcaagtc tccacaagag gtaaaacctg gtgaaaagca ctacaacatg | 900 |
| gcaaaaagtt acccaaatga agaaaaggat gcttgggatg tgaagatgtt gctagagcaa | 960 |
| tttagctttg atatagctga ggaagcatct aaagtttgct tggcacacct tttcacatac | 1020 |
| caagattttg atatgggaac tcttggatta gcttatgttg gctctcccag agcaaacagc | 1080 |
| catggaggtg tttgtccaaa ggcttattat agcccagttg ggaagaaaaa tatctatttg | 1140 |
| aatagtggtt tgacgagcac aaagaattat ggtaaaacca tccttacaaa ggaagctgac | 1200 |
| ctggttacaa ctcatgaatt gggacataat tttggagcag aacatgatcc ggatggtcta | 1260 |
| gcagaatgtg ccccgaatga ggaccaggga gggaaatatg tcatgtatcc catagctgtg | 1320 |
| agtggcgatc acgagaacaa taagatgttt tcacagtgca gtaaacaatc aatctataag | 1380 |
| accattgaaa gtaaggccca ggagtgtttt caagaacgca gcaataaagt tgggagccac | 1440 |
| catcatcacc atcactaa | 1458 |

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10

| | |
|---|---|
| cgcggatcca tgaggcagtc tctcctattc ctg | 33 |

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11

| | |
|---|---|
| ccggcctacc ttagtgatgg tgatgatggt gggatc | 36 |

<210> SEQ ID NO 12
<211> LENGTH: 42
<212> TYPE: DNA
<213> ORGANISM: Artificial Sequence
<220> FEATURE:
<223> OTHER INFORMATION: primer

<400> SEQUENCE: 12

| | |
|---|---|
| ggaactcttg gattagctta tggaggctct cccagagcaa ac | 42 |

<210> SEQ ID NO 13
<211> LENGTH: 42

```
<212> TYPE: DNA
<213> ORGANISM: Artificial Sequence
<220> FEATURE:
<223> OTHER INFORMATION: primer

<400> SEQUENCE: 13
gtttgctctg ggagagcctc cataagctaa tccaagagtt cc                           42

<210> SEQ ID NO 14
<211> LENGTH: 42
<212> TYPE: DNA
<213> ORGANISM: Artificial Sequence
<220> FEATURE:
<223> OTHER INFORMATION: primer

<400> SEQUENCE: 14
ggaactcttg gattagctta tagcggctct cccagagcaa ac                           42

<210> SEQ ID NO 15
<211> LENGTH: 42
<212> TYPE: DNA
<213> ORGANISM: Artificial Sequence
<220> FEATURE:
<223> OTHER INFORMATION: primer

<400> SEQUENCE: 15
gtttgctctg ggagagccgc tataagctaa tccaagagtt cc                           42

<210> SEQ ID NO 16
<211> LENGTH: 10
<212> TYPE: PRT
<213> ORGANISM: Artificial Sequence
<220> FEATURE:
<223> OTHER INFORMATION: internal cleavage site

<400> SEQUENCE: 16

Leu Gly Leu Ala Tyr Val Gly Ser Pro Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: artificial substrate
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 17

Ser Pro Leu Ala Gln Ala Val Arg Ser Ser Ser Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: artificial substrate
<220> FEATURE:
<221> NAME/KEY: MOD_RES
<222> LOCATION: (1)..(1)
<223> OTHER INFORMATION: modified by comprising an epsilon
      N-methoxycoumarin.
```

```
<220> FEATURE:
<221> NAME/KEY: MOD_RES
<222> LOCATION: (14)..(14)
<223> OTHER INFORMATION: modified by comprising an epsilon
      N-dinitrophenyl.

<400> SEQUENCE: 18

Lys Ser Pro Leu Ala Gln Ala Val Arg Ser Ser Ser Arg Lys
1               5                   10

<210> SEQ ID NO 19
<211> LENGTH: 789
<212> TYPE: DNA
<213> ORGANISM: Homo sapiens

<400> SEQUENCE: 19
agagctgacc cagatcccat gaagaacacg tgtaaattat tggtggtagc agatcatcgc      60
ttctacagat acatgggcag aggggaagag agtacaacta caaattactt aatagagcta     120
attgacagag ttgatgacat ctatcggaac actgcatggg ataatgcagg ttttaaaggc     180
tatggaatac agatagagca gattcgcatt ctcaagtctc cacaagaggt aaaacctggt     240
gaaaagcact acaacatggc aaaaagttac ccaaatgaag aaaaggatgc ttgggatgtg     300
aagatgttgc tagagcaatt tagctttgat atagctgagg aagcatctaa agtttgcttg     360
gcacaccttt tcacatacca agattttgat atgggaactc ttggattagc ttatggaggc     420
tctcccagag caaacagcca tggaggtgtt tgtccaaagg cttattatag cccagttggg     480
aagaaaaata tctatttgaa tagtggtttg acgagcacaa agaattatgg taaaaccatc     540
cttacaaagg aagctgacct ggttacaact catgaattgg acataattt tggagcagaa     600 catgatccgg atggtctagc agaatgtgcc ccgaatgagg accagggagg gaaatatgtc     660
atgtatccca tagctgtgag tggcgatcac gagaacaata agatgttttc acagtgcagt     720
aaacaatcaa tctataagac cattgaaagt aaggcccagg agtgttttca agaacgcagc     780
aataaagtt                                                             789

<210> SEQ ID NO 20
<211> LENGTH: 263
<212> TYPE: PRT
<213> ORGANISM: Homo sapiens

<400> SEQUENCE: 20

Arg Ala Asp Pro Asp Pro Met Lys Asn Thr Cys Lys Leu Leu Val Val
1               5                   10                  15

Ala Asp His Arg Phe Tyr Arg Tyr Met Gly Arg Gly Glu Glu Ser Thr
                20                  25                  30

Thr Thr Asn Tyr Leu Ile Glu Leu Ile Asp Arg Val Asp Asp Ile Tyr
            35                  40                  45

Arg Asn Thr Ala Trp Asp Asn Ala Gly Phe Lys Gly Tyr Gly Ile Gln
        50                  55                  60

Ile Glu Gln Ile Arg Ile Leu Lys Ser Pro Gln Glu Val Lys Pro Gly
65                  70                  75                  80

Glu Lys His Tyr Asn Met Ala Lys Ser Tyr Pro Asn Glu Glu Lys Asp
                85                  90                  95

Ala Trp Asp Val Lys Met Leu Leu Glu Gln Phe Ser Phe Asp Ile Ala
            100                 105                 110

Glu Glu Ala Ser Lys Val Cys Leu Ala His Leu Phe Thr Tyr Gln Asp
        115                 120                 125
```

-continued

```
Phe Asp Met Gly Thr Leu Gly Leu Ala Tyr Gly Gly Ser Pro Arg Ala
    130                 135                 140

Asn Ser His Gly Gly Val Cys Pro Lys Ala Tyr Tyr Ser Pro Val Gly
145                 150                 155                 160

Lys Lys Asn Ile Tyr Leu Asn Ser Gly Leu Thr Ser Thr Lys Asn Tyr
                165                 170                 175

Gly Lys Thr Ile Leu Thr Lys Glu Ala Asp Leu Val Thr Thr His Glu
                180                 185                 190

Leu Gly His Asn Phe Gly Ala Glu His Asp Pro Asp Gly Leu Ala Glu
            195                 200                 205

Cys Ala Pro Asn Glu Asp Gln Gly Gly Lys Tyr Val Met Tyr Pro Ile
    210                 215                 220

Ala Val Ser Gly Asp His Glu Asn Asn Lys Met Phe Ser Gln Cys Ser
225                 230                 235                 240

Lys Gln Ser Ile Tyr Lys Thr Ile Glu Ser Lys Ala Gln Glu Cys Phe
                245                 250                 255

Gln Glu Arg Ser Asn Lys Val
            260
```